(12) United States Patent
Edwards et al.

(10) Patent No.: US 8,021,344 B2
(45) Date of Patent: Sep. 20, 2011

(54) MEDICAMENT DELIVERY DEVICE CONFIGURED TO PRODUCE AN AUDIBLE OUTPUT

(75) Inventors: Eric S. Edwards, Midlothian, VA (US); Evan T. Edwards, Gordonsville, VA (US); Mark J. Licata, Doswell, VA (US); Paul F. Meyers, Fishers, IN (US); David A. Weinzierl, Andover, MN (US)

(73) Assignee: Intelliject, Inc., Richmond, VA (US)

( * ) Notice: Subject to any disclaimer, the term of this patent is extended or adjusted under 35 U.S.C. 154(b) by 462 days.

(21) Appl. No.: 12/180,708

(22) Filed: Jul. 28, 2008

(65) Prior Publication Data

US 2010/0022963 A1    Jan. 28, 2010

(51) Int. Cl.
*A61M 5/32*    (2006.01)
(52) U.S. Cl. ........................................ 604/197; 381/396
(58) Field of Classification Search .................. 604/197, 604/67; 381/396, 100
See application file for complete search history.

(56) References Cited

U.S. PATENT DOCUMENTS

| | | | |
|---|---|---|---|
| 2,277,907 A * | 3/1942 | Goodale, Jr. et al. | 379/420.01 |
| 3,055,362 A | 9/1962 | Uytenbogaart | |
| 4,484,910 A | 11/1984 | Sarnoff | |
| 4,617,557 A | 10/1986 | Gordon | |
| 4,795,433 A | 1/1989 | Sarnoff | |
| 4,853,521 A | 8/1989 | Claeys et al. | |
| 4,894,054 A | 1/1990 | Miskinyar | |
| 4,959,056 A | 9/1990 | Dombrowski et al. | |
| 5,343,519 A | 8/1994 | Feldman | |
| 5,363,842 A | 11/1994 | Mishelevich et al. | |
| 5,568,555 A | 10/1996 | Shamir | |
| 5,610,992 A | 3/1997 | Hickman | |
| 5,616,132 A | 4/1997 | Newman | |
| 5,662,612 A | 9/1997 | Niehoff | |
| 5,692,492 A | 12/1997 | Bruna et al. | |
| 5,697,916 A | 12/1997 | Schraga | |
| 5,772,635 A | 6/1998 | Dastur et al. | |
| 5,792,190 A | 8/1998 | Olson et al. | |
| 5,809,997 A | 9/1998 | Wolf | |
| 5,813,397 A | 9/1998 | Goodman et al. | |

(Continued)

FOREIGN PATENT DOCUMENTS

EP    1043037 A2    10/2000

(Continued)

OTHER PUBLICATIONS

"Flexible circuits / Flex circuits / Flexible Technology Ltd.," Flexible Technology Limited [online] [retrieved on Aug. 28, 2006] Retrieved from the Internet <URL: http://www.flexibletechnology.com/>.

(Continued)

*Primary Examiner* — Theodore Stigell
*Assistant Examiner* — Brandy C Scott
(74) *Attorney, Agent, or Firm* — Cooley LLP

(57) ABSTRACT

Medicament delivery devices are described herein. In some embodiments, an apparatus includes a medicament delivery device and an electronic circuit system. The medicament delivery device includes a housing, a medicament container, and a medicament delivery member. The electronic circuit system is coupled to the housing and includes an audible output device and a cover. The housing of the medicament delivery device and the cover of the electronic circuit system collectively define an acoustic enclosure. The audible output device is configured to be disposed within the acoustic enclosure.

25 Claims, 31 Drawing Sheets

U.S. PATENT DOCUMENTS

| | | | |
|---|---|---|---|
| 5,832,488 A | 11/1998 | Eberhardt | |
| 5,846,089 A | 12/1998 | Weiss et al. | |
| 5,848,988 A | 12/1998 | Davis | |
| 5,852,590 A | 12/1998 | de la Huerga | |
| 5,853,292 A | 12/1998 | Eggert et al. | |
| 5,925,021 A | 7/1999 | Castellano et al. | |
| 5,928,195 A | 7/1999 | Malamud | |
| 5,970,457 A | 10/1999 | Brant et al. | |
| 6,002,781 A | 12/1999 | Takayama et al. | |
| 6,074,213 A | 6/2000 | Hon | |
| 6,077,106 A | 6/2000 | Mish | |
| 6,084,526 A | 7/2000 | Blotky et al. | |
| 6,086,562 A | 7/2000 | Jacobsen et al. | |
| 6,119,684 A | 9/2000 | Nöhl et al. | |
| 6,144,310 A | 11/2000 | Morris | |
| 6,158,613 A | 12/2000 | Novosel et al. | |
| 6,165,155 A | 12/2000 | Jacobsen et al. | |
| 6,175,752 B1 | 1/2001 | Say | |
| 6,200,289 B1 * | 3/2001 | Hochman et al. | 604/67 |
| 6,202,642 B1 | 3/2001 | McKinnon et al. | |
| 6,219,587 B1 | 4/2001 | Ahlin et al. | |
| 6,259,654 B1 | 7/2001 | de la Huerga | |
| 6,270,455 B1 | 8/2001 | Brown | |
| 6,285,757 B1 | 9/2001 | Carroll et al. | |
| 6,317,630 B1 | 11/2001 | Gross et al. | |
| 6,321,070 B1 | 11/2001 | Clark et al. | |
| 6,323,780 B1 | 11/2001 | Morris | |
| 6,334,070 B1 | 12/2001 | Nova et al. | |
| 6,398,760 B1 | 6/2002 | Danby | |
| 6,411,567 B1 | 6/2002 | Niemiec et al. | |
| 6,478,769 B1 | 11/2002 | Parker | |
| 6,500,150 B1 | 12/2002 | Gross et al. | |
| 6,529,446 B1 | 3/2003 | de la Huerga | |
| 6,530,904 B1 | 3/2003 | Edwards et al. | |
| 6,535,714 B2 | 3/2003 | Melker et al. | |
| 6,540,675 B2 | 4/2003 | Aceti et al. | |
| 6,551,276 B1 | 4/2003 | Mann et al. | |
| 6,554,798 B1 | 4/2003 | Mann et al. | |
| 6,558,320 B1 | 5/2003 | Causey, III et al. | |
| 6,560,471 B1 | 5/2003 | Heller | |
| 6,574,166 B2 | 6/2003 | Niemiec | |
| RE38,189 E | 7/2003 | Walker et al. | |
| 6,585,698 B1 | 7/2003 | Packman et al. | |
| 6,595,956 B1 | 7/2003 | Gross et al. | |
| 6,597,794 B2 | 7/2003 | Cole et al. | |
| 6,633,796 B1 | 10/2003 | Pool et al. | |
| 6,659,980 B2 | 12/2003 | Moberg et al. | |
| 6,679,862 B2 | 1/2004 | Diaz et al. | |
| 6,723,077 B2 | 4/2004 | Pickup et al. | |
| 6,736,796 B2 | 5/2004 | Shekalim | |
| 6,743,635 B2 | 6/2004 | Neel et al. | |
| 6,749,437 B2 | 6/2004 | Chan | |
| 6,752,781 B2 | 6/2004 | Landau et al. | |
| 6,783,509 B1 | 8/2004 | Landau et al. | |
| 6,786,885 B2 | 9/2004 | Hochman et al. | |
| 6,803,856 B1 | 10/2004 | Murphy et al. | |
| 6,808,514 B2 | 10/2004 | Schneider et al. | |
| 6,809,653 B1 | 10/2004 | Mann et al. | |
| 6,839,304 B2 | 1/2005 | Niemiec et al. | |
| 6,872,200 B2 | 3/2005 | Mann et al. | |
| 6,923,764 B2 | 8/2005 | Aceti et al. | |
| 6,936,029 B2 | 8/2005 | Mann et al. | |
| 6,937,150 B2 | 8/2005 | Medema et al. | |
| 6,942,646 B2 | 9/2005 | Langley et al. | |
| 6,945,961 B2 | 9/2005 | Miller et al. | |
| 6,946,299 B2 | 9/2005 | Neel et al. | |
| 6,953,693 B2 | 10/2005 | Neel et al. | |
| 6,958,691 B1 | 10/2005 | Anderson et al. | |
| 6,959,247 B2 | 10/2005 | Neel et al. | |
| 6,961,285 B2 | 11/2005 | Niemiec et al. | |
| 6,964,650 B2 | 11/2005 | Alexandre et al. | |
| 6,969,259 B2 | 11/2005 | Pastrick et al. | |
| 6,979,316 B1 | 12/2005 | Rubin et al. | |
| 6,979,326 B2 | 12/2005 | Mann et al. | |
| 6,985,870 B2 | 1/2006 | Martucci et al. | |
| 6,997,911 B2 | 2/2006 | Klitmose | |
| 7,113,101 B2 | 9/2006 | Petersen et al. | |
| 7,116,233 B2 | 10/2006 | Zhurin | |
| 7,126,879 B2 | 10/2006 | Snyder | |
| 7,158,011 B2 | 1/2007 | Brue | |
| 7,191,916 B2 | 3/2007 | Clifford et al. | |
| 7,229,458 B2 | 6/2007 | Boecker et al. | |
| 7,278,983 B2 | 10/2007 | Ireland et al. | |
| 7,343,914 B2 | 3/2008 | Abrams et al. | |
| 2002/0076679 A1 | 6/2002 | Aman | |
| 2002/0090601 A1 | 7/2002 | Strupat et al. | |
| 2002/0096543 A1 | 7/2002 | Juselius | |
| 2003/0028145 A1 | 2/2003 | Duchon et al. | |
| 2003/0060765 A1 | 3/2003 | Campbell et al. | |
| 2003/0100862 A1 | 5/2003 | Edwards et al. | |
| 2003/0120212 A1 | 6/2003 | Dedig et al. | |
| 2003/0132128 A1 * | 7/2003 | Mazur | 206/364 |
| 2003/0135388 A1 | 7/2003 | Martucci et al. | |
| 2003/0233070 A1 | 12/2003 | De La Serna et al. | |
| 2004/0069667 A1 | 4/2004 | Tomellini et al. | |
| 2004/0143298 A1 | 7/2004 | Nova et al. | |
| 2005/0033386 A1 | 2/2005 | Osborn et al. | |
| 2005/0062603 A1 | 3/2005 | Fuerst et al. | |
| 2005/0090781 A1 | 4/2005 | Baba et al. | |
| 2005/0134433 A1 | 6/2005 | Sweeney, II | |
| 2005/0137530 A1 | 6/2005 | Campbell et al. | |
| 2005/0168337 A1 | 8/2005 | Mahoney | |
| 2005/0182358 A1 | 8/2005 | Veit et al. | |
| 2005/0197654 A1 | 9/2005 | Edman et al. | |
| 2005/0261742 A1 | 11/2005 | Nova et al. | |
| 2005/0267403 A1 | 12/2005 | Landau et al. | |
| 2006/0030819 A1 | 2/2006 | Young et al. | |
| 2006/0053036 A1 | 3/2006 | Coffman et al. | |
| 2006/0058848 A1 | 3/2006 | Piraino et al. | |
| 2006/0265186 A1 | 11/2006 | Holland et al. | |
| 2007/0008113 A1 | 1/2007 | Spoonhower et al. | |
| 2007/0074722 A1 | 4/2007 | Giroux et al. | |
| 2007/0088268 A1 | 4/2007 | Edwards et al. | |
| 2007/0129708 A1 | 6/2007 | Edwards et al. | |
| 2007/0149925 A1 | 6/2007 | Edwards et al. | |
| 2007/0149954 A1 | 6/2007 | Hood et al. | |
| 2007/0184847 A1 | 8/2007 | Hansen et al. | |
| 2007/0210147 A1 | 9/2007 | Morrone et al. | |
| 2007/0213598 A1 | 9/2007 | Howard et al. | |
| 2007/0239114 A1 | 10/2007 | Edwards et al. | |
| 2007/0239140 A1 | 10/2007 | Chechelski et al. | |
| 2008/0033393 A1 | 2/2008 | Edwards et al. | |
| 2008/0058719 A1 | 3/2008 | Edwards et al. | |
| 2008/0059133 A1 | 3/2008 | Edwards et al. | |
| 2008/0103490 A1 | 5/2008 | Edwards et al. | |
| 2008/0111685 A1 | 5/2008 | Olson et al. | |
| 2008/0160492 A1 | 7/2008 | Campbell et al. | |
| 2008/0230057 A1 | 9/2008 | Sutherland | |
| 2008/0249468 A1 | 10/2008 | Edwards et al. | |
| 2008/0298188 A1 | 12/2008 | Hamelinck et al. | |
| 2010/0211005 A1 | 8/2010 | Edwards et al. | |
| 2010/0309012 A1 | 12/2010 | Edwards et al. | |
| 2010/0318035 A1 | 12/2010 | Edwards et al. | |

FOREIGN PATENT DOCUMENTS

| | | |
|---|---|---|
| EP | 1 287 840 A1 | 5/2003 |
| EP | 1462134 A1 | 9/2004 |
| EP | 1 712 178 A2 | 10/2006 |
| WO | WO 95/26009 | 9/1995 |
| WO | WO 01/24690 A2 | 4/2001 |
| WO | WO 01/26020 A1 | 4/2001 |
| WO | WO 01/41849 A2 | 6/2001 |
| WO | WO 01/88828 | 11/2001 |
| WO | WO 01/93926 A2 | 12/2001 |
| WO | WO 03/057283 A1 | 7/2003 |
| WO | WO 2004/041330 A2 | 5/2004 |
| WO | WO 2005/050526 A2 | 6/2005 |
| WO | WO 2006/045525 A1 | 5/2006 |
| WO | WO 2006/109778 A1 | 10/2006 |
| WO | WO2006/125692 | 11/2006 |

OTHER PUBLICATIONS

"Flexible circuits capabilities of Flexible Technology Limited," Our Flexible Circuits Capabilities [online] [retrieved on Aug. 28, 2006] Retrieved from the Internet <URL: http://www.flexibletechnology.com/Flexible_circuits_Capability.htm >.

"Flex Circuits/flexible circuits design guide," [online] [retrieved on Aug. 28, 2006] Retrieved from the Internet <URL: http://flexiblecircuit.co.uk/Flex_Circuits_Design—Guide.htm >.

"Merck Serono Launches easypod(R), First Electronic Growth Hormone Injection Device," Jan. 30, 2007 [online] [retrieved on Feb. 5, 2007] Retrieved from the Internet <URL: http://www.biz.vahoo.com/prnews/070130/ukm028.html?.v=8.

CliniSense Corporation, "Drug delivery devices A potentially harsh environment for drugs," Stability [online] [retrieved on Jun. 1, 2007] Retrieved from the Internet <URL: http://www.clinisense.com/devices.htm>.

CliniSense Corporation, "LifeTrack Technology A new method to detect improper storage." Stability [online] [retrieved on Jun. 1, 2007] Retrieved from the Internet <URL: http://www.clinisense.com/tech.htm>.

International Search Report and Written Opinion for International Patent Application No. PCT/US06/03415 mailed Jul. 13, 2006, 10 pages.

IPRP for International Patent Application No. PCT/US2009/043578, mailed Nov. 17, 2010.

Final Office Action for U.S. Appl. No. 11/679,331, mailed Feb. 15, 2011.

Office Action for U.S. Appl. No. 11/671,025, mailed Mar. 24, 2011.

Office Action for Japanese Patent Application No. JP2007-553358, mailed Mar. 17, 2011.

* cited by examiner

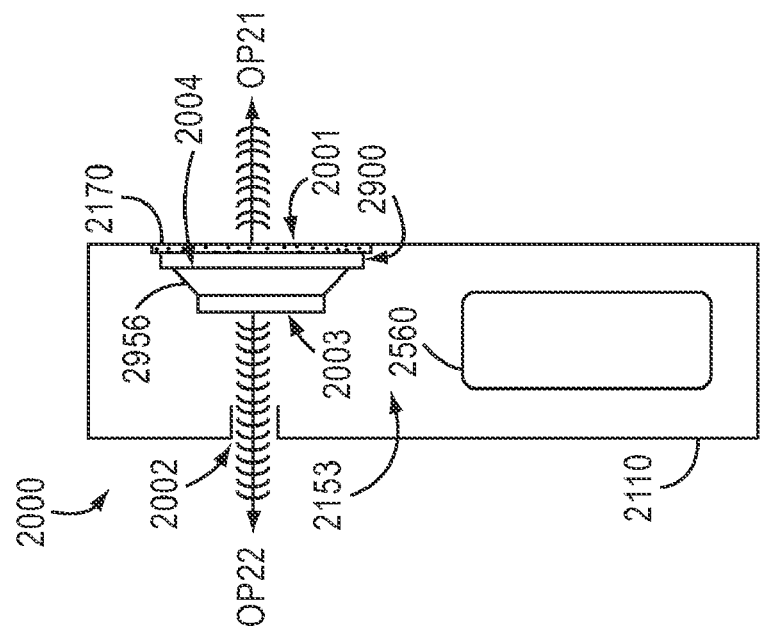
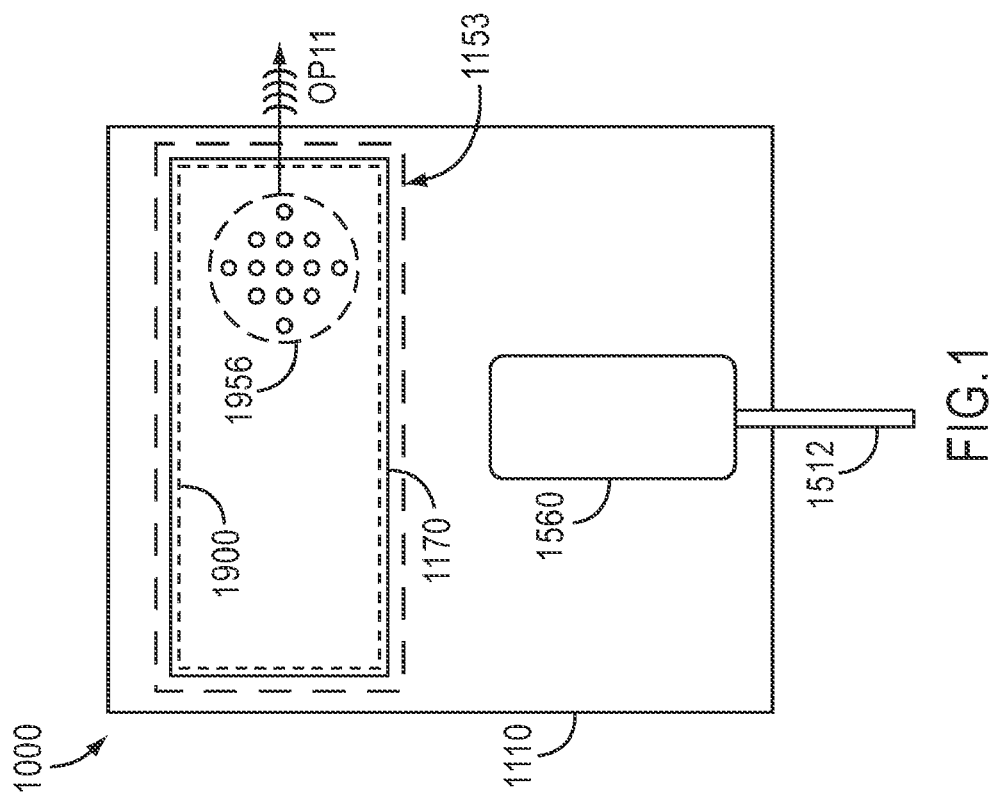

MEDICAMENT DELIVERY DEVICE CONFIGURED TO PRODUCE AN AUDIBLE OUTPUT

BACKGROUND

The invention relates generally to a medical device, and more particularly to a medicament delivery device having an electronic circuit system that produces an audible output.

Exposure to certain substances, such as, for example, peanuts, shellfish, bee venom, certain drugs, toxins, and the like, can cause allergic reactions in some individuals. Such allergic reactions can, at times, lead to anaphylactic shock, which can cause a sharp drop in blood pressure, hives, and/or severe airway constriction. Accordingly, responding rapidly to mitigate the effects from such exposures can prevent injury and/or death. For example, in certain situations, an injection of epinephrine (i.e., adrenaline) can provide substantial and/or complete relief from the allergic reaction. In other situations, for example, an injection of an antidote to a toxin can greatly reduce and/or eliminate the harm potentially caused by the exposure. Because emergency medical facilities may not be available when an individual is suffering from an allergic reaction, some individuals carry a medicament delivery device, such as, for example, an auto-injector, to rapidly self-administer a medicament in response to an allergic reaction.

To actuate such a medicament delivery device, however, the user may be required to execute a series of operations. For example, to actuate some known auto-injectors, the user must remove a protective cap, remove a locking device, place the auto-injector in a proper position against the body and then press a button to actuate the auto-injector. Failure to complete these operations properly can result in an incomplete injection and/or injection into an undesired location of the body. In certain instances, for example, users who have become confused in the operation of some known auto-injectors have inadvertently injected the medicament into their thumb by improperly positioning the auto-injector.

The likelihood of improper use of known medicament delivery devices can be compounded by the nature of the user and/or the circumstances under which such devices are used. For example, many users are not trained medical professionals and may have never been trained in the operation of such devices. Moreover, in certain situations, the user may not be the patient, and may therefore have no experience with the medicament delivery device. Similarly, because some known medicament delivery devices are configured to be used relatively infrequently in response to an allergic reaction or the like, even those users familiar with the device and/or who have been trained may not be well practiced at operating the device. Finally, such devices are often used during an emergency situation, during which even experienced and/or trained users may be subject to confusion, panic, and/or the physiological effects of the condition requiring treatment.

Some known medicament delivery devices include printed instructions to inform the user of the steps required to properly deliver the medicament. Such printed instructions, however, can be inadequate for the class of users and/or the situations described above. Moreover, because some known medicament delivery devices, such as, for example, auto-injectors, pen injectors, inhalers or the like, can be compact, such printed instructions may be too small to read and comprehend during an emergency situation.

Some known medicament delivery devices can produce sounds, such as a beep or a click, that can be used as prompts to users of medicament delivery devices. The sounds of such known devices and the manner in which the sounds are produced, however, provide limited information to the user. For example, some known medicament delivery devices produce a single tone to indicate that a proper dosage has been set but cannot provide a user with instructions associated with the use of the device. Moreover, the sound level and/or the quality of the sound produced by such known medicament delivery devices is limited by the size, performance, and/or cost associated with the speaker and/or electronic components necessary to produce the sounds.

Thus, a need exists for medicament delivery systems and/or devices that provide instructions, messages, information, and/or directions that are easily understood and/or heard by a user in any type of situation.

SUMMARY

Medicament delivery devices are described herein. In some embodiments, an apparatus includes a medicament delivery device and an electronic circuit system. The medicament delivery device includes a housing, a medicament container, and a medicament delivery member. The electronic circuit system is coupled to the housing and includes an audible output device and a cover. The housing of the medicament delivery device and the cover of the electronic circuit system collectively define an acoustic enclosure. The audible output device is configured to be disposed within the acoustic enclosure.

BRIEF DESCRIPTION OF THE DRAWINGS

FIG. 1 is a schematic illustration of a medicament delivery device having an acoustic enclosure, according to an embodiment of the invention.

FIG. 2 is a schematic illustration of a medicament delivery device having a ported acoustic enclosure, according to an embodiment of the invention.

DETAILED DESCRIPTION

Figure 3:
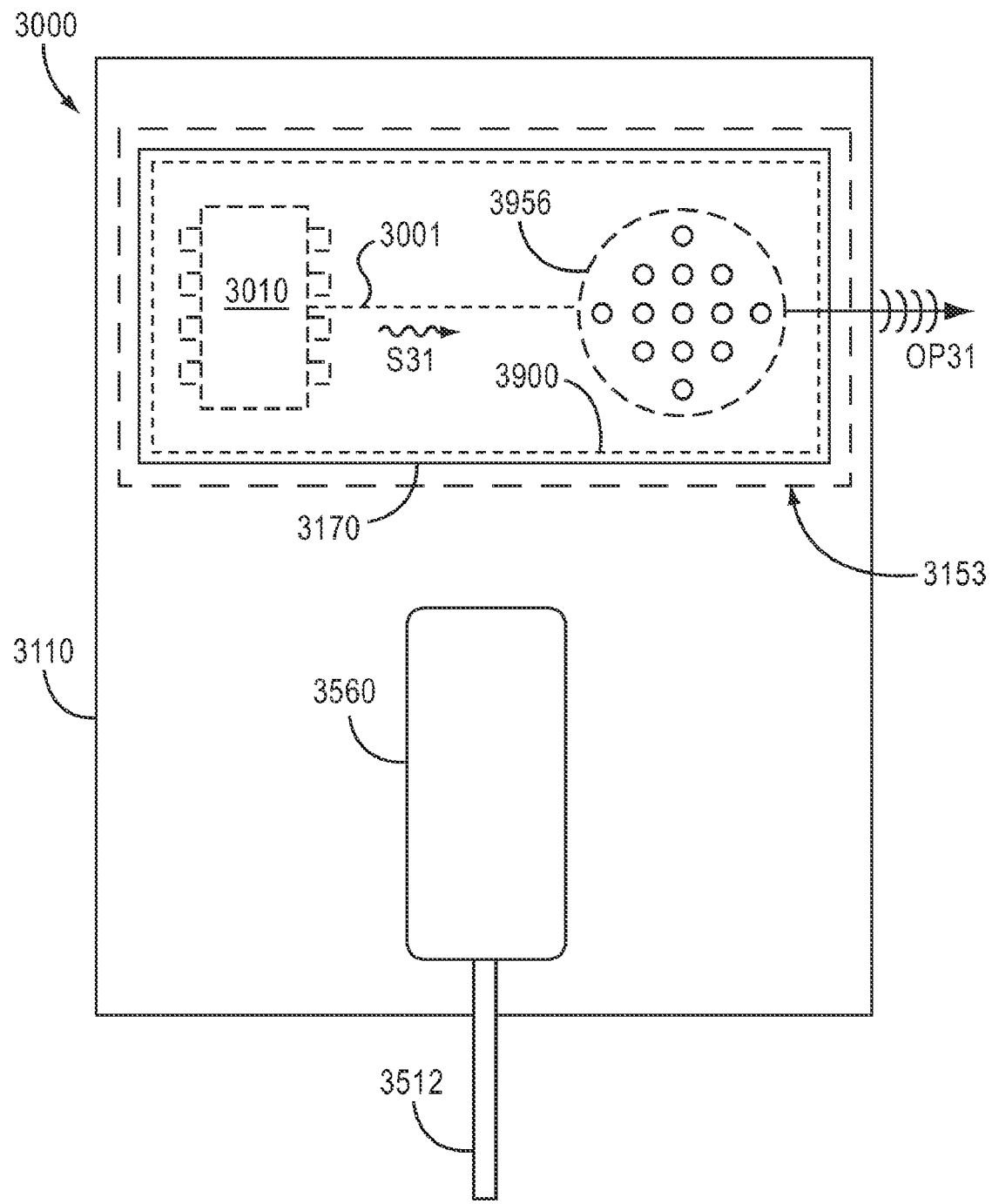
FIG. 3 is a schematic illustration of a medicament delivery device according to an embodiment of the invention.

In some embodiments, an apparatus includes a medicament delivery device and an electronic circuit system. The medicament delivery device includes a housing, a medicament container, and a medicament delivery member. The medicament container and at least a portion of the medicament delivery member are disposed within the housing. The electronic circuit system is coupled to the housing and includes an audible output device and a cover. The housing of the medicament delivery device and the cover of the electronic circuit system collectively define an acoustic enclosure. The audible output device, which can be, for example, a speaker, is configured to be disposed within the acoustic enclosure.

In some embodiments, an apparatus includes a medicament delivery device and an electronic circuit system. The medicament delivery device includes a housing and a medicament container. The medicament container is disposed within the housing. The electronic circuit system is coupled to the housing and includes a speaker and a cover. The speaker includes a front portion and a back portion. The front portion of the speaker is configured to output a first audible output including a first set of sound waves. The back portion of the speaker is configured to output a second audible output including a second set of sound waves. The housing of the medicament delivery device defines a first opening through which the first set of sound waves is configured to travel. The cover of the electronic circuit system defines a second opening through which the second set of sound waves is configured to travel.

In some embodiments, an apparatus includes a medicament delivery device and an electronic circuit system, the medicament delivery device including a housing, a medicament container, and a medicament delivery member. The medicament container and at least a portion of the medicament delivery member are disposed within the housing. The electronic circuit system is coupled to the housing and includes an audio processor and an audible output device. The audio processor is configured to output an electronic signal associated with recorded speech to the audible output device via an electronic path devoid of an amplifier. The audible output device can be configured to output an audible output in response to the electronic signal.

As used in this specification including the appended claims, the words "proximal" and "distal" refer to direction closer to and away from, respectively, an operator (e.g., surgeon, physician, nurse, technician, etc.) of the medical device. Thus, for example, the end of the medicament delivery device contacting the patient's body would be the distal end of the medicament delivery device, while the end opposite the distal end would be the proximal end of the medicament delivery device.

FIG. 1 is a schematic illustration of a medicament delivery device 1000 having an acoustic enclosure, according to an embodiment of the invention. The medicament delivery device 1000 includes a housing 1110, a medicament container 1560, a medicament delivery member 1512, and an electronic circuit system 1900. The medicament container 1560, which can be, for example, a pre-filled cartridge, a vial, an ampule, or the like, is disposed within the housing 1110. At least a portion of the medicament delivery member 1512 is disposed within the housing 1110. In some configurations, the medicament delivery member 1512 can be in fluid communication with the medicament container 1560. In this manner, a medicament can be conveyed from the medicament container 1560 to a region outside the housing 1110 via the medicament delivery member 1512. The medicament delivery member 1512 can include, for example, a needle, a nozzle, a mouthpiece, or the like.

In some embodiments, the medicament delivery device 1000 can be any suitable medical injector for injecting a medicament into a body of a patient. For example, the medicament delivery device 1000 can be a syringe, pen injector, auto-injector, or the like. In other embodiments, the medicament delivery device 1000 can be an inhaler. In yet another embodiment, the medicament delivery device 1000 can be a transdermal delivery system. In some embodiments, the medicament delivery device 1000 can be a chronic-care medicament delivery device. Said another way, the medicament delivery device 1000 can be a reusable device containing multiple doses of medicament. For example, a medicament delivery device 1000 having multiple doses of medicament can be used to manage insulin delivery or the delivery of other medicaments (e.g., to treat Multiple Sclerosis, Anemia, Rheumatoid Arthritis, Osteoporosis or the like), which can, in some instances, require daily, weekly, and/or monthly dosages. In other embodiments, the medicament delivery device 1000 can be a single-use device. Said another way, the medicament delivery device 1000 can contain a single dose of medicament. In yet other embodiments, the medicament delivery device 1000 can be a simulated medicament delivery device or trainer similar to the simulated medicament delivery devices or trainers described in U.S. Patent Publication Number 2008/0059133, entitled "Medical Injector Simulation Device," filed Feb. 27, 2007, which is incorporated herein by reference in its entirety.

The electronic circuit system 1900 includes an audible output device 1956 and a cover 1170 coupled to the housing 1110. The audible output device 1956, which can be, for example, a microspeaker, is configured to produce an audible output OP11. Said another way, the audible output device 1956 is configured to produce a set of sound waves in response to an electronic signal from the electronic circuit system 1900. In some embodiments, the electronic circuit system 1900 and the audible output device 1956 can produce the audible output OP11 in association with the use of the medicament delivery device 1000.

The electronic circuit system 1900 can include any suitable electronic components operatively coupled to produce and/or output the audible output OP11 and/or to perform the functions described herein. In some embodiments, the electronic circuit system 1900 can be similar to the electronic circuit systems described in U.S. Patent Publication Number 2008/0033393, entitled "Devices, Systems and Methods for Medicament Delivery," filed Jan. 9, 2007, which is incorporated herein by reference in its entirety.

The housing 1110 and the cover 1170 of the electronic circuit system 1900 collectively define a region 1153. Although the region 1153 is illustrated in FIG. 1 as a two-dimensional area, the region 1153 is associated with an enclosed volume or space within the housing 1110. Similarly stated, the region 1153 can be a cavity, a chamber, or an enclosure defined by the housing 1110 and the cover 1170. In some embodiments, the region 1153 can be associated with a volume or space within the housing 1110 having at least one opening (not shown in FIG. 1) to an area outside of the housing 1110.

At least a portion of the electronic circuit system 1900 is disposed within the region 1153 of the housing 1110. The electronic circuit system 1900 is coupled to the housing 1110 such that the audible output device 1956 is disposed within the region 1153 defined by the housing 1110 and the cover 1170. Moreover, the volume associated with the region 1153 is larger than the volume of the audible output device 1956. In this manner, the region 1153 can function as an acoustic enclosure for the audible output device 1956. As an acoustic enclosure, the region 1153 can be used to minimize or attenuate noise and/or to enhance the audible output OP11 of the audible output device 1956. In some embodiments, the region 1153 can reduce noise by isolating and/or absorbing sound and/or vibration associated with the audible output device 1956. In some embodiments, the region 1153 can enhance the audible output OP11 of an audible output device 1956 by acoustically amplifying the audible output at one or more acoustic resonant frequencies defined by the physical characteristics of the region 1153 (e.g., volume, shape, or the like). In some embodiments, for example, the region 1153 defines at least one resonant acoustic frequency within the acoustic frequency range of the audible output device 1956.

The audible output OP11 can be, for example, an audible representation of a recorded message or speech, a single tone or a sequence of tones, and/or the like. In some embodiments, the audible output OP11 can be associated with a pre-recorded speech, instruction, or prompt for using the medicament delivery device 1000. In other embodiments, the audible output OP11 can be associated with post-use instructions or prompts, such as, for example, a recorded message notifying the user that the medicament delivery event is complete, instructing the user on post-medicament delivery disposal and safety procedures, instructing the user to seek post-medicament delivery medical treatment, and/or the like. In yet other embodiments, the audible output OP11 can be associated with the patient's compliance in using the medicament delivery device 1000. In some embodiments, the audible output OP11 can be associated with an actuation of the medicament delivery device 1000. Said another way, the audible output device 1956 can be configured to output the audible output OP11 in response to the triggering or activating of a function, procedure, and/or mode associated with the medicament delivery device 1000.

Although the region 1153 is shown as being fully enclosed, in other embodiments the region 1153 can be partially enclosed. In some embodiments, for example, the cover 1170 and/or the housing 1110 define an opening (not shown) through which the audible output device 1956 can be disposed within the region 1153. In some embodiments, the shape of the audible output device 1956 can substantially match the shape of the partially enclosed region 1153. In other embodiments, the volume of the audible output device 1956 disposed within the partially enclosed region 1153 is smaller than the volume of the partially enclosed region 1153.

FIG. 2 is a schematic illustration of a medicament delivery device 2000 having a ported acoustic enclosure, according to an embodiment of the invention. The medicament delivery device 2000 includes a housing 2110, a medicament container 2560, and an electronic circuit system 2900. The medicament container 2560, which can be, for example, a prefilled cartridge, a vial, an ampule, or the like, is disposed within the housing 2110.

The medicament delivery device 2000 can be a reusable device containing multiple doses of medicament. For example, a medicament delivery device 2000 having multiple doses of medicament can be used to manage insulin delivery or the delivery of other medicaments (e.g., to treat Multiple Sclerosis, Anemia, Rheumatoid Arthritis, Osteoporosis or the like), which can, in some instances, require daily, weekly, and/or monthly dosage. In other embodiments, the medicament delivery device 2000 can be a single-use device. Said another way, the medicament delivery device 2000 can contain a single dose of medicament. In yet other embodiments, the medicament delivery device 2000 can be a simulated medicament delivery device or trainer.

The electronic circuit system 2900 can include any suitable electronic components operatively coupled to produce and/or output the audible output and/or to perform the functions described herein. The electronic circuit system 2900 includes an audible output device 2956 and a cover 2170 coupled to the housing 2110. The audible output device 2956, which can be, for example, a microspeaker, includes a front portion 2004 and a back portion 2003. The front portion 2004 of the audible output device 2956 is configured to output a first audible output OP21 that includes a first set of sound waves. The back portion 2003 of the audible output device 2956 is configured to output a second audible output OP22 that includes a second set of sound waves. The first set sound waves associated with the first audible output OP21 can result from changes in air pressure that occur at the front portion 2004 of the audible output device 2956 from, for example, a controlled movement of a portion of the audible output device 2956 (e.g., a cone, membrane, diaphragm, or the like). The second set of sound waves associated with the second audible output OP22 can result from changes in air pressure that occur at the back portion 2003 of the audible output device 2956 from, for example, the movement of a portion of the audible output device 2956. In some embodiments, a single moving portion (e.g., a speaker cone) can produce both the first set of sound waves and the second set of sound waves. For example, a movement of the cone that produces an increase in air pressure at the front portion 2004 of the audible output device 2956 results in a corresponding decrease in air pressure at the back portion 2003 of the audible output device 2956. Similarly, a movement of the cone that produces a decrease in air pressure at the front portion 2004 of the audible output device 2956 results in a corresponding increase in air pressure at the back portion 2003 of the audible output device 2956. Accordingly, in some embodiments, the first set of sound waves produced at the front portion 2004 of the audible output device 2956 can be out-of-phase with the second set of sound waves produced at the back portion 2003 of the audible output device 2956. In this manner, the electronic circuit system 2900 and the audible output device 2956 can produce an audible output associated with the use of the medicament delivery device 2000.

The housing 2110 and the cover 2170 of the electronic circuit system 2900 collectively define a region 2153. Although the region 2153 is illustrated in FIG. 2 as a two-dimensional area, the region 2153 is associated with an enclosed volume or space within the housing 2110. Similarly stated, the region 2153 can be a cavity, a chamber, or an enclosure defined by the housing 2110 and the cover 2170. At least a portion of the electronic circuit system 2900 and/or the audible output device 2956 is disposed within the region 2153 of the housing 2110. In this manner, the region 2153 can function as an acoustic enclosure for the audible output device 2956.

The cover 2170 defines an opening 2001 through which the first set of sound waves associated with the audible output OP21 can travel. Similarly, the housing 2110 defines an opening 2002 through which the second set of sound waves associated with the audible output OP22 can travel. The opening 2002 can be referred to, for example, as a "port" of the acoustic enclosure associated with the region 2153. In some embodiments, the opening 2001 and the opening 2002 can be collectively configured such that the first set of sound waves associated with the audible output OP21 when exiting the housing 2110 through the opening 2001 is substantially in phase with the second set of sound waves associated with the audible output OP22 when exiting the housing 2110 through the opening 2002. Similarly stated, in some embodiments, the opening 2002 can be positioned and/or oriented relative to the opening 2001 to compensate, reduce and/or eliminate the phase difference that can exist between the first set of sound waves of the audible output OP21 and the second set of sound waves of the audible output OP22 within the housing 2110. Said another way, in some embodiments, the distance that the first set of sound waves of the audible output OP21 travels to exit through the opening 2001 (e.g., the distance between the front portion 2004 of the audible output device 2956 and the exit of the opening 2001) and the distance that the second set of sound waves of the audible output OP22 travels to exit through the opening 2002 (e.g., the distance between the back portion 2003 of the audible output device 2956 and the exit of the opening 2002) is such that the first set of sound waves associated with the audible output OP21 when exiting the housing 2110 is substantially in phase with the second set of sound waves associated with the audible output OP22 when exiting the housing 2110 through the opening 2002. In this manner, the phase compensation that results from the difference between the exit path of the first set of sound waves of the audible output OP21 and the exit path of the second set of sound waves of the audible output OP22 can increase (e.g., constructively interfere) the overall sound level of the audible output device 2956 outside the housing 2110.

Although the cover 2170 is shown as defining the opening 2001, in other embodiments, the housing 2110 can define both the opening 2001 and the opening 2002. Although the cover 2170 is described as defining a single opening 2001, in other embodiments, the cover 2170 can define multiple openings. Similarly, in some embodiments, the housing 2110 can define multiple "ports" or openings. In some embodiments, the opening 2002 is configured to be selectively covered by a moveable member (not shown) of the medicament delivery device 2000. For example, the opening 2002 can be selectively covered by at least one of a sleeve, a safety lock, or a needle guard.

The audible outputs OP21 and OP22 can be related to instructions, notifications, messages, actuations, and/or compliance associated with using the medicament delivery device 2000. The audible output OP21 and the audible output OP22 can be, for example, a recorded message or speech, a single tone or a sequence of tones, and/or the like. In this manner, the electronic circuit system 2900 can output information to the user through the audile outputs OP21 and OP22 in an unobtrusive manner and/or without impeding the delivery of the medicaments. The audible outputs OP21 and OP22 can be, for example, audible representations of a recorded message or speech, single tones or sequences of tones, and/or the like. In some embodiments, the audible outputs OP21 and OP22 can be associated with a pre-recorded speech, instruction, or prompt for using the medicament delivery device 2000. In other embodiments, the audible outputs OP21 and OP22 can be associated with post-use instructions or prompts, such as, for example, a recorded message notifying the user that the medicament delivery is complete, instructing the user on post-medicament delivery disposal and safety procedures, instructing the user to seek post-medicament delivery medical treatment, and/or the like. In yet other embodiments, the audible outputs OP21 and OP22 can be associated with the patient's compliance in using the medicament delivery device 2000. In some embodiments, the audible outputs OP21 and OP22 can be associated with an actuation of the medicament delivery device 2000. Said another way, the audible output device 2956 can be configured to output the audible outputs OP21 and OP22 in response to the triggering or activating of a function, procedure, and/or mode associated with the medicament delivery device 2000.

FIG. 3 is a schematic illustration of a medicament delivery device 3000 according to an embodiment of the invention. The medicament delivery device 3000 includes a housing 3110, a medicament container 3560, a medicament delivery member 3512, and an electronic circuit system 3900. The medicament container 3560 is disposed within the housing 3110. At least a portion of the medicament delivery member 3512 is disposed within the housing 3110. The medicament container 3560 and/or the medicament delivery member 3512 can be substantially similar to the medicament container 1560 and/or the medicament delivery member 1512, respectively, as shown and described above with reference to FIG. 1.

The electronic circuit system 3900, which can be can be similar to the electronic circuit system 1900 shown and described above with reference to FIG. 1, includes an audio processor 3010 and an audible output device 3956. The audio processor 3010 is configured to output an electronic output S31 to the audible output device 3956. The audio processor 3010 can be software-based (e.g., set of instructions executable at a processor, software code) and/or hardware-based (e.g., circuit system, processor, application-specific integrated circuit (ASIC), field programmable gate array (FPGA)). The electronic output S31 can be associated with, for example, a recorded message or speech, a single tone or a sequence of tones, and/or the like. In some embodiments, the electronic circuit system 3900 and/or the audio processor 3010 can include a separate memory (not shown) in which information associated with a recorded message or speech, tones, or the like can be stored. In this manner, the audio processor 3010 can receive the recorded message or tone information from the memory for processing and to produce the electronic output S31. In some embodiments, for example, the audio processor 3010 can include an embedded or built-in memory module in which information associated with the recorded message or tone is stored.

As shown in FIG. 3, the electronic output S31 is conveyed from the audio processor 3010 to the audible output device 3956 via an electronic path 3001 devoid of an amplifier. Similarly stated, no amplifiers and/or drivers external to the audio processor 3010 are used to boost or increase the electronic output S31. The electronic path 3001 can be defined by any suitable electronic components. For example, in some embodiments, the electronic circuit system 3900 can have the audio processor 3010, the audible output device 3956, and/or the electronic path 3001 disposed on one or more printed circuit boards (PCBs), Such an arrangement can reduce the cost and/or complexity of the electronic circuit system 3900. Moreover, by excluding external amplifiers and/or drivers, the power required to produce the audible output OP31 can be relatively low, as discussed in more detail herein.

The audible output device 3956, which can be, for example, a microspeaker, is configured to produce the audible output OP31 in response to the electronic output S31. In this manner, the electronic circuit system 3900 and the audible output device 3956 can produce an audible output associated with the use of the medicament delivery device 3000, as discussed above.

Figure 4A:
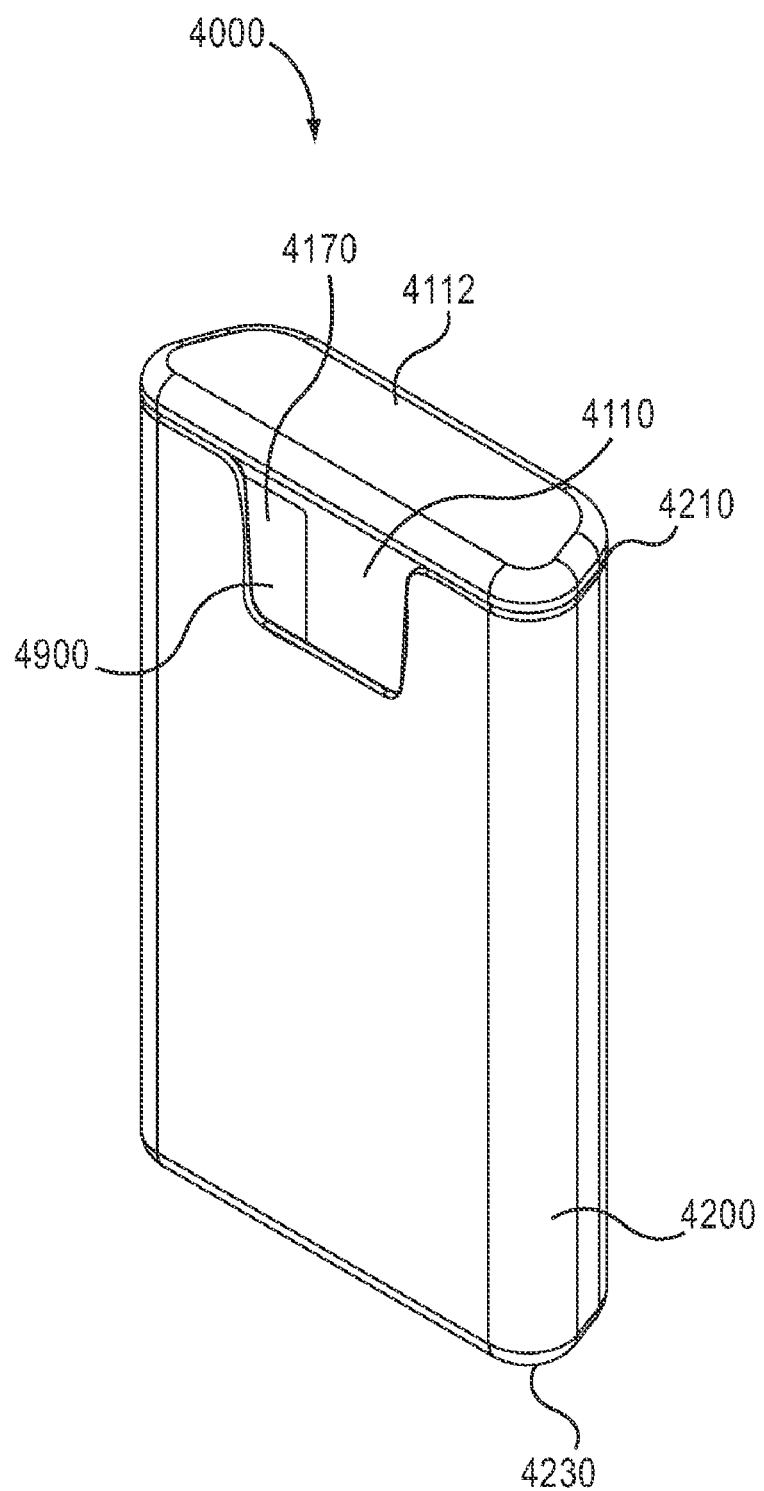
FIGS. 4A and 4B are perspective views of a medicament delivery device according to an embodiment of the invention, in a first configuration.
Figure 4B:
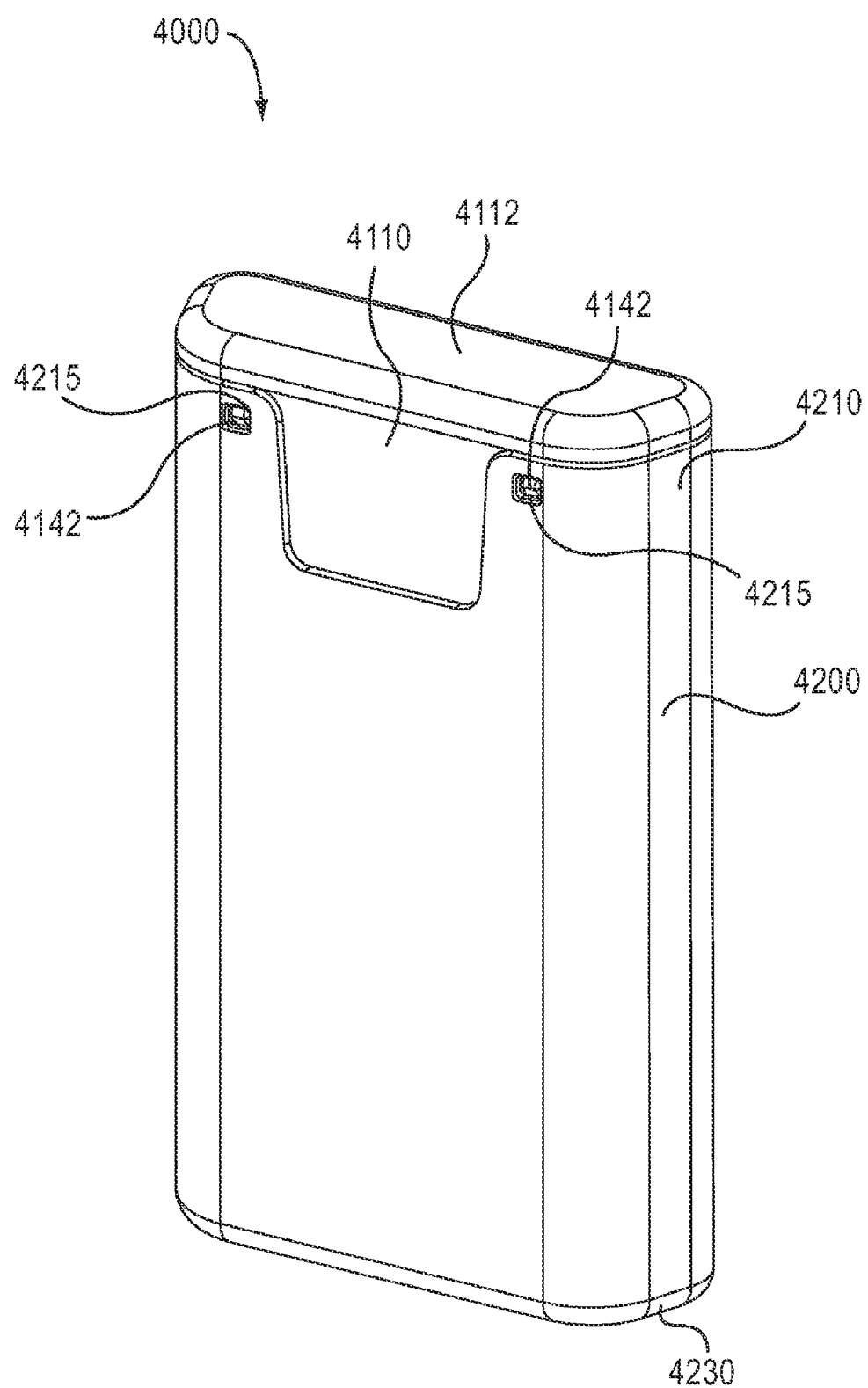
Figure 5:
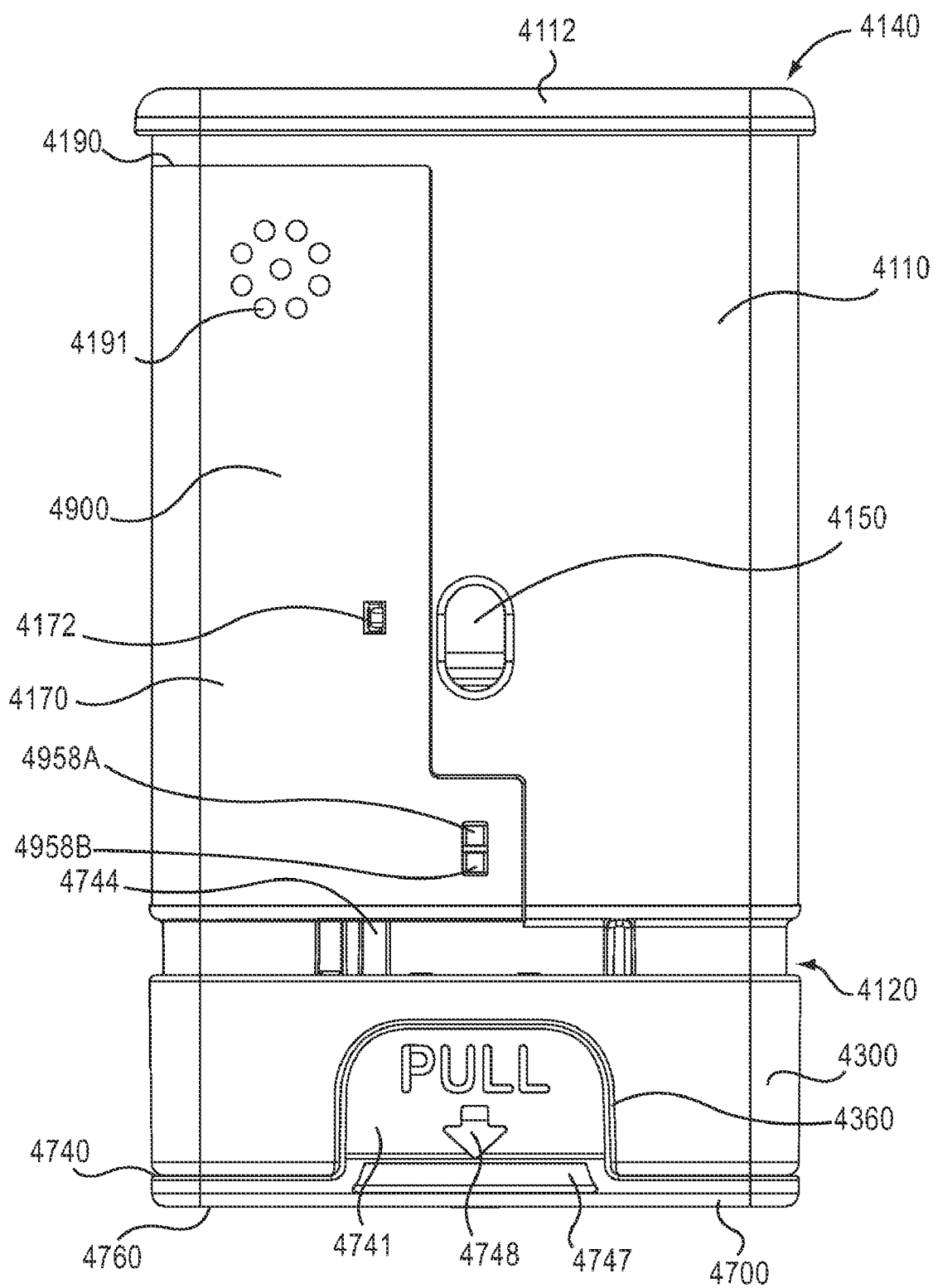
FIG. 5 is a front view of the medicament delivery device illustrated in FIGS. 4A and 4B with the cover removed.

FIGS. 4A-29 show a medicament delivery device 4000, according to an embodiment of the invention. FIGS. 4A-4B are perspective views of the medicament delivery device 4000 in a first configuration (i.e., prior to use). The medicament delivery device 4000 is similar to the medical injectors described in U.S. patent application Ser. No. 12/119,016, entitled "Medicament Delivery Device Having an Electronic Circuit System," filed May 12, 2008, which is incorporated herein by reference in its entirety. The medicament delivery device 4000 includes a housing 4110, a medicament delivery mechanism 4500 (see e.g., FIG. 12), an electronic circuit system 4900 (see e.g., FIGS. 13-21), a cover 4200 (see e.g., FIGS. 22-23), a safety lock 4700 (see e.g., FIGS. 24-25) and a base 4300 (see e.g., FIG. 26). A discussion of the components of the medicament delivery device 4000 will be followed by a discussion of the operation of the medicament delivery device 4000. In the embodiments described with respect to FIGS. 4A-29, the medicament delivery device 4000 is a medical injector.

As shown in FIGS. 5-11, the housing 4110 has a proximal end portion 4140 and a distal end portion 4120. The housing 4110 defines a first status indicator aperture 4150 and a second status indicator aperture 4151. The status indicator apertures 4150, 4151 can allow a patient to monitor the status and/or contents of a medicament container 4560. For example, by visually inspecting the status indicator apertures 4150, 4151, a patient can determine whether the medicament container 4560 contains a medicament and/or whether a medicament has been dispensed.

Figure 9:
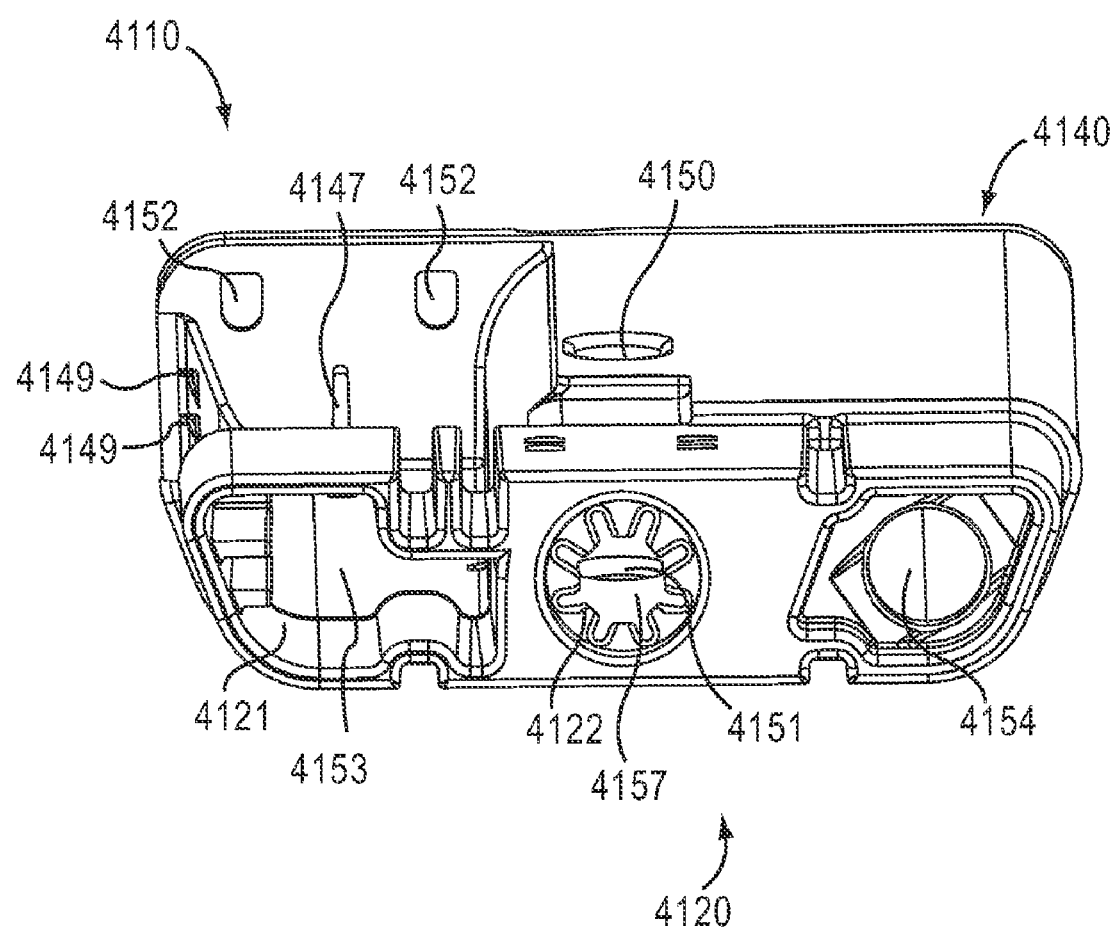
FIG. 9 is a bottom perspective view of a housing of the medicament delivery device illustrated in FIGS. 4A and 4B.
Figure 10:
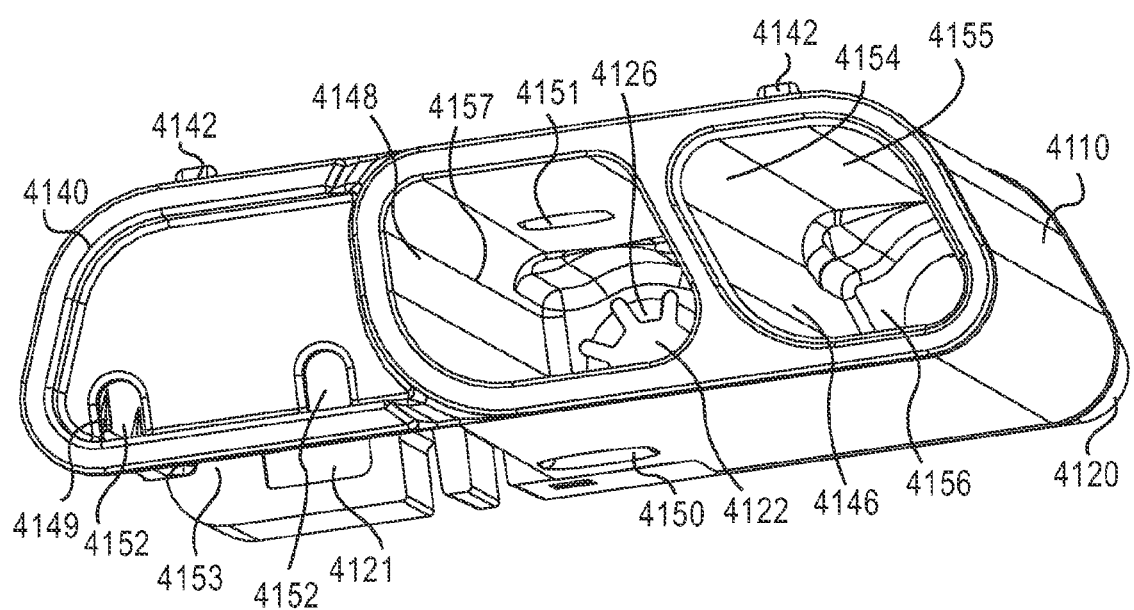
FIG. 10 is a top perspective view of a housing of the medicament delivery device illustrated in FIGS. 4A and 4B.

As shown in FIGS. 9 and 10, the housing 4110 defines a gas cavity 4154, a medicament cavity 4157, and an electronic circuit system cavity 4153. The gas cavity 4154 has a proximal end portion 4155 and a distal end portion 4156. The gas cavity 4154 is configured to receive the gas container 4570 and the release member 4540 of the medicament delivery mechanism 4500 (see e.g., FIG. 12), as described in further detail herein. The proximal end portion 4155 of the gas cavity 4154 is configured to receive the gas container retention member 4580 of the proximal cap 4112 of the housing 4110, as described in further detail herein. The gas cavity 4154 is in fluid communication with the medicament cavity 4157 via a gas passageway 4144 (see e.g., FIG. 11), as described in further detail herein.

The medicament cavity 4157 is configured to receive a portion of the medicament delivery mechanism 4500. In particular, the carrier 4520, the moveable member 4530 and the needle 4512 of the medicament delivery mechanism 4500 are movably disposed in the medicament cavity 4157. The medicament cavity 4157 is in fluid communication with a region outside the housing 4110 via a needle aperture 4122.

The electronic circuit system cavity 4153 is configured to receive the electronic circuit system 4900. The electronic circuit system cavity 4153 is isolated from the gas cavity 4154 and/or the medicament cavity 4157 via a side wall 4148 (see e.g., FIG. 10). Said another way, the electronic circuit system cavity 4153 is acoustically separated from and/or fluidically isolated from the gas cavity 4154 and/or the medicament cavity 4157. As described in more detail herein, the electronic circuit system cavity 4153 can function as an acoustic enclosure to enhance the magnitude and/or quality of the audible output produced by the electronic circuit system 4900.

The housing 4110 has protrusions 4149 (see e.g., FIG. 8) configured to stabilize the electronic circuit system 4900 when the electronic circuit system 4900 is disposed within the electronic circuit system cavity 4153. The housing 4110 also defines connection apertures 4152 configured to receive connection protrusions 4171A and 4171B (see e.g., FIG. 13) of the electronic circuit system 4900, and aperture 4145 (see e.g., FIG. 6) configured to receive a portion of a protrusion 4174 of the electronic circuit system 4900. In this manner, the electronic circuit system 4900 can be coupled to the housing 4110 within the electronic circuit system cavity 4153. In other embodiments, the electronic circuit system 4900 can be coupled within the electronic circuit system cavity 4153 by other suitable means such as an adhesive, a clip and/or the like.

Figure 6:
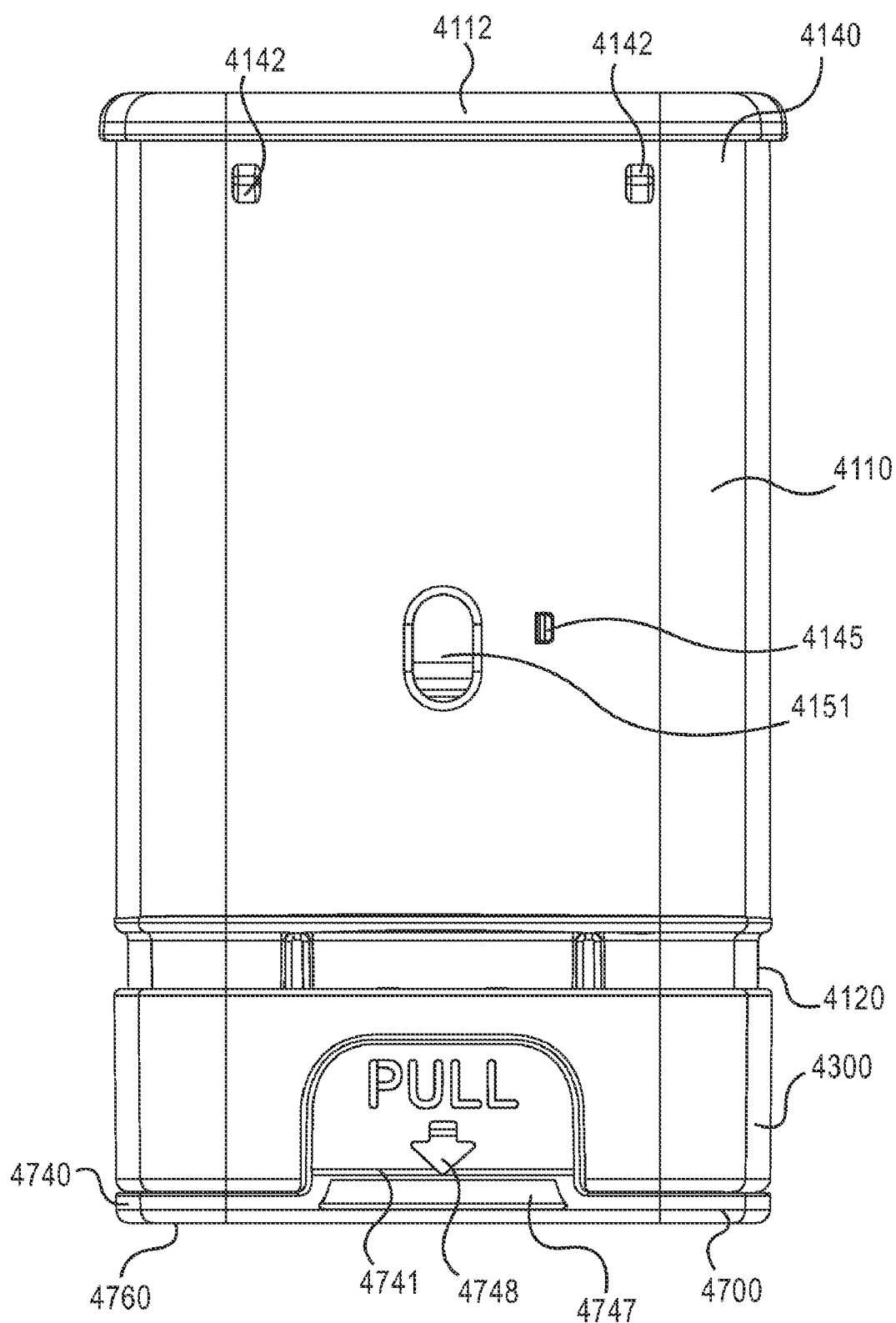
FIG. 6 is a back view of the medicament delivery device illustrated in FIGS. 4A and 4B with the cover removed.

The proximal end portion 4140 of the housing 4110 includes a proximal cap 4112, a speaker protrusion 4147 (see e.g., FIGS. 8 and 9), and cover retention protrusions 4142 (see e.g., FIGS. 4B and 6). The speaker protrusion 4147 is configured to maintain a position of an audible output device 4956 relative to the housing 4110 and/or an electronic circuit system cover 4170 when the electronic circuit system 4900 is attached to the housing 4110. As described in more detail below, in some embodiments, the speaker protrusion 4147 can press the front portion 4957 of the audible output device 4956 against the electronic circuit system cover 4170 to form a substantially airtight (e.g., a substantially hermetic) seal between the front portion 4957 of the audible output device 4956 and the electronic circuit system cover 4170. A substantially airtight seal can reduce undesirable audible noise that can result from air leaking through a gap between the front portion 4957 of the audible output device 4956 and the electronic circuit system cover 4170. Moreover, the speaker protrusion 4147 can reduce or minimize undesirable vibration of the audible output device 4956 by holding the audible output device 4956 in a substantially fixed position relative to the electronic circuit system cover 4170. The cover retention protrusions 4142 are configured to be received within corresponding openings 4215 on the cover 4200. In this manner, as described in more detail herein, the cover 4200 can be removably coupled to and disposed about at least a portion of the housing 4110.

Figure 11:
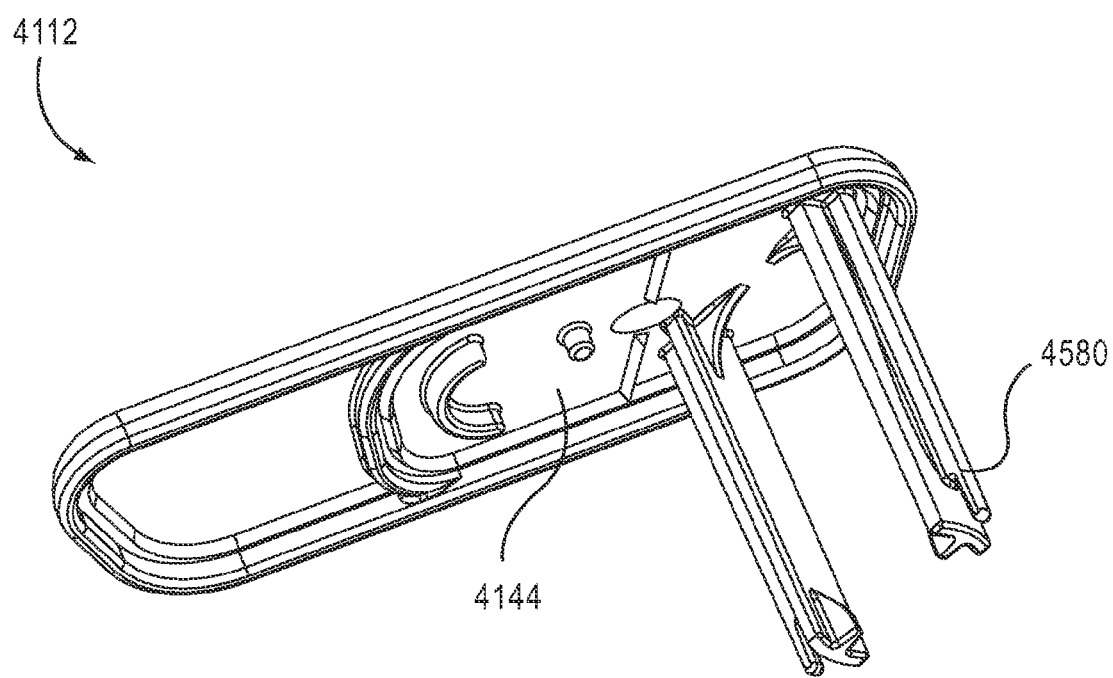
FIG. 11 is a perspective view of a proximal cap of the medicament delivery device illustrated in FIGS. 4A and 4B.

As shown in FIG. 11, the proximal cap 4112 includes a gas container retention member 4580 and defines a gas passageway 4144. The gas container retention member 4580 is configured to receive and/or retain a gas container 4570 that can contain a pressurized gas. The gas passageway 4144 is configured to allow for the passage of gas contained in the gas container 4570 from the gas cavity 4154 to the medicament cavity 4157, as further described herein. Said another way, the gas passageway 4144 places the gas cavity 4154 in fluid communication with the medicament cavity 4157.

Figure 7:
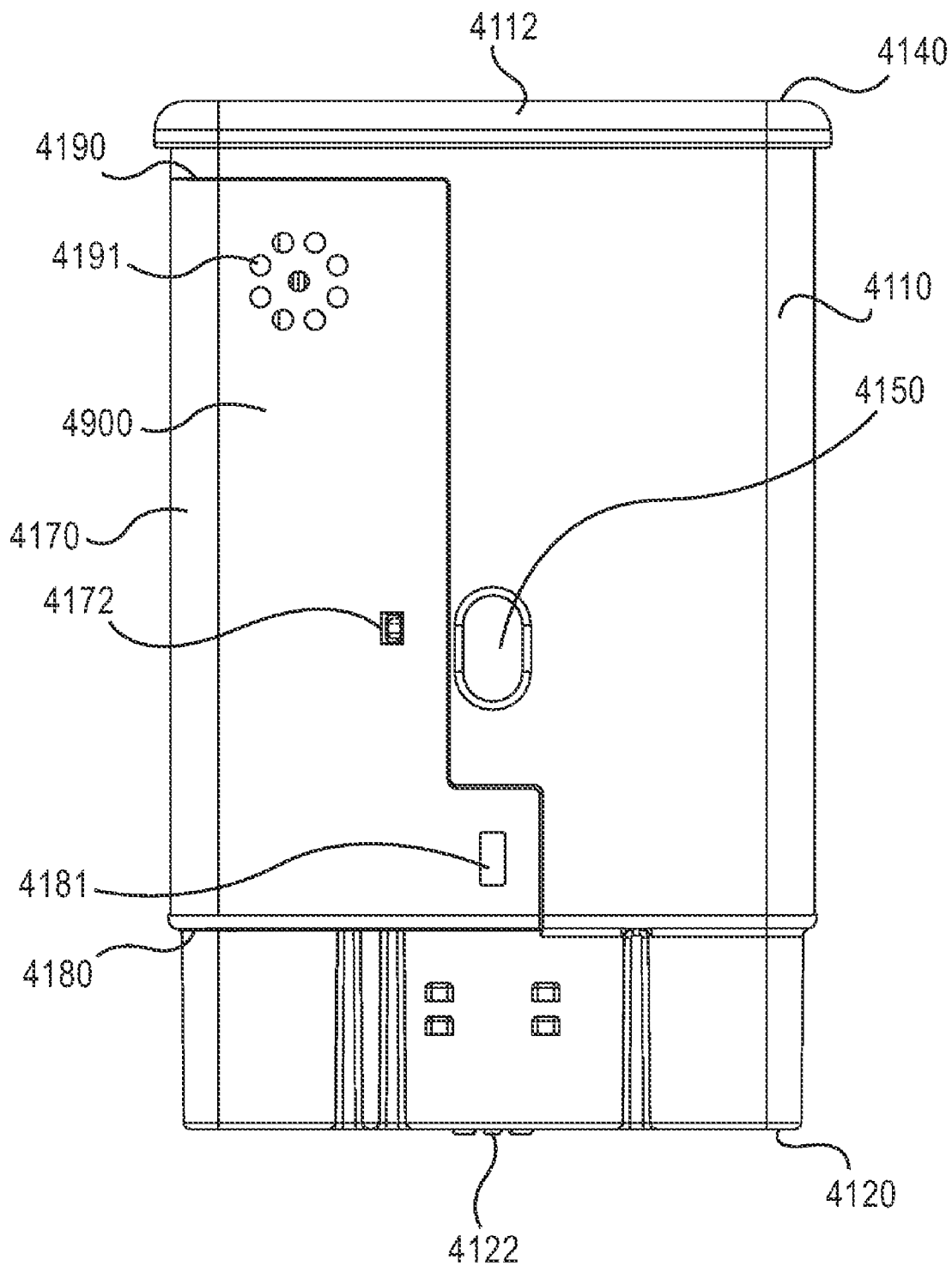
FIG. 7 is a front view of a portion of the medicament delivery device illustrated in FIGS. 4A and 4B.
Figure 8:
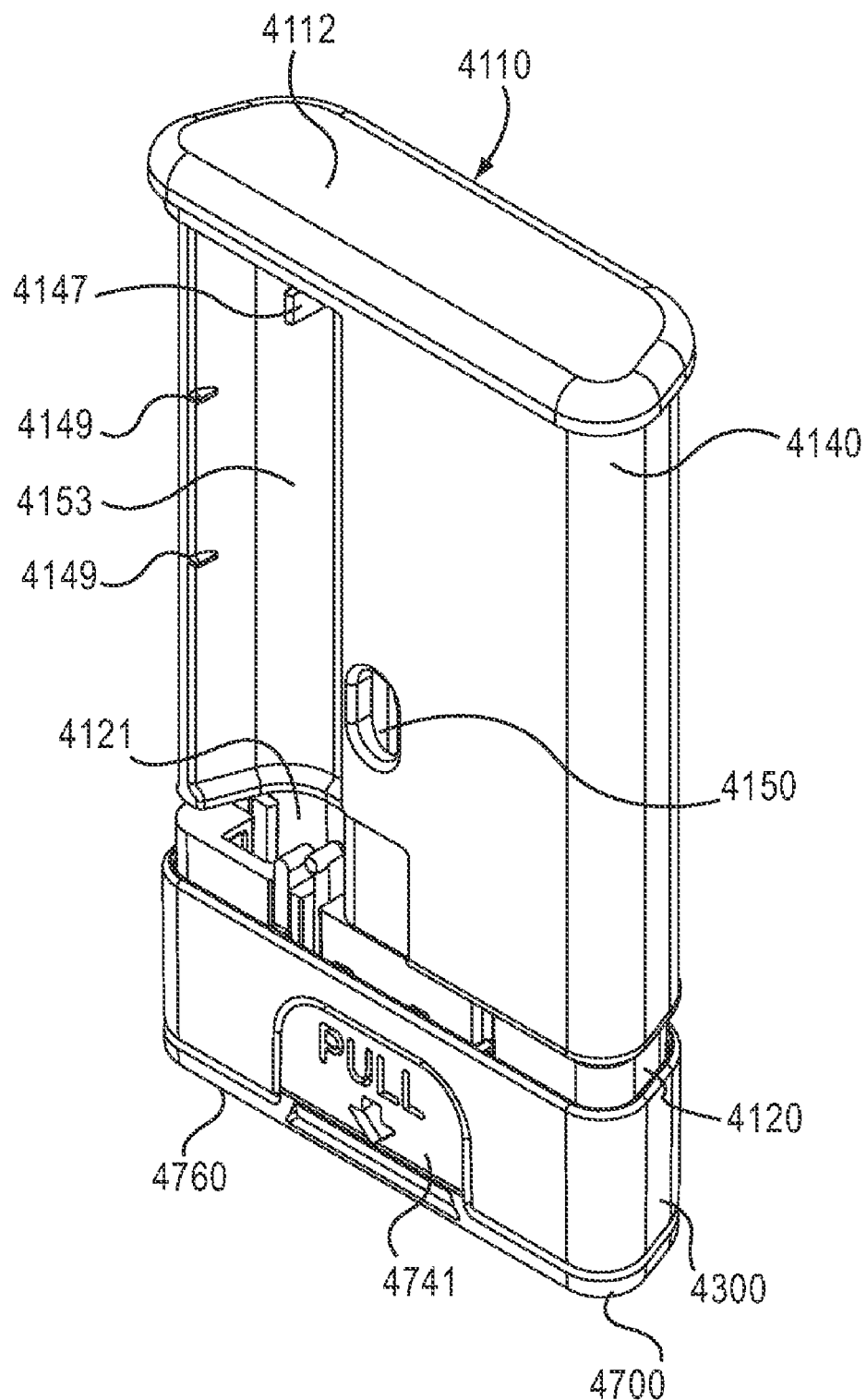
FIG. 8 is a perspective view of a portion of the medicament delivery device illustrated in FIGS. 4A and 4B.

As shown in FIGS. 7 and 9, the distal end portion 4120 of the housing 4110 defines a battery isolation protrusion aperture 4121 and a needle aperture 4122. The base 4300 is moveably coupled to the distal end portion 4120 of the housing 4110. The needle aperture 4122 is configured to allow the needle 4512 (see e.g., FIG. 12) to exit the housing 4110 when the medicament delivery device 4000 is actuated. The battery isolation protrusion aperture 4121 is configured to receive the battery isolation protrusion 4235 of the cover 4200 (see e.g., FIG. 23) when the cover 4200 is disposed about the housing 4110, as described in further detail herein. When the cover 4200 is moved relative to the housing 4100 to enable the medicament delivery device 4000 (see e.g., FIG. 27), the battery isolation protrusion aperture 4121 places the electronic circuit system cavity 4153 in fluid communication with a region outside of the housing 4110. Said another way, when the cover 4200 is moved relative to the housing 4100, the battery isolation protrusion aperture 4121 defines an opening through which sound waves produced by a back portion 4955 of the audible output device 4956 can exit the housing 4110.

Figure 12:
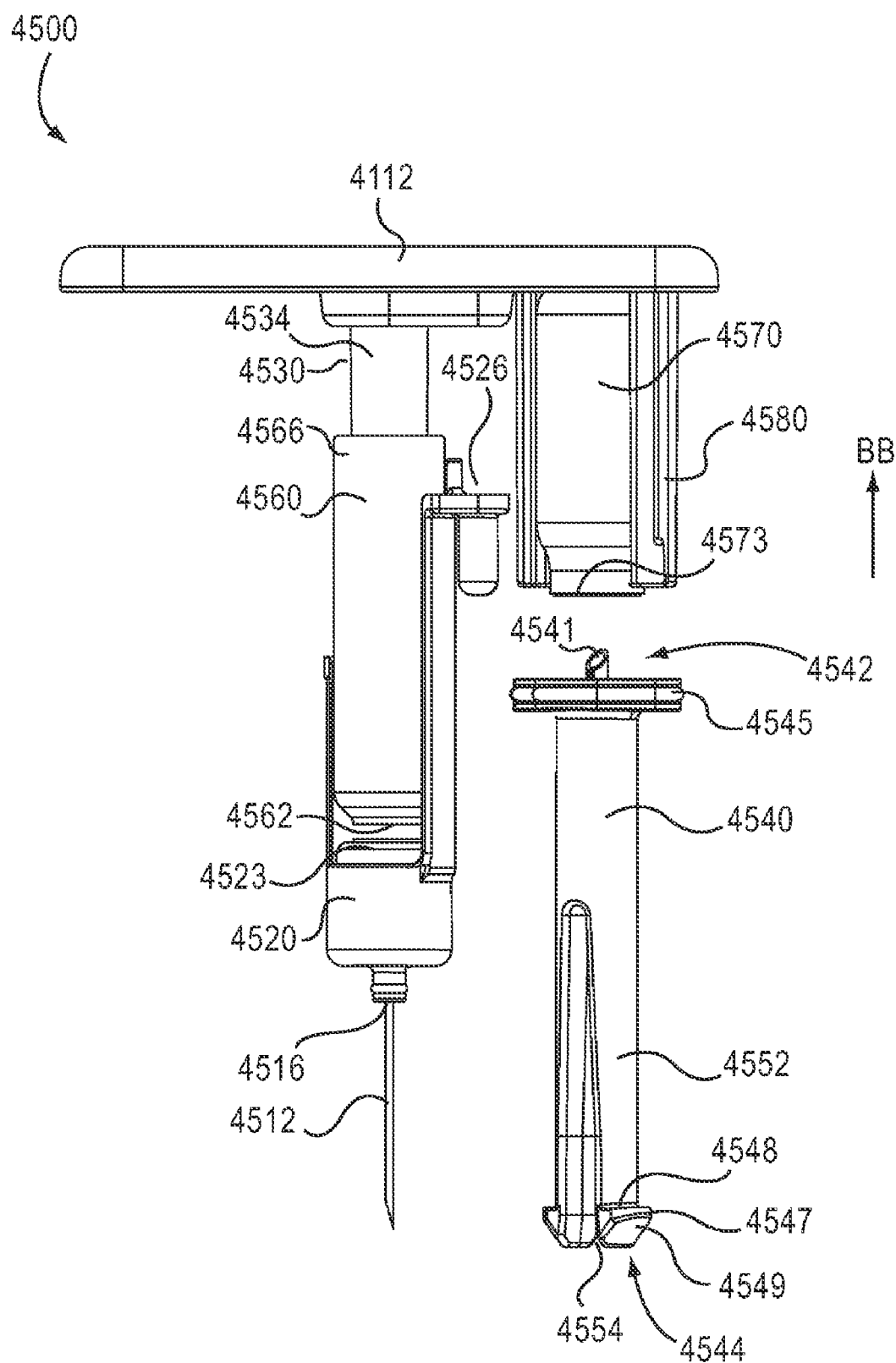
FIG. 12 is a front view of a medicament delivery mechanism of the medicament delivery device illustrated in FIGS. 4A and 4B.

FIG. 12 shows the medicament delivery mechanism 4500 of the medicament delivery device 4000. The medicament delivery device 4000 is similar to the auto-injectors described in U.S. Patent Application Publication Number 2007/0149925, entitled "Devices, Systems and Methods for Medicament Delivery," filed Nov. 21, 2006, which is incorporated herein by reference in its entirety. Accordingly, only an overview of the medicament delivery mechanism 4500 and related operation of the medicament delivery device 4000 is included below.

The medicament delivery mechanism 4500 includes a needle 4512, a carrier 4520, a movable member 4530, a medicament container 4560, a gas container 4570, and a release member 4540. As described above, the needle 4512, carrier 4520, movable member 4530 and medicament container 4560 are disposed within the medicament cavity 4157 of the housing 4110. The gas container 4570 and the release member 4540 are disposed within the gas cavity 4154 of the housing 4110.

The release member 4540 is movably disposed within the distal end portion 4156 of the gas cavity 4154. A proximal end portion 4542 of the release member 4540 includes a sealing member 4545 and a puncturer 4541. The sealing member 4545 is configured to engage the sidewall of the housing 4110 defining the gas cavity 4154 such that the proximal end portion 4155 of the gas cavity 4154 is fluidically isolated from the distal end portion 4156 of the gas cavity 4154. In this manner, when gas is released from the gas container 4570, the gas contained in the proximal end portion 4155 of the gas cavity 4154 is unable to enter the distal end portion 4156 of the gas cavity 4154. The puncturer 4541 is configured to contact and puncture a frangible seal 4573 on the gas container 4570 when the release member 4540 moves proximally within the gas cavity 4154, as shown by the arrow BB in FIG. 12.

A distal end portion 4544 of the release member 4540 includes extensions 4552. The extensions 4552 include projections 4547 that include tapered surfaces 4549 and engagement surfaces 4548. Further, the extensions 4552 define an opening 4554 between the extensions 4552. The engagement surfaces 4548 of the projections 4547 are configured to extend through the safety lock aperture 4128 of the housing 4110 and contact a distal surface of the housing 4110. In this manner, the engagement surfaces 4548 of the projections 4547 limit proximal movement of the release member 4540 when the engagement surfaces 4548 are in contact with the distal surface of the housing 4110. The tapered surfaces 4549 of the projections 4547 are configured to contact protrusions 4313 on a proximal surface 4310 of the base 4300 (see e.g., FIG. 26). In this manner, proximal movement of the base 4300 causes the extensions 4552 to move together, thereby releasing the engagement surfaces 4548 from the housing 4110 and allowing the release member 4540 to move proximally within the gas cavity 4154.

Figure 24:
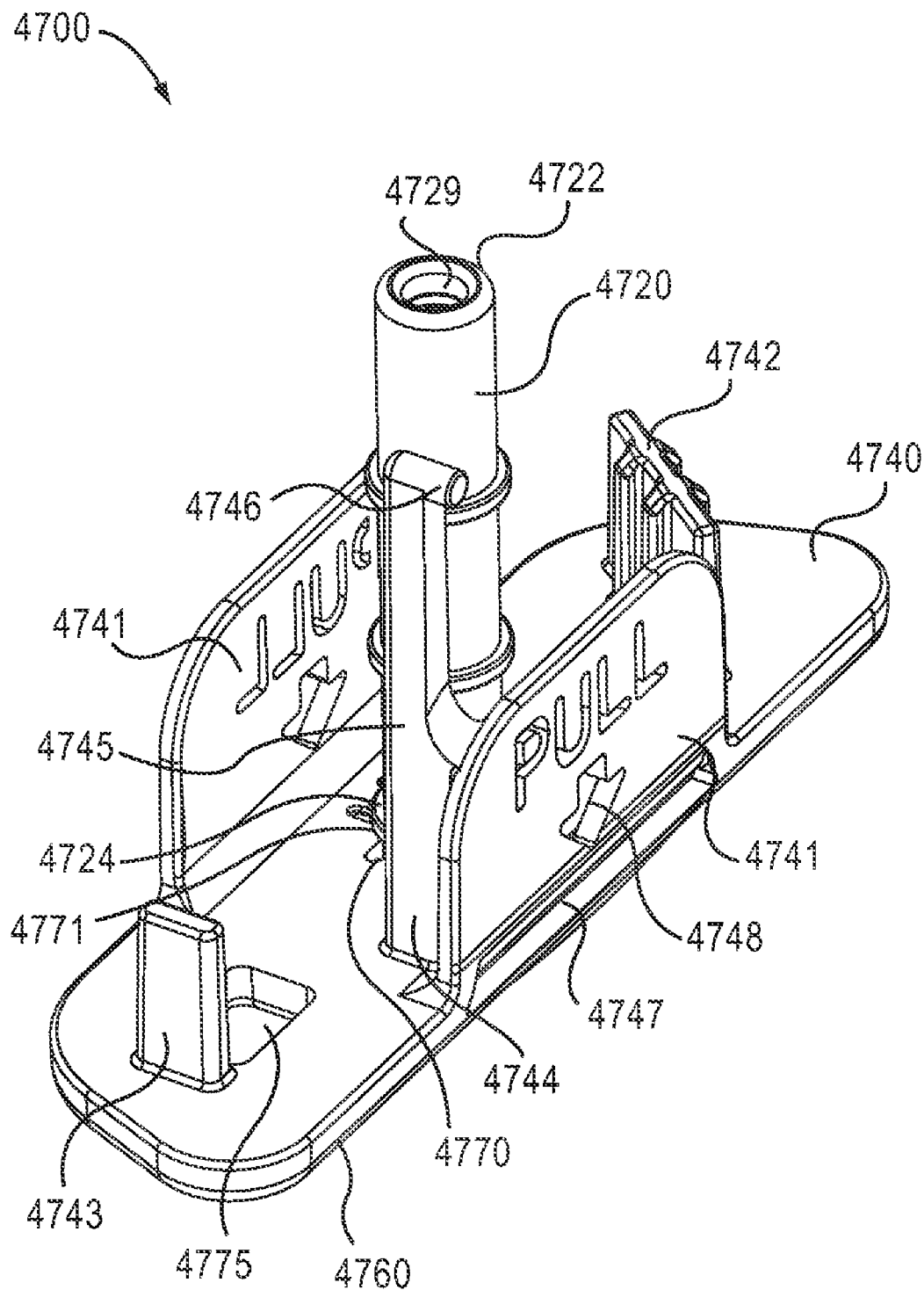
FIG. 24 is a perspective view of a safety lock of the medicament delivery device illustrated in FIGS. 4A and 4B.

The opening 4554 defined by the extensions 4552 is configured to receive the safety lock protrusion 4742 of the safety lock 4700 (see e.g., FIG. 24). The safety lock protrusion 4742 is configured to ensure that the extensions 4552 remain apart and the engagement surfaces 4548 of the projections 4547 remain in contact with the distal end portion 4120 of the housing 4110. In some embodiments, for example, the release member 4540 and/or the extensions 4552 can be constructed from any suitable material configured to withstand deformation that may occur when exposed to a load over an extended period of time.

The gas container 4570 is configured to contain a pressurized gas, and has a frangible seal 4573 at the distal end thereof. The frangible seal 4573 is configured to break when the puncturer 4541 of the proximal end portion 4542 of the release member 4540 contacts the frangible seal 4573. The gas container retention member 4580 of the proximal cap 4112 of the housing 4110 is configured to receive and/or retain the proximal end portion 4576 of the gas container 4570 to maintain the position of the gas container 4570. The medicament container 4560 of the medicament delivery mechanism 4500 is configured to contain a medicament. A distal end portion 4562 of the medicament container 4560 contains a seal 4523 configured to burst when punctured by a proximal end 4516 of the needle 4512, as described below. A proximal end portion 4566 of the medicament container 4560 is configured to receive a piston portion 4534 of the movable member 4530.

The movable member 4530 of the medicament delivery mechanism 4500 is movably disposed within the medicament cavity 4157. The movable member 4530 includes the piston portion 4534 having a plunger (not shown) at the distal end portion of the piston portion 4534. The piston portion 4534 is configured to move within the medicament container 4560. In this manner, the piston portion 4534 of the movable member 4530 can apply or exert pressure to a medicament contained in the medicament container 4560. The medicament contained in the medicament container can be, for example, epinephrine. The piston portion 4534 can be constructed of a resilient, durable, and/or sealing material, such as a rubber, for example.

Figure 22:
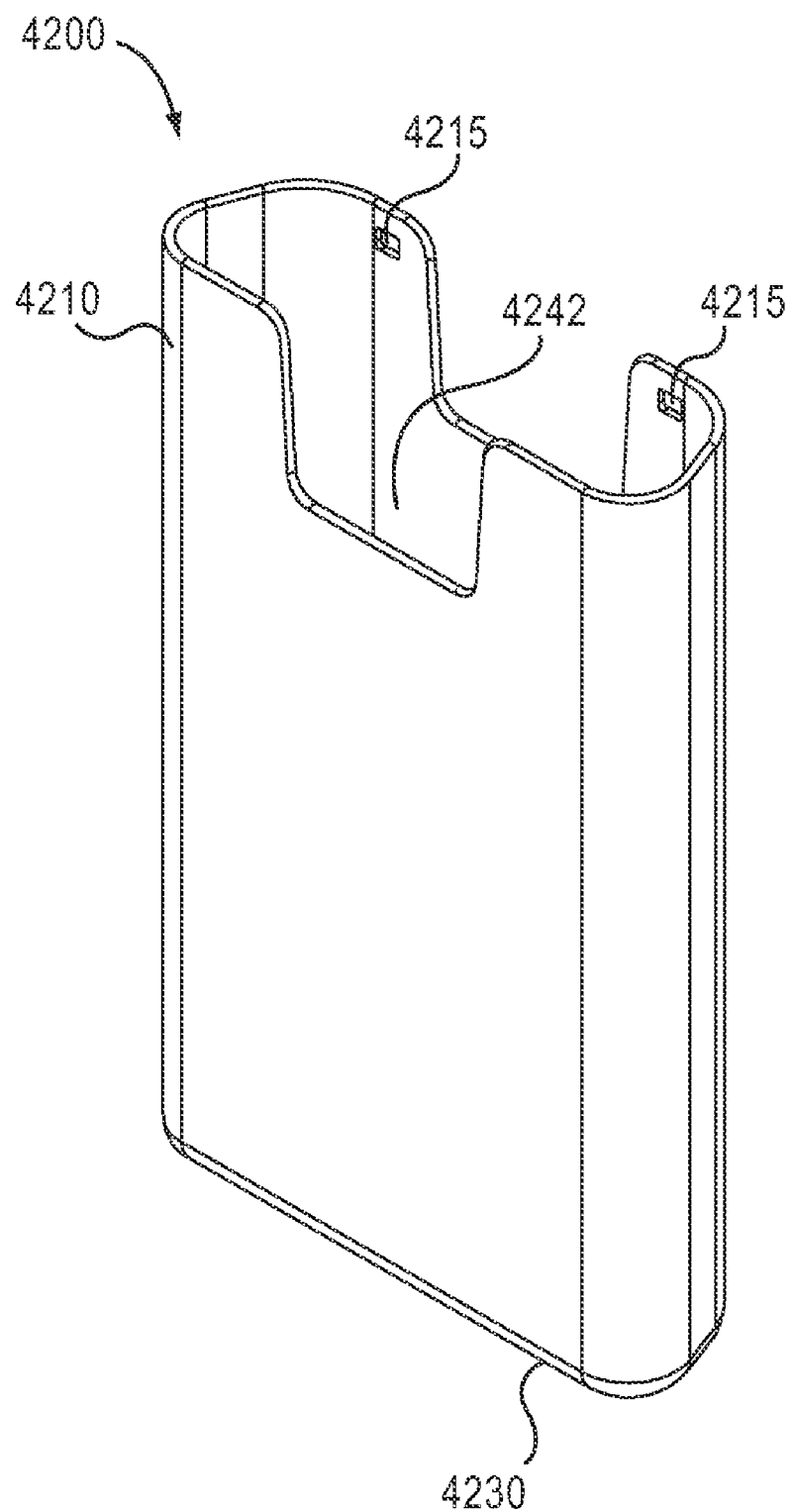
FIGS. 22 and 23 are perspective views of a cover of the medicament delivery device illustrated in FIGS. 4A and 4B.

FIGS. 13-20 show the electronic circuit system 4900. The electronic circuit system is configured to produce and/or output an audible output associated with a use of the medicament delivery device 4000. The electronic circuit system 4900 of the medicament delivery device 4000 includes the electronic circuit system cover 4170 shown and described above with reference to FIG. 7, a printed circuit board 4922, a processor 4950, a battery assembly 4962, an audible output device 4956, two light emitting diodes (LEDs) 4958A and 4958B, and a battery clip 4910. As shown in FIG. 22, the electronic circuit system 4900 is configured to fit within the electronic circuit system cavity 4153 of the housing 4110. Accordingly, as described above, the electronic circuit system 4900 is physically, acoustically, and/or fluidically isolated from the medicament cavity 4157 and/or the gas cavity 4154.

The electronic components (e.g., the printed circuit board 4922, the battery assembly 4962, and the like) are mounted to the electronic circuit system cover 4170. The electronic circuit system cover 4170 includes a distal end portion 4180 and a proximal end portion 4190. The proximal end portion 4190 includes connection protrusions 4171A and a battery clip protrusion 4173. The connection protrusions 4171A extend from the proximal end portion 4190 of the electronic circuit system cover 4170, and are configured to be disposed within the connection apertures 4152 of the housing 4110, as described above. In this manner, the electronic circuit system 4900 can be coupled to the housing 4110 within the electronic circuit system cavity 4153. In other embodiments, the electronic circuit system 4900 can be coupled to the housing 4110 by other suitable means such as an adhesive, a clip and/or the like.

The proximal end portion 4190 of the electronic circuit system cover 4170 defines multiple sound apertures 4191. The audible output device 4956 is disposed against the proximal end portion 4190 of the electronic circuit system cover 4170 such that the front portion 4957 of the audible output device 4956 is disposed adjacent the sound apertures 4191. In this manner, sound waves from the audible output device 4956 can travel from the audible output device 4956 to a region outside of the housing 4110 via the sound apertures 4191. As described above, in some embodiments, a sealing material (e.g., a compressible adhesive foam, an elastomeric o-ring, or the like) can be disposed on an outer perimeter of the front portion 4957 of the audible output device 4956 such that when the audible output device 4956 is pressed against the electronic circuit system cover 4170 by the speaker protrusion 4147, a substantially airtight seal is formed between the front portion 4957 of the audible output device 4956 and the electronic circuit system cover 4170. In this manner, sound waves produced by the front portion 4957 of the audible output device 4956 are directed through the multiple sound apertures 4191 and not through a breach or gap between the audible output device 4956 and the electronic circuit system cover 4170. In some embodiments, for example, the sealing material is a compressible adhesive foam approximately ¾ millimeters in thickness that covers approximately 10 percent of the front portion 4957 of the audible output device 4956.

Figure 18:
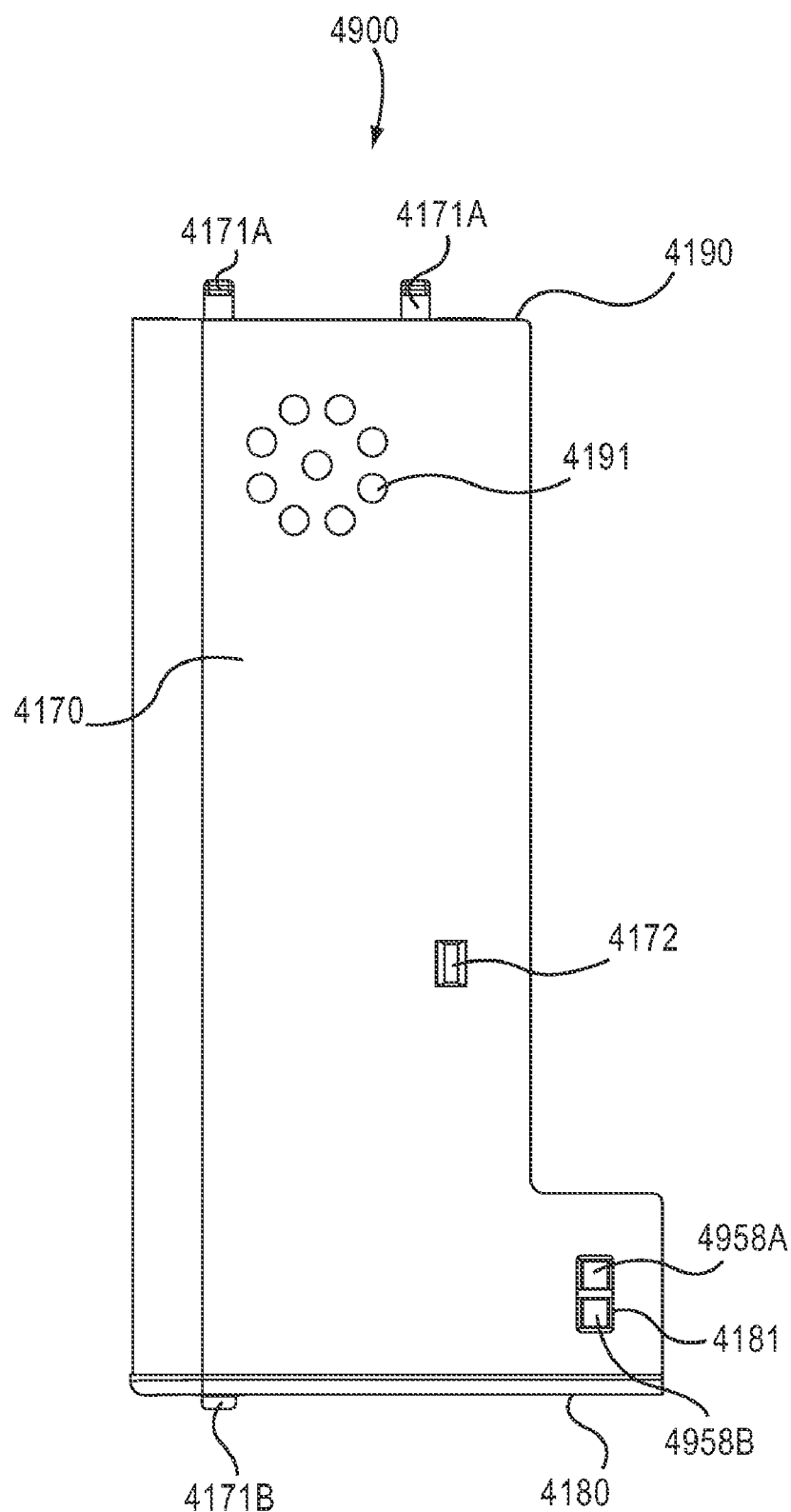
FIG. 18 is a front view of a cover of the electronic circuit system illustrated in FIG. 13.
Figure 19:
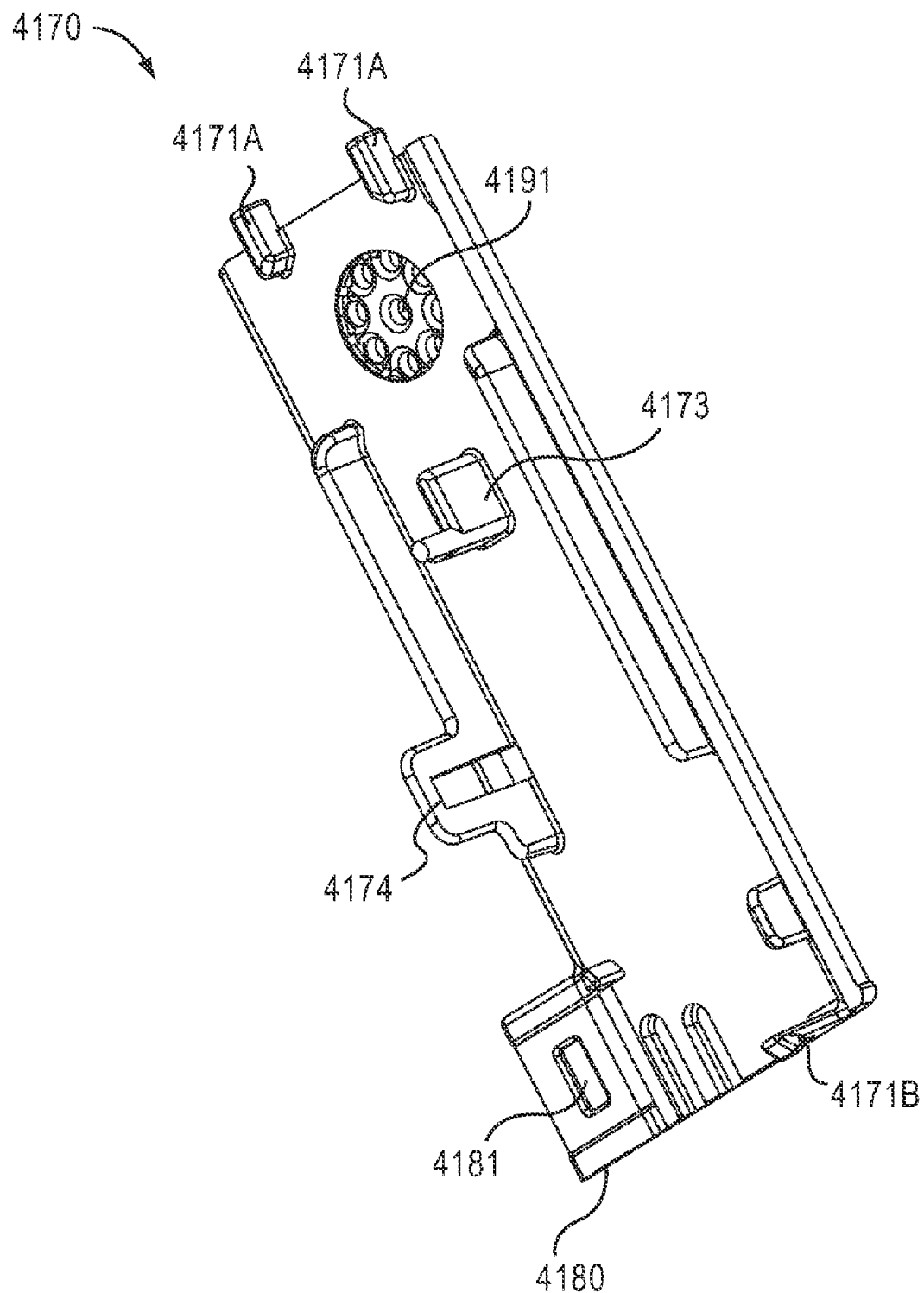
FIG. 19 is a perspective view of the cover of the electronic circuit system illustrated in FIG. 13.
Figure 20:
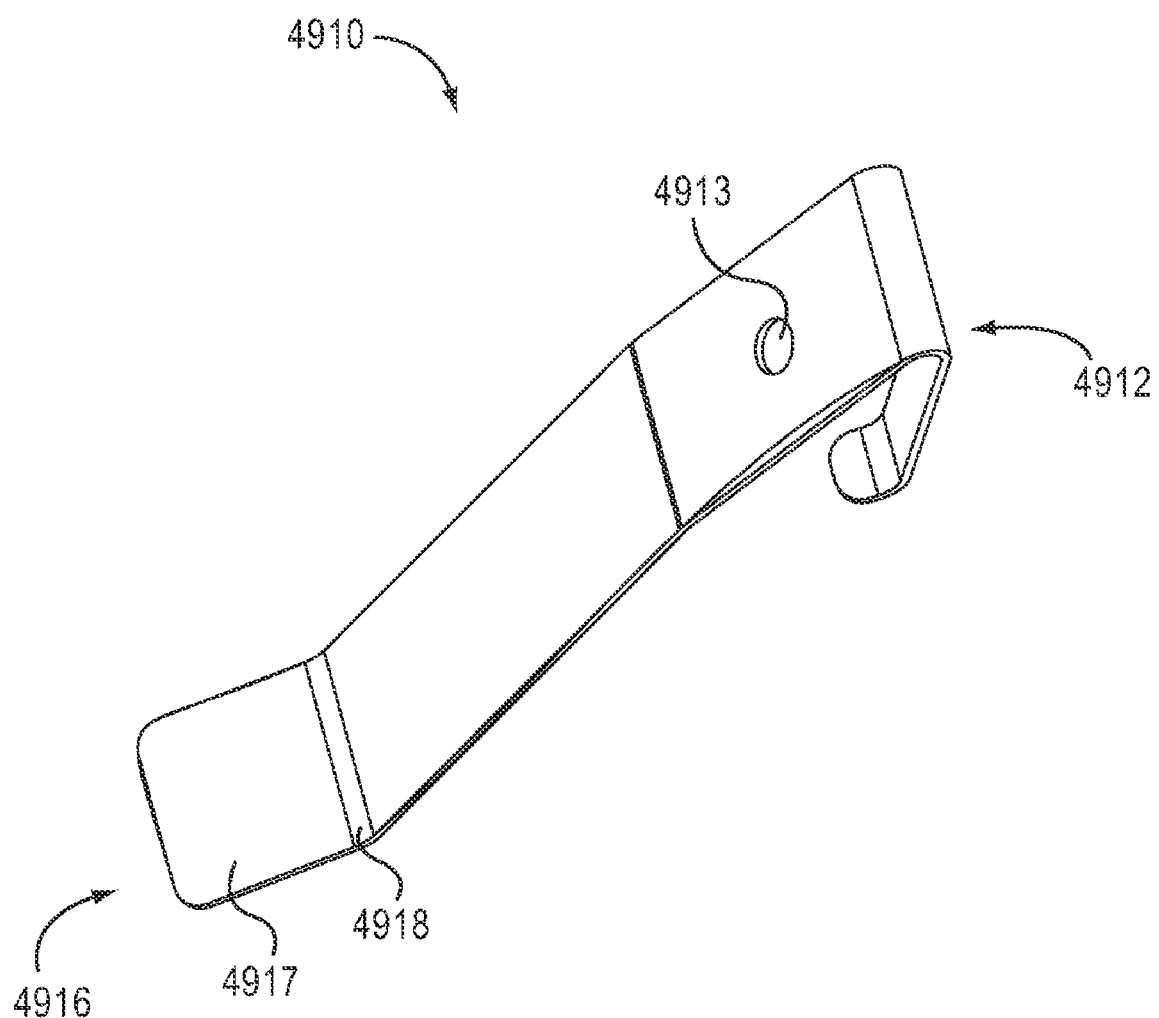
FIG. 20 is a perspective view of a battery clip of the electronic circuit system illustrated in FIG. 13.

As shown in FIGS. 18 and 19, the distal end portion 4180 of the electronic circuit system cover 4170 includes a connection protrusion 4171B, a stiffening protrusion 4174, and defines an LED aperture 4181 and an aperture 4172. The LED aperture 4181 is configured to receive the LEDs 4958A, 4958B such that a user can view the LEDs 4958A, 4958B, which are described in more detail herein. The connection protrusion 4171B extends from the distal end portion 4180 of the electronic circuit system cover 4170, and is configured to attach the electronic circuit system 4900 to the housing 4110, as described above. The stiffening protrusion 4174 is configured to have at least a portion received within and/or accessible via the aperture 4145 in the housing 4110 (see e.g., FIG. 6). The stiffening protrusion 4174 is configured to limit the bending (e.g., buckling) of the electronic circuit system cover 4170 when the electronic circuit system cover 4170 is coupled to the housing 4110.

The electronic circuit system cover 4170 is matingly coupled to the housing 4110 such that the electronic circuit system cover 4170 and the electronic circuit system cavity 4153 collectively define an acoustic enclosure within which the audible output device 4956 is disposed. Said another way, the electronic circuit system cover 4170 and the electronic circuit system cavity 4153 collectively form a region, volume and/or space that is configured to minimize or attenuate noise and/or enhance the audible output of the audible output device 4956. Moreover, the volume associated with the region defined by the electronic circuit system cover 4170 and the electronic circuit system cavity 4153 is larger than the volume of the audible output device 4956 and/or the electronic circuit system 4900 disposed within the region. In this manner, the acoustic enclosure defined by the electronic circuit system cover 4170 and the electronic circuit system cavity 4153 is configured to contain a volume of air behind the audible output device 4956.

Moreover, the audible output device 4956 and the electronic circuit system cavity 4153 are collectively configured to enhance the quality and/or magnitude of the sound produced by the audible output device 4956. For example, in some embodiments, the size and/or shape of the electronic circuit system cavity 4153 can be configured such that the electronic circuit system cavity 4153 defines an acoustic resonant frequency that is within a predefined frequency range of the audible output device 4956. More particularly, in some embodiments, the electronic circuit system cavity 4153 can be configured such that the electronic circuit system cavity 4153 defines an acoustic resonant frequency that is substantially the same as a resonant frequency of the audible output device 4956. In this manner, the quality and/or magnitude of the sound produced by the audible output device 4956 can be enhanced for a particular range of frequencies. In some embodiments, the quality and/or magnitude of the sound produced by the audible output device 4956 can be enhanced for a frequency range corresponding to the frequency range of a recorded speech output.

Figure 14:
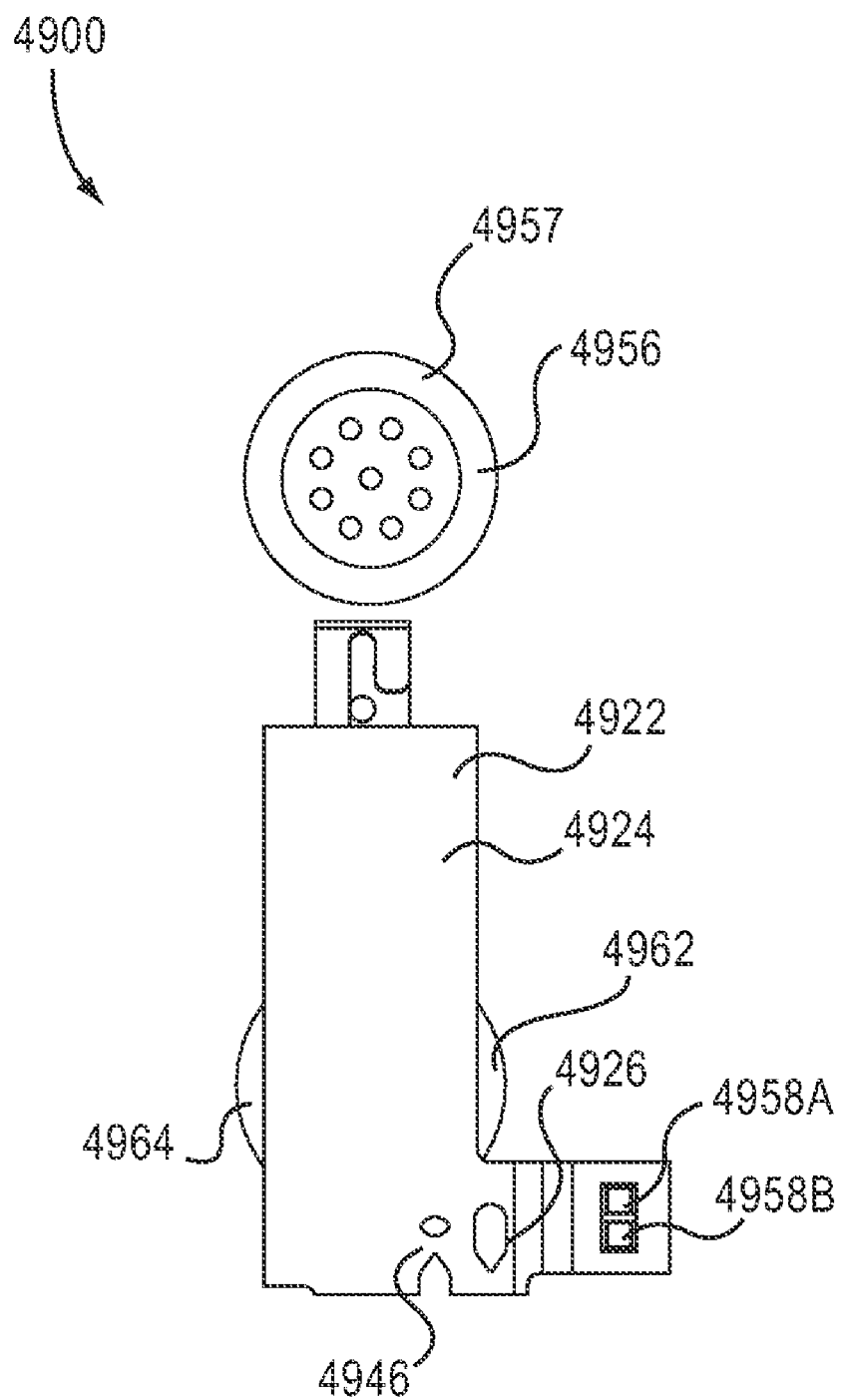
FIG. 14 is a front view of a portion of the electronic circuit system of the medicament delivery device illustrated in FIG. 13.
Figure 15:
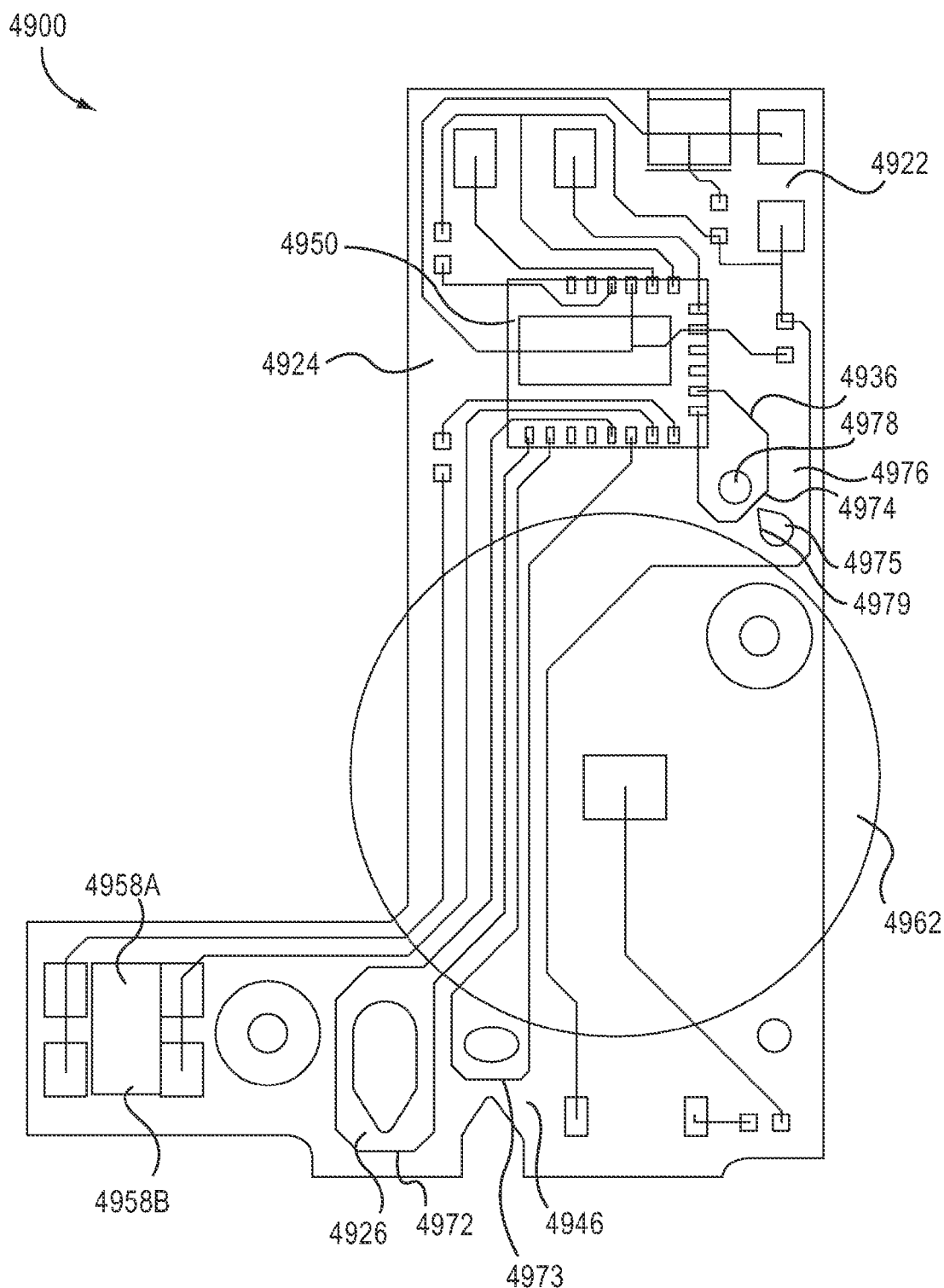
FIG. 15 is a back view of a printed circuit board of the electronic circuit system shown in FIG. 14.

As shown in FIGS. 14 and 15, the printed circuit board 4922 of the electronic circuit system 4900 includes a substrate 4924, a first actuation portion 4926 and a second actuation portion 4946. The printed circuit board 4922 provides the structure upon which at least a portion of the electronic components of the electronic circuit system 4900 are mounted. Moreover, the printed circuit board 4922 includes conductive portions (e.g., copper traces, insulated wires, flexible wires or the like) to electronically couple the components.

The processor 4950 is configured to process electronic inputs (e.g., from input switches) and produce electronic signals and/or outputs. As described herein, such electronic signals can include signals related to audio or visual outputs associated with a use of the medicament delivery device 4000. More particularly, the processor 4950 is configured to output an electronic signal to the audible output device 4956, which then converts the electronic signal into sound waves. Said another way, the processor 4950 is configured to output an electronic signal associated with an audible output to the audible output device 4956, which is configured to output the audible output. The electronic signal can be associated with, for example, recorded speech, a single tone, a sequence of tones, and/or the like. In this manner, the electronic circuit system 4900 can produce and/or output an audible output associated with a use of the medicament delivery device 4000.

Figure 16:
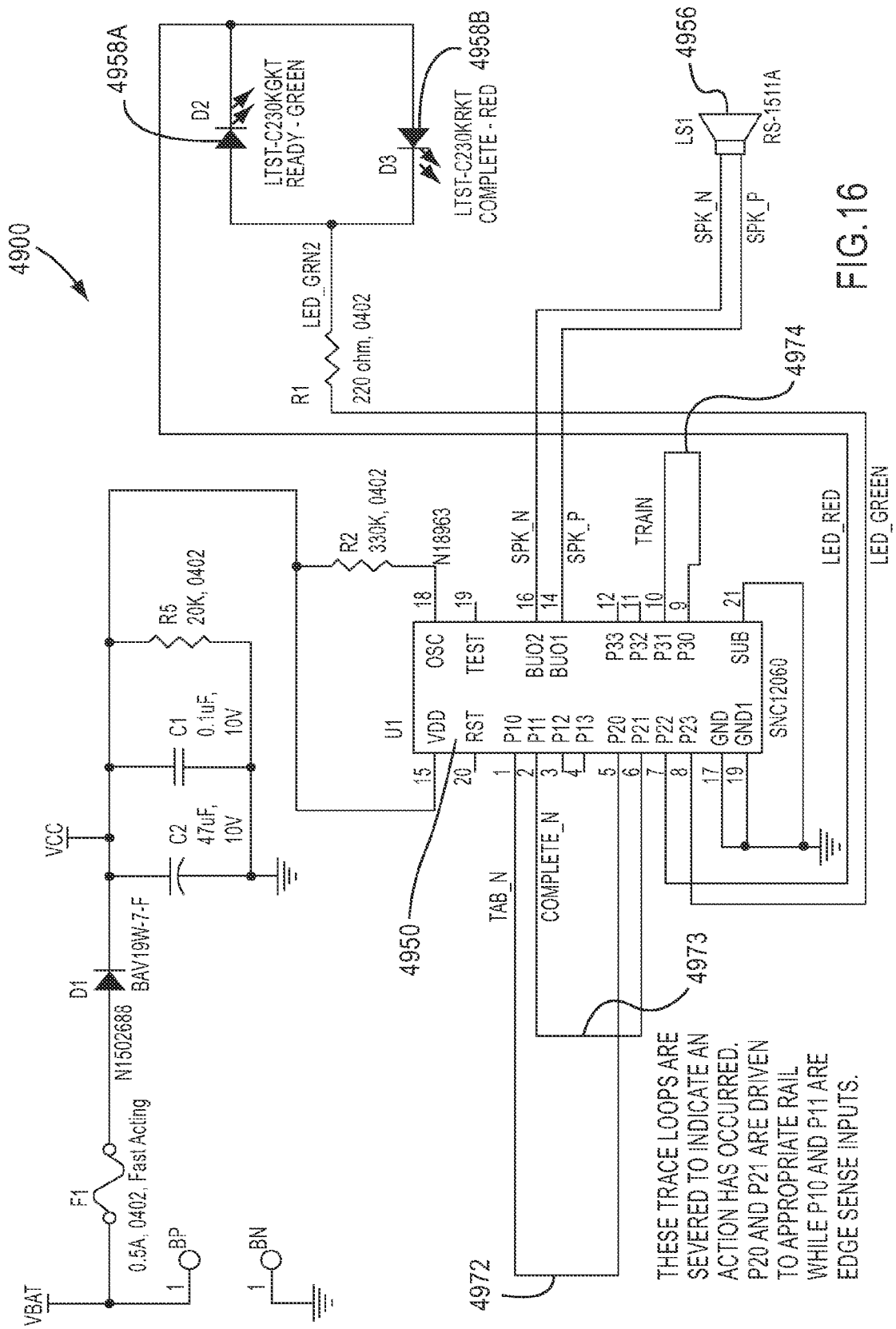
FIG. 16 is a schematic illustration of the electronic circuit system shown in FIG. 13.
Figure 17:
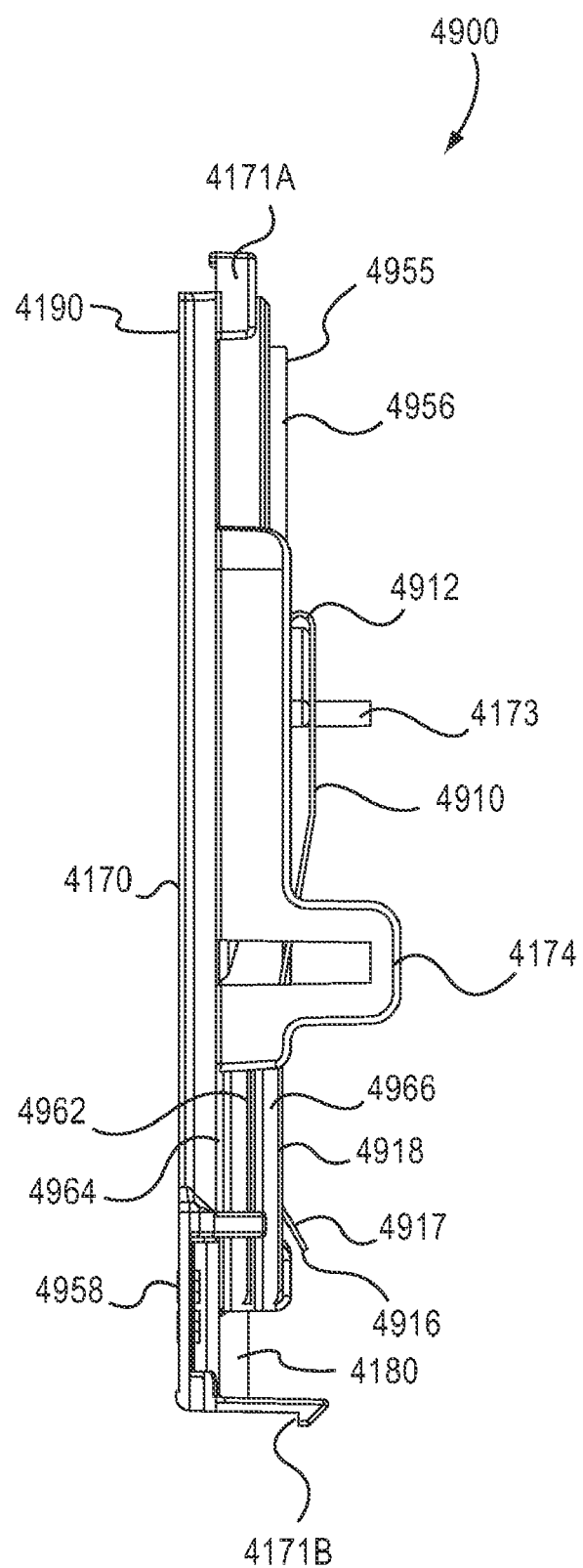
FIG. 17 is a side view of the electronic circuit system of the medicament delivery device illustrated in FIG. 13.

The electronic signals produced by the processor 4950 are conveyed to the audible output device 4956 via one or more electronic paths (not identified in FIG. 15) defined by the printed circuit board 4922 (e.g., conductive traces or the like). As shown in FIG. 16, the electronic paths between the processor 4950 and the audible output device 4956 are devoid of an amplifier. Similarly stated, no amplifiers and/or drivers external to the processor 4956 are used to amplify or increase the electronic signals produced by the processor 4950. This arrangement can reduce the cost and/or complexity of the electronic circuit system 4900. Moreover, by being devoid of external amplification, the power of the electronic signals conveyed to the audible output device 4956 can be relatively low. In this manner, the life of the battery assembly 4962 can be extended, the battery assembly 4962 can include smaller batteries and/or the battery assembly 4962 can include fewer batteries. In some embodiments, for example, the electronic signal produced by the processor 4950 can have a power of less than 500 milliwatts (mW). In other embodiments, the electronic signal produced by the processor 4950 can have a power of less than 100 milliwatts (mW). In yet other embodiments, the electronic signal produced by the processor 4950 can have a power of approximately 80 milliwatts (mW).

The processor 4950 can be a commercially-available processing device dedicated to performing one or more specific tasks. For example, in some embodiments, the processor 4950 can be a commercially-available microprocessor, such as the Sonix SNC 12060 voice synthesizer. Alternatively, the processor 4950 can be an application-specific integrated circuit (ASIC) or a combination of ASICs, which are designed to perform one or more specific functions. In yet other embodiments, the processor 4950 can be an analog or digital circuit, or a combination of multiple circuits. In some embodiments, the processor 4950 can be programmed through, for example, an internal controller (not shown) such that varied applications, including voice section combination, key trigger arrangement, and/or output control, for example, can be implemented.

The processor 4950 can include a memory device (not shown) configured to receive and store information, such as a series of instructions, processor-readable code, a digitized signal, or the like. For example, the memory device can store operating code, recorded speech or voice code, and/or data code. The memory device can include one or more types of memory. For example, the memory device can include a read only memory (ROM) component and a random access memory (RAM) component. The memory device can also include other types of memory suitable for storing data in a form retrievable by the processor 4950, for example, electronically-programmable read only memory (EPROM), erasable electronically-programmable read only memory (EEPROM), or flash memory. In some embodiments, a memory device separate from the processor 4950 can be used to receive and store information.

The battery assembly 4962 of the electronic circuit system 4900 includes two batteries stacked on top of one another. The batteries can be, for example, three volt, "watch-style" lithium batteries. The battery assembly 4962 has a first surface 4964 and a second surface 4966. The first surface 4964 of the battery assembly 4962 can contact an electrical contact (not shown) disposed on the substrate 4924. The second surface 4966 of the battery assembly 4962 is configured to contact a contact portion 4918 of a distal end portion 4916 of a battery clip 4910. When both the electrical contact of the substrate 4924 and the contact portion 4918 of the distal end portion 4916 of the battery clip 4910 contact the battery assembly 4962, the batteries of the battery assembly 4962 are placed in electrical communication with the electronic circuit system 4900. Said another way, when the electrical contact of the substrate 4924 and the contact portion 4918 of the distal end portion 4916 of the battery clip 4910 contact the battery assembly 4962, the battery assembly 4962 is configured to supply power to the electronic circuit system 4900.

The battery clip 4910 (shown in FIG. 20) includes a proximal end portion 4912 and a distal end portion 4916. The proximal end portion 4912 defines a retention aperture 4913. The retention aperture 4913 is configured to receive the battery clip protrusion 4173 of the electronic circuit system cover 4170. In this manner, the battery clip protrusion 4173 maintains the position of the battery clip 4910 with respect to the electronic circuit system cover 4170 and/or the battery assembly 4962.

The distal end portion 4916 of the battery clip 4910 includes a contact portion 4918 and an angled portion 4917. As described above, the contact portion 4918 is configured to contact the second surface 4916 of the battery assembly 4962 to place the battery assembly 4962 in electrical communication with the electronic circuit system 4900. The angled portion 4917 of the distal end portion 4916 of the battery clip 4910 is configured to allow a proximal end portion 4236 of a battery isolation protrusion 4235 (see e.g., FIG. 23) to be disposed between the second surface 4966 of the battery assembly 4962 and the contact portion 4918 of the distal end portion 4916 of the battery clip 4910. When the battery isolation protrusion 4235 is disposed between the second surface 4966 of the battery assembly 4962 and the contact portion 4918 of the distal end portion 4916 of the battery clip 4910, the electrical path between the battery assembly 4962 and the remainder of the electrical circuit system 4900 is severed, thereby removing power from the electronic circuit system 4900. The contact portion 4918 of the distal end portion 4916 of the battery clip 4910 is biased such that when the battery isolation protrusion 4235 is removed, the contact portion 4918 will move into contact the second surface 4916 of the battery assembly 4962, thereby restoring electrical communication between the battery assembly 4962 and the electronic circuit system 4900. In some embodiments, the battery isolation protrusion 4235 can be repeatedly removed from between the second surface 4966 of the battery assembly 4962 and the contact portion 4918 of the distal end portion 4916 of the battery clip 4910 and reinserted. Said another way, the battery isolation protrusion 4235 and the battery clip 4910 collectively form a reversible on/off switch.

When the battery isolation protrusion 4235 is disposed between the second surface 4966 of the battery assembly 4962 and the contact portion 4918 of the distal end portion 4916 of the battery clip 4910, a portion of the battery isolation protrusion 4235 is also disposed within the battery isolation protrusion aperture 4121. Conversely, when the battery isolation protrusion 4235 is removed from between the second surface 4966 of the battery assembly 4962 and the contact portion 4918 of the distal end portion 4916 of the battery clip 4910 the battery isolation protrusion aperture 4121 is opened. In this manner, the battery isolation protrusion 4235 can selectively open and/or close the battery isolation protrusion aperture 4121. In this regard, the battery isolation protrusion aperture 4121 can selectively function as a port to allow sound waves produced by the audible output device 4956 to exit the electronic circuit system cavity 4153 to an area outside the housing 4110. As described herein, in some embodiments, the location of the battery isolation protrusion aperture 4121 with respect to the location of the audible output device 4956 and/or the sound apertures 4191 is such that the sound waves that exit through the multiple sound apertures 4191 are substantially in phase with the sound waves that exit through the battery isolation protrusion aperture 4121.

The audible output device 4956 of the electronic circuit system 4900 is configured to output audible sound associated with a use of the medicament delivery device 4000. The audible output device 4956 can have any suitable performance characteristics to produce the desired audible output (e.g., an audible output having a predefined frequency range, a predefined sound pressure level, etc.) based on the electronic signals produced by the processor 4950, as described above. For example, the audible output device 4956 can have a specified resonance frequency, a specified output sound pressure level (e.g., Watts/meter), a specified maximum input power rating, and/or a specified frequency response range. The audible output device 4956 can have one or more resonant frequencies within the specified frequency response range. In some embodiments, the audible output device 4956 can be a commercially-available micro-speaker such as an M0015N07K01F micro-speaker manufactured by Dain (International) Co., Ltd. In other embodiments, the audible output device 4956 can be an RS-1511A micro-speaker manufactured by Regal Electronics, Inc., for example.

Figure 13:
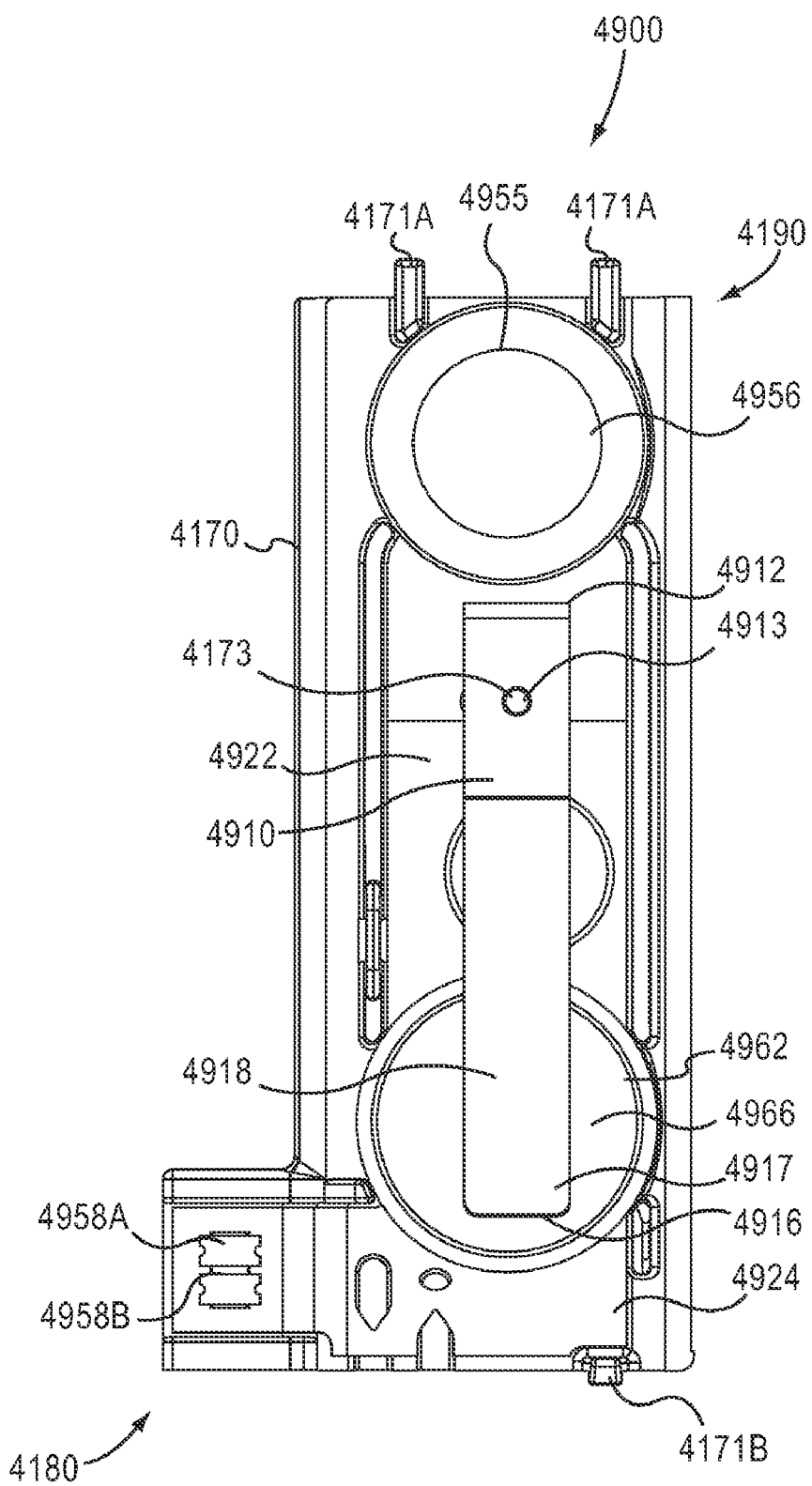
FIG. 13 is a back view of an electronic circuit system of the medicament delivery device illustrated in FIGS. 4A and 4B.

As shown in FIGS. 13 and 14, the audible output device 4956 includes a front portion 4957 and a back portion 4955. The audible output device 4956 can include a movable portion (e.g., a cone, membrane, diaphragm, or the like; not shown in FIGS. 13 and 14) such that the audible output device 4956 can produce a first set of sound waves from the front portion 4957 and a second set of sound waves from the back portion 4955. The sound waves produced by the front portion 4957 and the sound waves produced by the back portion 4955 collectively define the audible output of the audible output device 4956. More particularly, the audible output of the audible output device 4956 is characterized by the sound waves produced by the front portion 4957 and the sound waves produced by the back portion 4955 as they exit the electronic circuit system cavity 4153 through the sound apertures 4191 and the battery isolation protrusion aperture 4121, respectively.

As described above, the audible output device 4956 and the electronic circuit system cavity 4153 are collectively configured to enhance the quality and/or magnitude of the sound produced by the audible output device 4956. Similarly stated, the size, shape and/or number and location of openings (e.g., the sound apertures 4191 and the battery isolation protrusion aperture 4121) of the electronic circuit system cavity 4153 are configured to enhance the quality of the audible output produced by the audible output device 4956 having predefined performance characteristics. In some embodiments, for example, the electronic circuit system cavity 4153 and the electronic circuit system cover 4170 are configured such that the sound waves produced by the front portion 4957 as they exit through the sound apertures 4191 are substantially in phase with the sound waves produced by the back portion 4955 as they exit through the battery isolation protrusion aperture 4121. This can be accomplished, for example, by spacing the sound apertures 4191 apart from the battery isolation protrusion aperture 4121 by a predetermined distance. In this manner, the distance through which the sound waves produced by the front portion 4957 travel to exit through the sound apertures 4191 and the distance through which the sound waves produced by the back portion 4955 travel to exit through the battery isolation protrusion aperture 4121 can be set to predetermined values such that the sound waves produced by the front portion 4957 are substantially in phase with the sound waves produced by the back portion 4955 as they exit the sound apertures 4191 and the battery isolation protrusion aperture 4121, respectively. For example, in some embodiments, the sound apertures 4191 can be spaced apart from the battery isolation protrusion aperture 4121 by approximately 2.5 inches to 3 inches. In other embodiments, the sound apertures 4191 can be spaced apart from the battery isolation protrusion aperture 4121 by approximately 1 inch to 3 inches.

In some embodiments, the audible output device 4956 and the electronic circuit system cavity 4153 can be collectively "tuned" to enhance the quality of an audible output having a specific frequency range. For example, in some embodiments, the audible output device 4956 and the electronic circuit system cavity 4153 can be collectively "tuned" to enhance the quality of a recorded speech output. As described above, in some embodiments, the size and/or shape of the electronic circuit system cavity 4153 can be configured such that the electronic circuit system cavity 4153 defines an acoustic resonant frequency that is within a frequency range of the audible output device 4956 and/or a frequency range of a recorded speech output. In some embodiments, for example, the electronic circuit system cavity 4153 can define at least one acoustic resonant frequency of between about 100 hertz and about 1000 hertz. In other embodiments, the electronic circuit system cavity 4153 can define at least one acoustic resonant frequency of between about 100 hertz and about 3000 hertz.

By enhancing the audible output produced by the audible output device 4956 as described above, the medicament delivery device 4000 can produce audible outputs associated with recorded speech having sufficient volume (e.g., sound pressure level) and without external amplification. In this manner, the power required to produce such audible outputs can be minimized. For example, in some embodiments, the processor 4950 can be configured to output an electronic output to the audible output device 4956 such that the audible output device 4956 outputs an audible output having a sound pressure level in a range between about 61 decibels (dB) and about 65 dB. In another embodiment, the audible output can have a sound pressure level in a range between about 61 decibels (dB) and about 65 dB at a distance of about 6 inches from the audible output device 4956. In yet other embodiments, the audible output can have a sound pressure level in a range between about 61 decibels (dB) and about 65 dB within a distance of about 20 feet from the audible output device 4956.

In other embodiments, the processor 4950 can be configured to output an electronic output to the audible output device 4956 such that the audible output device 4956 outputs an audible output that has a sound pressure level greater than about 61 dB. In yet other embodiments, the audible output can have a sound pressure level greater than about 61 dB at a distance of about 6 inches from the audible output device 4956. In yet other embodiments, the audible output can have a sound pressure level greater than about 61 dB within a distance of about 20 feet from the audible output device 4956.

In some embodiments, the processor 4950 can output an electronic output having a power of less than 100 milliwatts (mW) to the audible output device 4956, and the audible output device 4956 can output an audible output that has a sound pressure level greater than about 61 dB. In yet another embodiment, the electronic output can have a power of less than 100 mW and the audible output can have a sound pressure level greater than about 61 dB at a distance of about 6 inches from the audible output device 4956. In yet another embodiment, the electronic output can have a power of less than 100 mW and the audible output can have a sound pressure level greater than about 61 dB within a distance of about 20 feet from the audible output device 4956.

Figure 23:
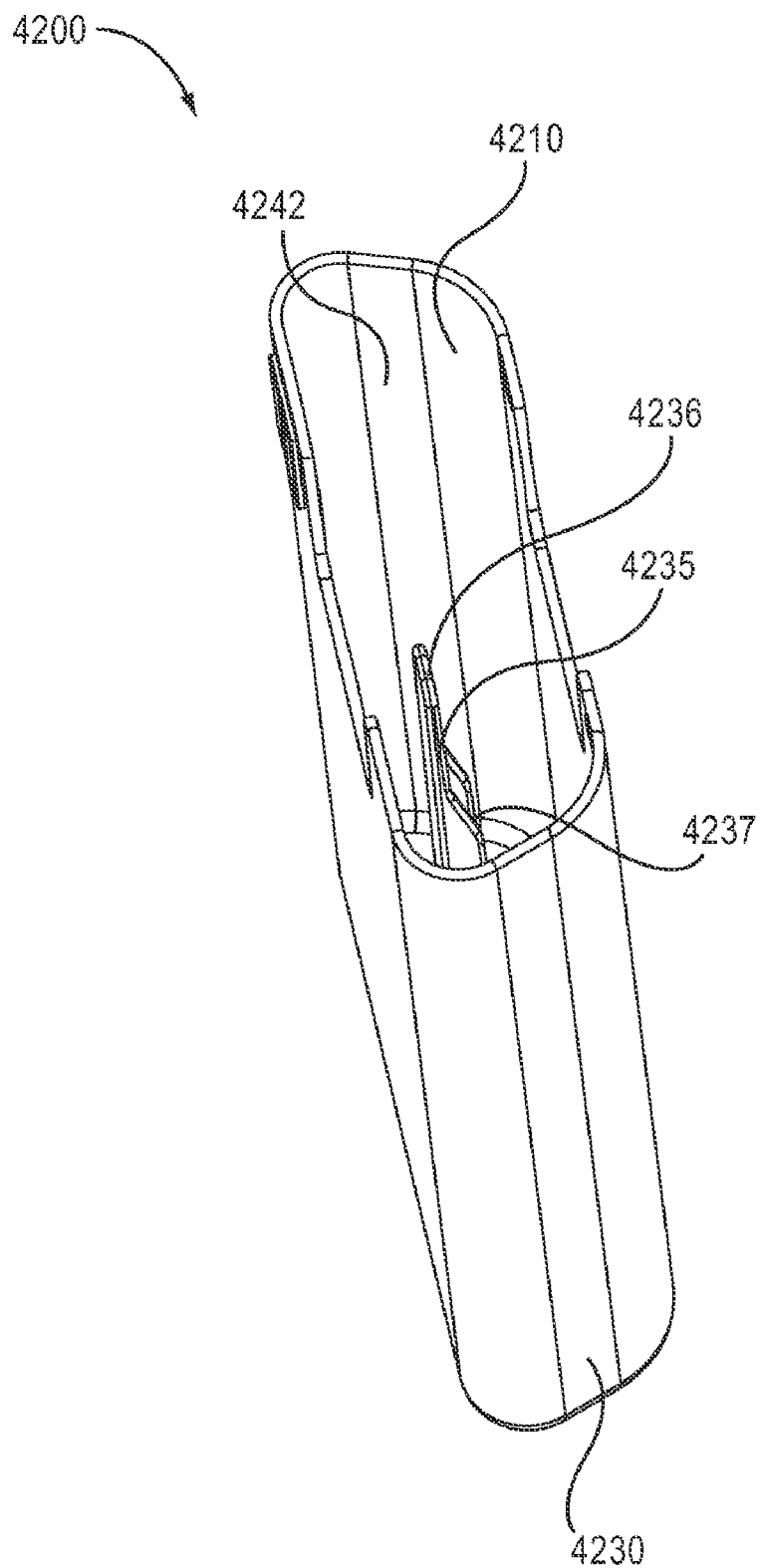

FIGS. 22 and 23 show the cover 4200 of the medicament delivery device 4000. The cover 4200 includes a proximal end portion 4210 and a distal end portion 4230, and defines a cavity 4242. The cavity 4242 of the cover 4200 is configured to receive at least a portion of the housing 4110. The proximal end portion 4210 defines apertures 4215 configured to receive the cover retention protrusions 4142 of the housing 4110 (shown in FIGS. 4B and 6). In this manner, the apertures 4215 and the cover retention protrusions 4142 of the housing 4110 removably retain the cover 4200 about at least a portion of the housing 4110. Said another way, the apertures 4215 and the cover retention protrusions 4142 of the housing 4110 are configured such that the cover 4200 can be removed from a portion of the housing 4110 and then replaced about the portion of the housing 4110.

The distal end portion 4230 of the cover 4200 includes a battery isolation protrusion 4235. The battery isolation protrusion 4235 includes a proximal end portion 4236 and a tapered portion 4237. The proximal end portion 4236 of the battery isolation protrusion 4235 is configured to be removably disposed between the second surface 4966 of the battery assembly 4962 and the contact portion 4918 of the distal end portion 4916 of the battery clip 4910, as described above. When the battery isolation protrusion 4235 is removed, the opening or port associated with the battery isolation protrusion aperture 4121 is opened such that sound waves produced by the audible output device 4956 within the electronic circuit system cavity 4153 can exit the electronic circuit system cavity 4153 to an area outside the housing 4110.

FIGS. 22-23 show the safety lock 4700 of the medicament delivery device 4000. The safety lock 4700 of the medicament delivery device 4000 includes a proximal surface 4740, a distal surface 4760 opposite the proximal surface 4740 and a needle sheath 4720. The safety lock 4700 defines a needle sheath aperture 4770 and a battery isolation protrusion aperture 4775. The battery isolation protrusion aperture 4775 is configured to receive the battery isolation protrusion 4235 of the cover 4200 such that the battery isolation protrusion 4235 can be disposed within the electronic circuit system cavity 4153 or the electronic circuit system 4900, as described above. Similarly stated, the battery isolation protrusion aperture 4775 of the safety lock 4700 is aligned with the battery isolation protrusion aperture 4121 of the housing 4110, such that the battery isolation protrusion 4235 can be disposed within the electronic circuit system cavity 4153 when the cover 4200 is disposed about a portion of the housing 4110. The battery isolation protrusion aperture 4775 is aligned with the battery isolation protrusion aperture 4121 such that sound waves produced by the audible output device 4956 within the electronic circuit system cavity 4153 that exit through the battery isolation protrusion aperture 4121 can travel through the battery isolation protrusion aperture 4775.

The proximal surface 4740 of the safety lock 4700 includes a safety lock protrusion 4742, a stopper 4743, an actuator 4744 and two opposing pull tabs 4741. As described above, when the safety lock 4700 is in a first (locked) position, the safety lock protrusion 4742 is configured to be disposed in the opening 4554 defined by the extensions 4552 of the distal end portion 4544 of the release member 4540. Accordingly, the safety lock protrusion 4742 is configured to prevent the extensions 4552 from moving closer to each other, thereby preventing proximal movement of the release member 4540 of the medicament delivery mechanism 4500 and/or delivery of a medicament. The stopper 4743 of the safety lock 4700 is a protrusion extending from the proximal surface 4740 of the safety lock 4700. The stopper 4743 is configured to contact a portion of the housing 4110 to limit the proximal movement of the safety lock 4700 relative to the housing 4110. In other embodiments, the stopper 4743 can be any structure configured to limit the proximal movement of the safety lock 4700.

The actuator 4744 of the safety lock 4700 has an elongated portion 4745 and a protrusion 4746. The elongated portion 4745 extends in a proximal direction from the proximal surface 4740. In this manner, the elongated portion 4745 can extend through a safety lock actuator opening 4356 of the base 4300 (see e.g., FIG. 26). The protrusion 4746 extends in a direction substantially transverse to the elongated portion 4745 and/or substantially parallel to the proximal surface 4740 of the safety lock 4700. The pull tabs 4741 of the safety lock 4700 include a grip portion 4747 and indicia 4748. The grip portion 4747 of the pull tabs 4741 provides an area for the user to grip and/or remove the safety lock 4700 from the rest of the medicament delivery device 4000. The indicia 4748 provide instruction on how to remove the safety lock 4700.

Figure 25:
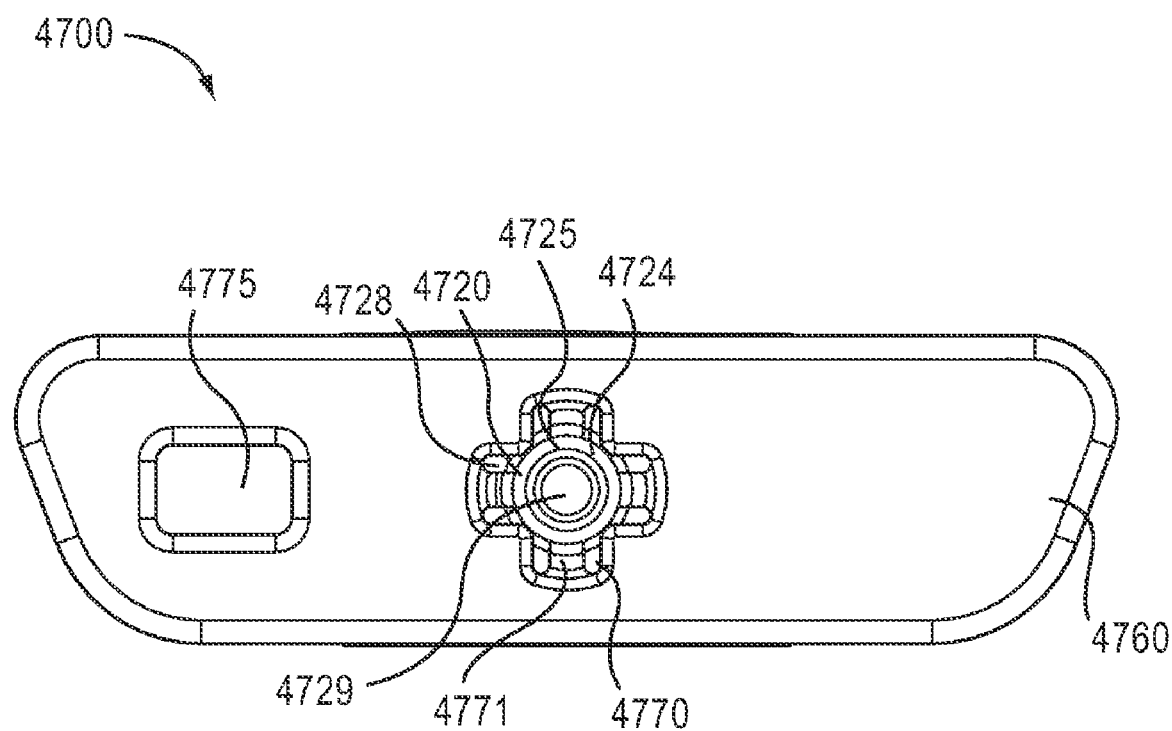
FIG. 25 is a bottom view of the safety lock of the medicament delivery device illustrated in FIG. 24.
Figure 26:
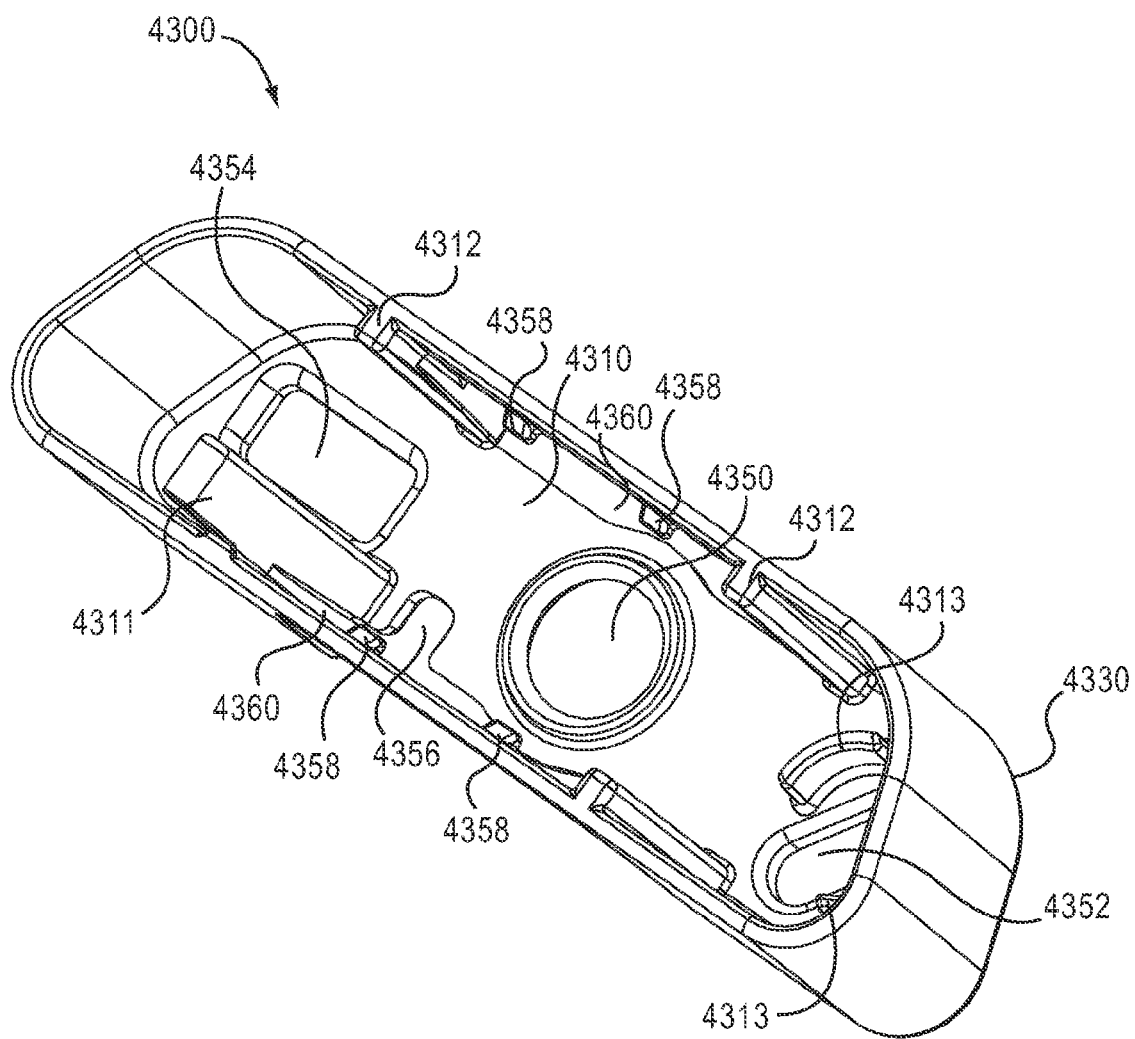
FIG. 26 is a perspective view of a base of the medicament delivery device illustrated in FIGS. 4A and 4B.
Figure 28:
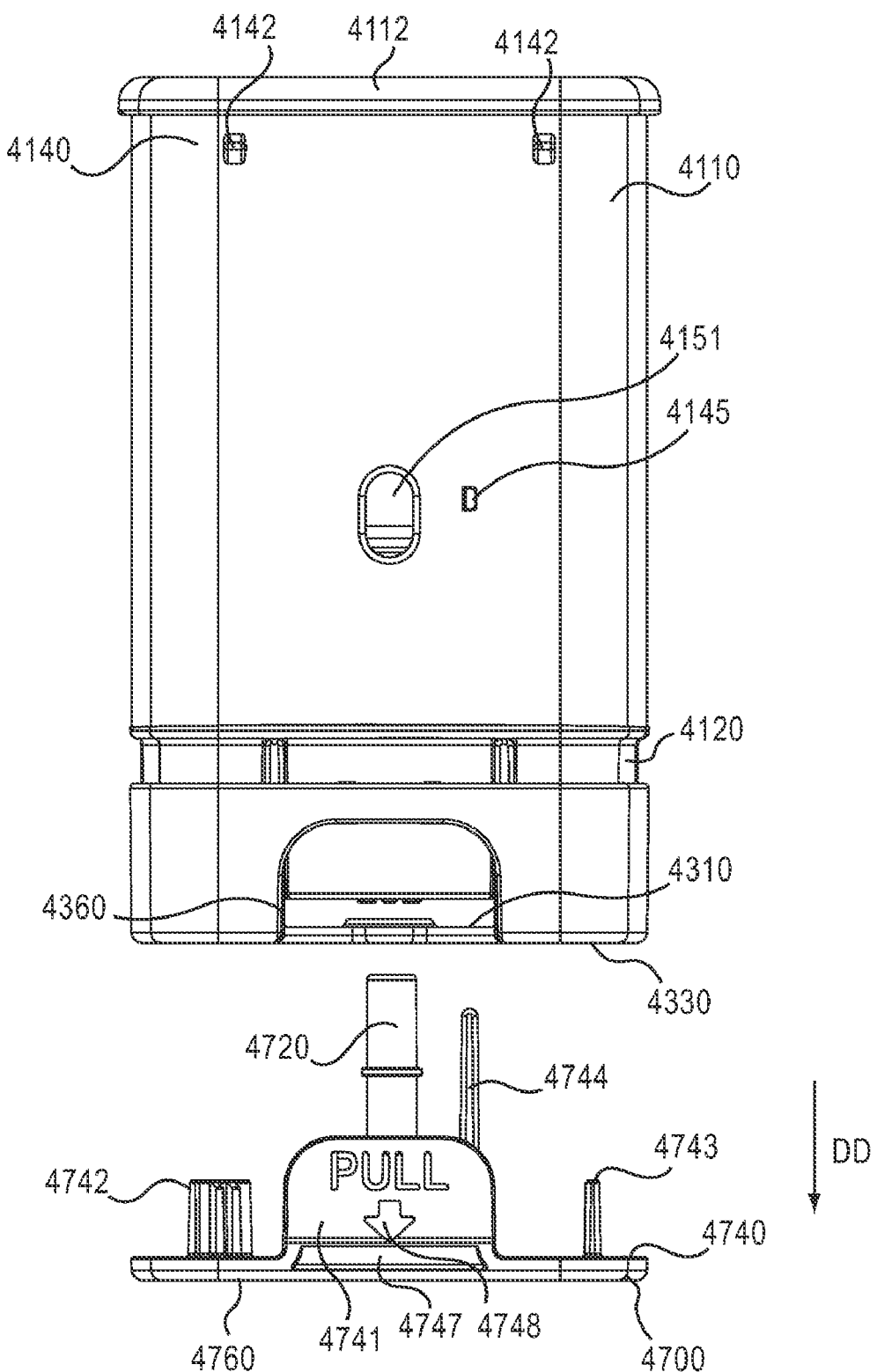
FIG. 28 is a back view of the medicament delivery device illustrated in FIGS. 4A and 4B in a third configuration.
Figure 29:
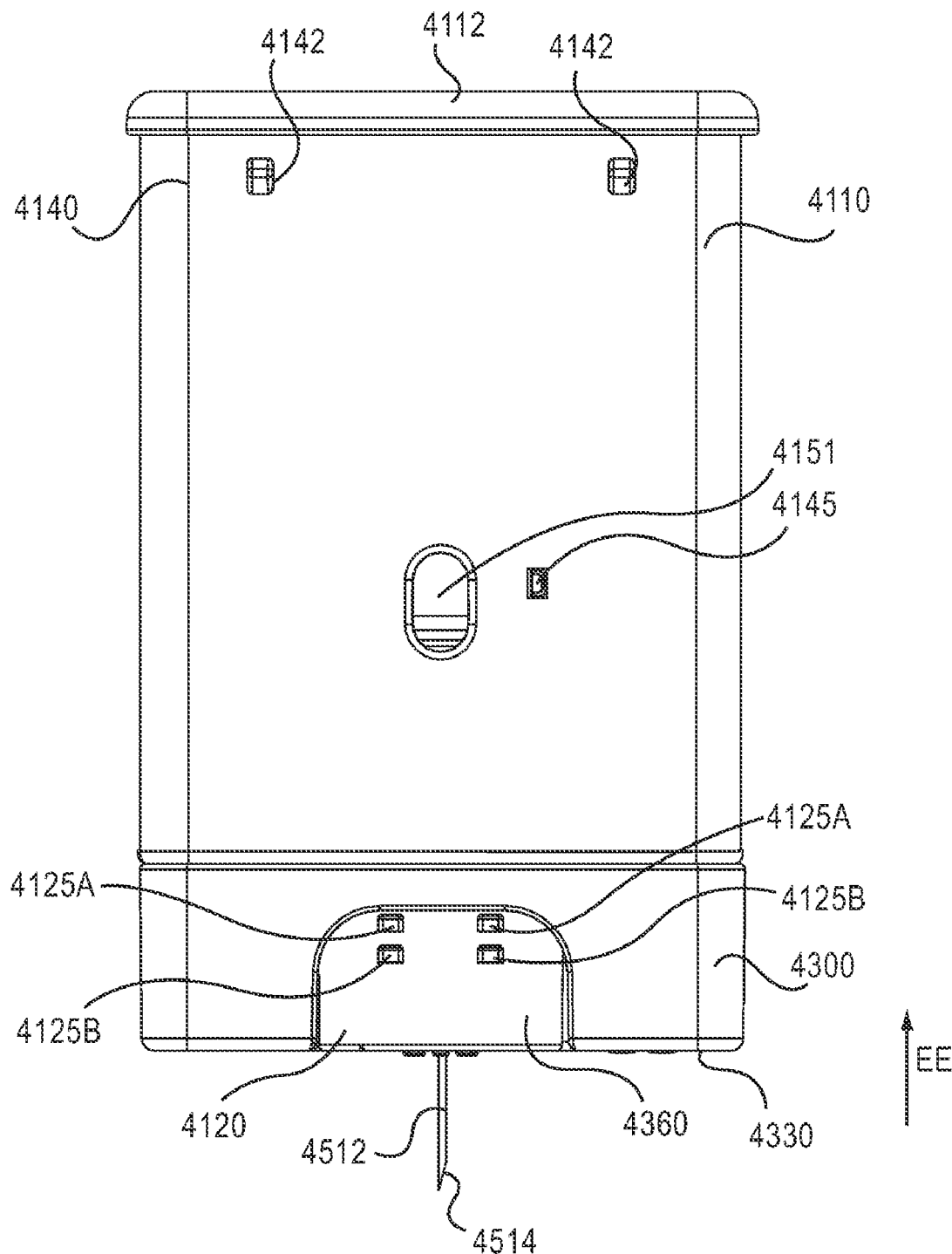
FIG. 29 is a back view of the medicament delivery device illustrated in FIGS. 4A and 4B in a fourth configuration.

As shown in FIG. 25, the needle sheath 4720 of the safety lock 4700 includes a distal end portion 4724, a proximal end portion 4722 and a plurality of ribs 4728. The needle sheath 4720 can also define a lumen 4729 configured to receive the needle 4512. In this manner, the needle sheath 4720 can protect the user from the needle 4512 and/or can keep the needle 4512 sterile before the user uses the medicament delivery device 4000. The distal end portion 4724 of the needle sheath 4720 has an angled ridge 4725. The angled ridge 4725 is configured to allow the proximal end portion 4722 of the needle sheath 4720 to irreversibly move through the needle sheath aperture 4770 of the safety lock 4700 in a distal direction. The needle sheath aperture 4770 has retaining tabs 4771 configured to prevent the proximal movement of the needle sheath with respect to the safety lock 4700. As shown in FIG. 28, the needle sheath 4720 is removed from the needle 4512 when the safety lock 4700 is moved in a distal direction with respect to the housing 4110.

FIG. 24 shows the base 4300 of the medicament delivery device 4000. The base 4300 includes a proximal surface 4310, a distal surface 4330 and base connection knobs 4358. The base 4300 defines a needle aperture 4350, a safety lock protrusion aperture 4352, a battery isolation protrusion aperture 4354, a safety lock actuator opening 4356, and pull tab openings 4360. The needle aperture 4350 is configured to receive the needle 4512 when the medical injector 4000 is actuated. The safety lock protrusion aperture 4352 of the base 4300 receives the safety lock protrusion 4742 of the safety lock 4700. The battery isolation protrusion aperture 4354 of the base 4300 receives the battery isolation protrusion 4235 of the cover 4200 and the stopper 4743 of the safety lock 4700. The safety lock actuator opening 4356 receives the safety lock actuator 4744 of the safety lock 4700. The pull tab openings 4360 are configured to receive the pull tabs 4741 of the safety lock 4700.

The battery isolation protrusion aperture 4354 is aligned with the battery isolation protrusion aperture 4121 such that sound waves produced by the audible output device 4956 within the electronic circuit system cavity 4153 that exit through the battery isolation protrusion aperture 4121 can travel through the battery isolation protrusion aperture 4354.

The proximal surface 4310 of the base 4300 includes an actuator 4311, and protrusions 4313. The actuator 4311 is an elongate member configured to engage the substrate 4924 of the electronic circuit system 4900. The protrusions 4313 of the base 4300 are configured to engage the tapered surfaces 4549 of the extensions 4552 of the release member 4540. As described in further detail herein, when the safety lock 4700 is removed and the base 4300 is moved in a proximal direction with respect to the housing 4110, the protrusion 4313 of the base 4300 are configured to move the extensions 4552 of the release member 4540 closer to each other, actuating the medicament delivery mechanism 4500. As described above, the base connection knobs 4358 are configured to engage the base retention recesses 4125A, 4125B in a way that allows proximal movement of the base 4300 but limits distal movement of the base 4300.

Figure 27:
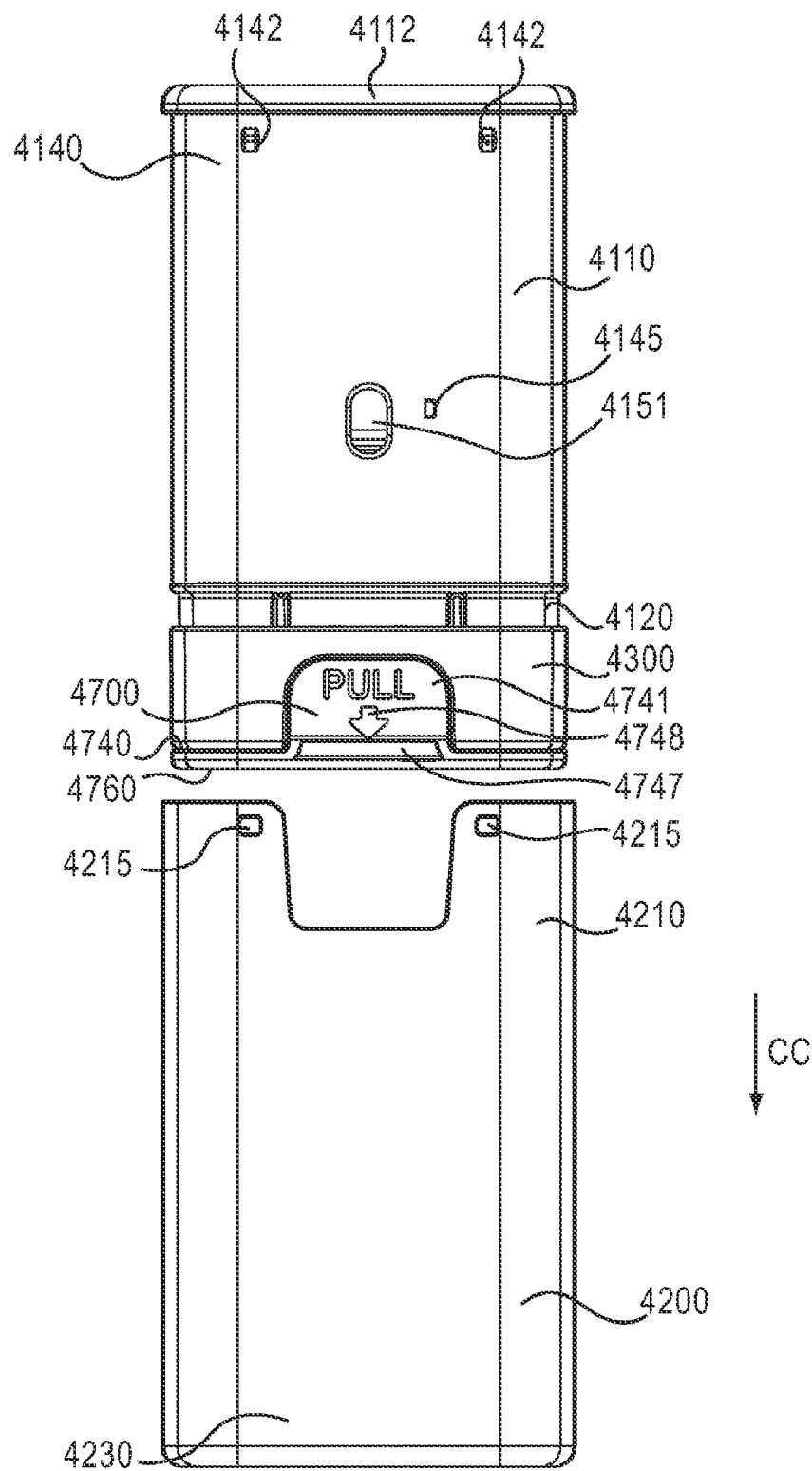
FIG. 27 is a back view of the medicament delivery device illustrated in FIGS. 4A and 4B in a second configuration.

As shown in FIG. 27, the medicament delivery device 4000 is first enabled by moving the medicament delivery device 4000 from a first configuration to a second configuration by moving the cover 4200 from a first position to a second position. The cover 4200 is moved from the first position to the second position by moving it with respect to the housing 4110 in the direction shown by the arrow CC in FIG. 27. When the cover 4200 is moved with respect to the housing 4110 in the direction CC, the battery isolation protrusion 4235 is removed from the area between the battery clip 4910 and the second surface 4966 of the battery assembly 4962. In this manner, the battery assembly 4962 can be operatively coupled to the electronic circuit system 4900 when the cover 4200 is removed, thereby providing power to the electronic circuit system 4900.

When power is provided, as described above, the electronic circuit system 4900 can output one or more predetermined electronic outputs and/or audible outputs. For example, in some embodiments, the electronic circuit system 4900 can output an electronic signal associated with recorded speech to the audible output device 4956 such that the audible output device 4956 outputs an audible output. Such an electronic signal can be, for example, associated with a .WAV file that contains a recorded instruction instructing (e.g., prompting) the user in the operation of the medicament delivery device 4000. Such an instruction can state, for example, "remove the safety tab near the base of the auto-injector." The electronic circuit system 4900 can simultaneously output an electronic signal to one and/or both of the LEDs 4958A, 4958B thereby causing one and/or both of the LEDs 4958A, 4958B to flash a particular color. In this manner, the electronic circuit system 4900 can provide both audible and visual instructions to assist the user in the initial operation of the medical injector 4000. Further, because the battery isolation protrusion 4235 has been removed from the battery isolation protrusion aperture 4121, an audible output by the audible output device 4956 can include sound waves produced within the electronic circuit system cavity 4153 that exit through the battery isolation protrusion aperture 4121.

In other embodiments, the electronic circuit system 4900 can output an electronic output and/or an audible output associated with a description and/or status of the medicament delivery device 4000 and/or the medicament contained therein. For example, in some embodiments, the electronic circuit system 4900 can output an audible message indicating the type of medicament contained in the medicament delivery device 4000, the expiration date of the medicament, the dosage of the medicament or the like.

As described above, the medicament delivery device 4000 can be repeatedly moved between the first configuration and the second configuration when the cover 4200 is moved repeatedly between the first position and the second position respectively. Said another way, the cover 4200 can be removed and replaced about the housing 4110 any number of times. When the cover 4200 is moved from the second position to the first position, the battery isolation protrusion 4235 is inserted between the battery clip 4910 and the second surface 4966 of the battery assembly 4962, deactivating the electronic circuit system 4900 and closing the acoustic port associated with the battery isolation protrusion aperture 4121. When the cover is moved from the first position to the second position a second time, the electronic circuit system 4900 is once again activated and the acoustic port is opened. In this manner, the cover 4200 can be removed and the electronic circuit system 4900 can output an electronic output without compromising the sterility of the needle 4512.

After the cover 4200 is removed from the housing 4110, the medicament delivery device 4000 can be moved from the second configuration to a third configuration by moving the safety lock 4700 from a first position to a second position. The safety lock 4700 is moved from a first position to a second position by moving the safety lock 4700 with respect to the housing 4110 in the direction shown by the arrow DD in FIG. 28. When the safety lock 4700 is moved from the first position to the second position, the safety lock protrusion 4742 is removed from between the extensions 4552 of the release member 4540, thereby enabling the medicament delivery mechanism 4500. When the actuator 4744 of the safety lock 4700 moves irreversibly the first switch 4972 of the electronic circuit system 4900 to the second state, the electronic circuit system 4900 can output one or more predetermined electronic outputs and/or audible outputs. For example, in some embodiments, a processor (not shown) can output an electronic signal associated with recorded speech to the audible output device 4956. Such an electronic signal can be, for example, associated with a recorded message notifying the user of the status of the medicament delivery device 4000. Such a status message can state, for example, "The medical injector is now enabled." The electronic circuit system 4900 can also simultaneously output an electronic signal to one and/or both of the LEDs 4958A, 4958B, thereby causing one and/or both of the LEDs 4958A, 4958B to stop flashing, change color, produce a particular lighting sequence, or the like.

In some embodiments, the first actuation portion 4926 and the actuator 4744 can be configured such that the actuator 4744 must move a predetermined distance before the actuator 4744 engages the boundary 4929 of the opening 4928. For example, in some embodiments, the actuator 4744 must move approximately 0.200 inches before the actuator 4744 engages the boundary 4929 of the opening 4928. In this manner, the safety lock 4700 can be moved slightly without irreversibly moving the first switch 4972 of the electronic circuit system 4900 to the second state. Accordingly, this arrangement will permit the user to inadvertently and/or accidentally move the safety lock 4700 without actuating the electronic circuit system 4900.

In some embodiments, the electronic circuit system 4900 can be configured to output the status message for a predetermined time period, such as, for example, five seconds. After the predetermined time period has elapsed, the electronic circuit system 4900 can output an audible message further instructing the user in the operation of the medicament delivery device 4000. Such an instruction can state, for example, "Place the base of the auto-injector against the patient's thigh. To complete the injection, press the base firmly against the patient's thigh." In some embodiments, the electronic circuit system 4900 can simultaneously output an electronic signal to one and/or both of the LEDs 4958A, 4958B, thereby causing one and/or both of the LEDs 4958A, 4958B to flash a particular color and/or produce a particular lighting sequence. In this manner, the electronic circuit system 4900 can provide both audible and/or visual instructions to assist the user in the placement and actuation of the medicament delivery device 4000. In some embodiments, the electronic circuit system 4900 can be configured to repeat the instructions after a predetermined time period has elapsed.

After the safety lock 4700 is moved from the first position to the second position, the medicament delivery device 4000 can be moved from the third configuration to a fourth configuration by moving the base 4300 from a first position to a second position. The base 4300 is moved from its first position to its second position by placing the medicament delivery device 4000 against the body of the patient and moving the base 4300 with respect to the housing 4110 in the direction shown by the arrow EE in FIG. 29. Moving the base 4300 from the first position to the second position causes the protrusions 4313 on the proximal surface 4310 of the base 4300 to engage the tapered surfaces 4549 of the extensions 4552 of the release member 4540, causing the release member 4540 to actuate the medicament delivery mechanism 4500 and deliver a medicament to a body of a patient.

When the base 4300 is moved from the first position to the second position, the medicament delivery mechanism 4500 is actuated such that the puncturer 4541 of the release member 4540 is brought in contact with and/or punctures the frangible seal 4573 of the gas container 4570. In some embodiments, the movement of the release member 4540 can be caused by a spring (not shown in FIG. 12). After the frangible seal 4573 has been punctured, an actuating portion of a compressed gas can escape from the gas container 4570 and flow via the gas passageway 4144 into the medicament cavity 4157. The gas applies gas pressure to the movable member 4530 causing the movable member 4530 and the carrier 4520 to move in a distal direction within the medicament cavity 4157. When the carrier 4520 moves distally within the medicament cavity 4157, the carrier 4520 and the medicament container 4560 are in a first configuration. Accordingly, as described above, the medicament container 4560 is connected to the carrier 4520 by a "snap fit" connection. In this manner, the medicament container 4560 and the needle 4512 contemporaneously move with movable member 4530 and/or the carrier 4520 in a distal direction. As described above, the proximal end portion 4516 of the needle 4512 is connected to the distal end portion 4522 of the carrier 4520 and is spaced from the seal 4523 of the medicament container 4560 when the carrier 4520 is in its first configuration. Said another way, the medicament container 4560 and the needle 4512 do not define a medicament delivery path when the carrier 4520 is in the first configuration. The movement of the needle 4512 in a distal direction causes a distal end portion 4514 of the needle 4512 to exit the housing 4110 and enter the body of a patient prior to administering a medicament.

After the carrier 4520 and/or the needle 4512 have moved within the medicament cavity 4157 a predetermined distance, the carrier 4520 and the medicament container 4560 are moved from the first configuration to a second configuration. In the second configuration of the carrier 4520, the medicament container 4560 is released from the "snap-fit" allowing the medicament container 4560 and the movable member 4530 to continue to move in a distal direction relative to the carrier 4520. Said another way, the medicament container 4560 is configured to slidably move within the carrier 4520 when the carrier is moved from the first configuration to the second configuration. As the medicament container 4560 continues to move within the carrier 4520, the proximal end portion 4516 of the needle 4512 contacts and punctures the seal 4523 of the medicament container 4560. This allows the medicament contained in the medicament container 4560 to flow into the lumen (not shown) defined by the needle 4512, thereby defining a medicament delivery path.

As the medicament container 4560 contacts the distal end of the carrier 4520, the medicament container 4560 stops moving within the carrier 4520 while the movable member 4530 continues to move in a distal direction. This causes the piston portion 4534 of the movable member 4530 to sealingly slide and/or move within the medicament container 4560 containing a liquid medicament. As the piston portion 4534 of the movable member 4530 sealingly slides and/or moves within the medicament container 4560, the piston portion 4534 generates a pressure upon the medicament contained within the medicament container 4560, thereby allowing at least a portion of the medicament to flow out of the medicament container 4560 and into the lumen defined by the needle 4512. The medicament is delivered to a body of a user via the medicament delivery path defined by the medicament container 4560 and the needle 4512.

Figure 21:
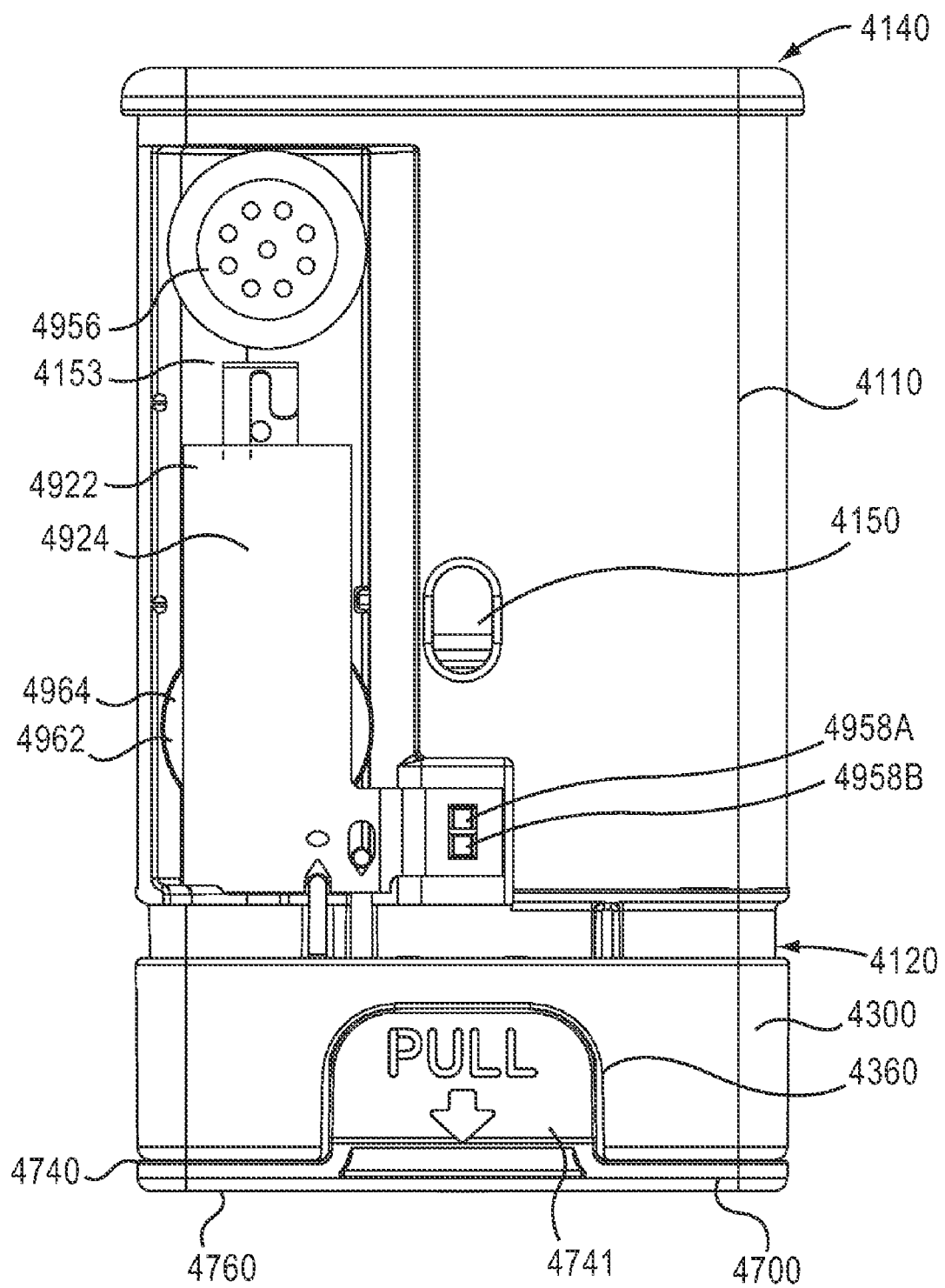
FIG. 21 is a front view of the medicament delivery device illustrated in FIGS. 4A and 4B in a first configuration showing the electronic circuit system.

As described above, the actuator 4311 of the base 4300 actuates the electronic circuit 4900 to trigger a predetermined output or sequence of outputs when the base 4520 is moved from its first position to its second position (see, e.g., FIG. 21). When the actuator 4311 is moved in a proximal direction, the electronic circuit system 4900 is actuated to output one or more predetermined electronic outputs and/or audible outputs. For example, in some embodiments, the electronic circuit system 4900 can output an electronic signal associated with recorded speech to the audible output device 4956. Such an electronic signal can be, for example, associated with an audible countdown timer, instructing the user on the duration of the injection procedure. Said another way, if it takes, for example, ten seconds to complete an injection, an audible countdown timer can count from ten to zero ensuring that the user maintains the medicament delivery device 4000 in place for the full ten seconds. In other embodiments, the electronic signal can be, for example, associated with a recorded message notifying the user that the injection is complete, instructing the user on post-injection disposal and safety procedures, instructing the user on post-injection medical treatment or the like. Such a status message can state, for example, "The injection is now complete. Please seek further medical attention from a doctor." The electronic circuit system 4900 can also simultaneously output an electronic signal to one and/or both LEDs 4958A, 4958B, thereby causing one and/or both LEDs 4958A, 4958B to stop flashing, change color, produce a particular lighting sequence, or the like, to provide a visual indication that the injection is complete.

Figure 30:
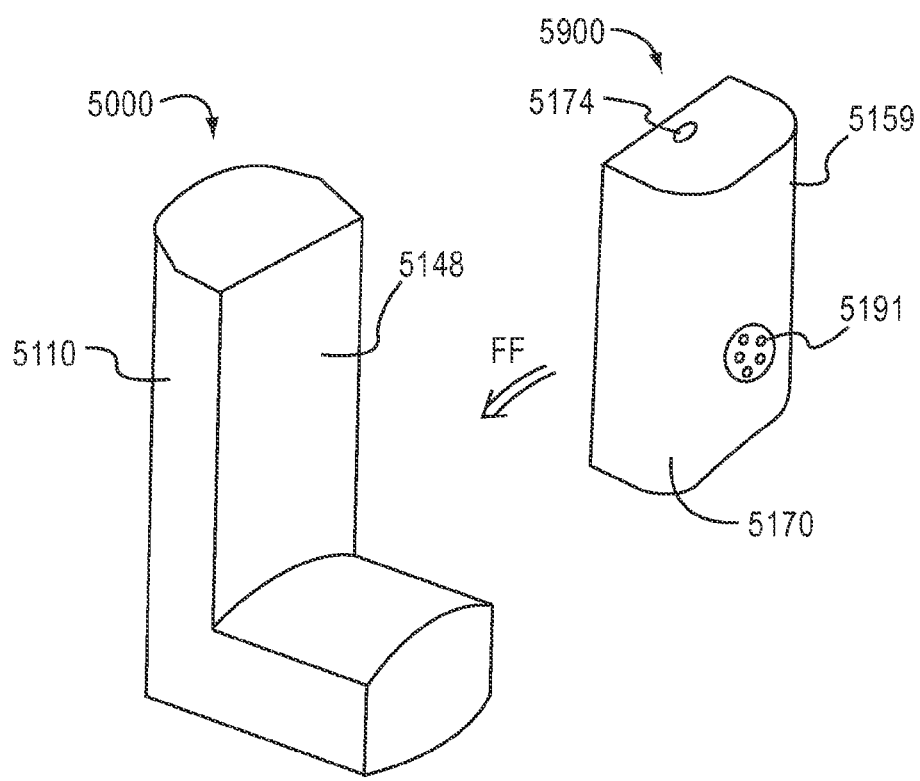
FIG. 30 is a schematic illustration of a medicament delivery device and an electronic circuit system assembly according to an embodiment of the invention.
Figure 31:
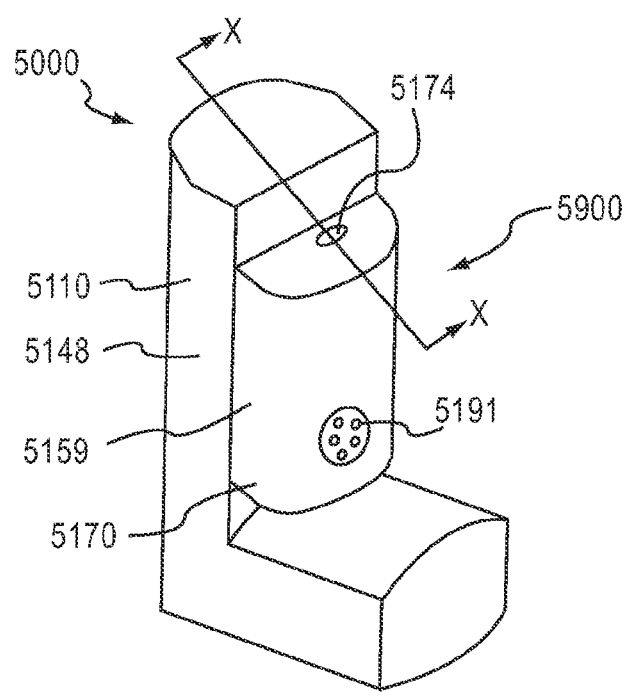
FIG. 31 is a schematic illustration of the electronic circuit system assembly shown in FIG. 30 coupled to the medicament delivery device shown in FIG. 30.
Figure 32:
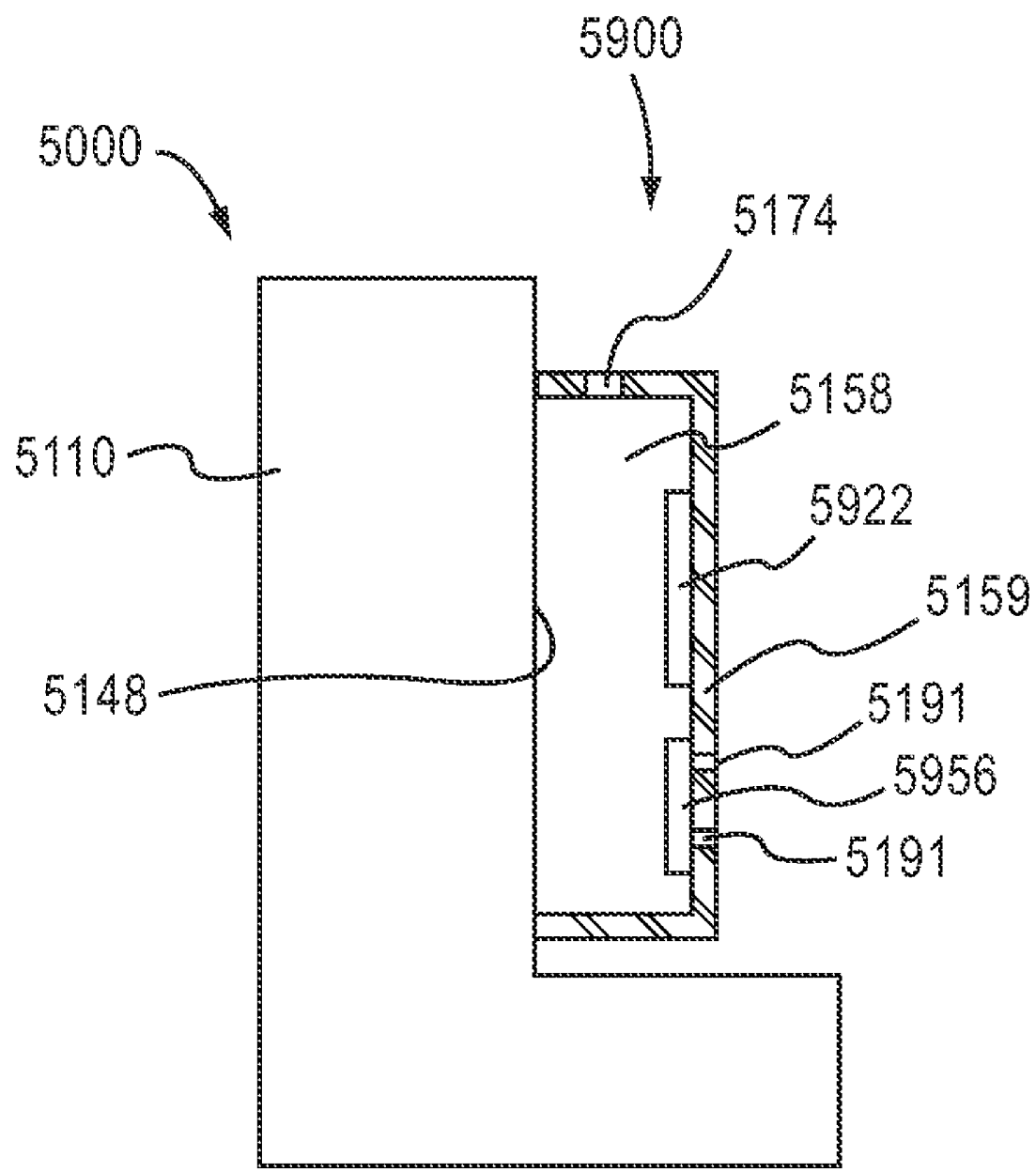
FIG. 32 is a cross-sectional view of the electronic circuit system assembly and the medicament delivery device shown in FIG. 31, taken along a plane including line X-X.

Although the housing 4110 is shown and described above as defining the electronic circuit system cavity 4153, in other embodiments, the housing 4110 need not define the electronic circuit system cavity 4153. For example, in some embodiments, the electronic circuit system assembly can include a housing that defines a cavity and/or an acoustic enclosure within which a speaker is disposed. For example, FIGS. 30-32 are schematic illustrations of medicament delivery device 5000 and an electronic circuit system assembly 5900 according to an embodiment. The medicament delivery device 5000 can be any suitable device for delivering a medicament into a body of a patient. For example, the medicament delivery device 5000 can be an inhaler, a medical injector (e.g., a syringe, pen injector, auto-injector, or the like), a transdermal medicament delivery system or the like. The medicament delivery device 5000 includes a housing 5110 containing a medicament container (not shown in FIGS. 30-32) and/or a medicament delivery mechanism (not shown in FIG. 30-32) for delivering the medicament into the body.

As shown in FIGS. 30 and 31, the electronic circuit system assembly 5900 is configured to be coupled to the housing 5110 of the medicament delivery device 5000. In some embodiments, for example, the electronic circuit system assembly 5900 can be configured to be coupled to a particular medicament delivery device as a kit (e.g., a retrofit kit). In other embodiments, the electronic circuit system assembly 5900 can be configured to be coupled to multiple different medicament delivery devices. Similarly stated, in some embodiments, the electronic circuit system assembly 5900 can be a part of a "universal" retrofit kit. As described above, the electronic circuit system 5900 is configured to produce and/or output an audible output associated with a use of the medicament delivery device 5000.

The electronic circuit system assembly 5900 includes at least a housing 5170, a printed circuit board 5922, and a speaker 5956. The printed circuit board 5922 includes electronic components (e.g., a processor, a battery assembly, or the like; not shown in FIGS. 30-32) operatively coupled to produce and/or output an audible output. The printed circuit board 5922, the speaker 5956 and the associated electronic components can be similar to those included in the electronic circuit system 4900 shown and described above.

The housing 5170 of the electronic circuit system assembly 5900 includes a side wall 5159 that defines a cavity 5158, an end opening 5174 and multiple sound apertures 5191. As shown in FIG. 32 the printed circuit board 5922 and the speaker 5956 are coupled to the housing 5170 of the electronic circuit system assembly 5900 within the cavity 5158. In particular, the speaker 5956 is disposed against the side wall 5159 such that a first side (e.g., a front side) of the speaker 5956 is disposed adjacent the sound apertures 5191. In this manner, sound waves from the first side of speaker 5956 can travel from the speaker 5956 to a region outside of the housing 5170 of the electronic circuit system assembly 5900 via the sound apertures 5191.

The housing 5170 of the electronic circuit system assembly 5900 is coupled to the housing 5110 of the medicament delivery device 5000, as shown by the arrow FF in FIG. 30. The housing 5170 can be coupled to the housing 5110 by any suitable mechanism (e.g., by mating protrusions and recesses, by heat staking, using an adhesive bond, or the like). As shown in FIG. 32, the housing 5110 of the medicament delivery device 5000 and the cavity 5158 of the housing 5170 of the electronic circuit system assembly 5900 collectively define an acoustic enclosure within which the speaker 5956 is disposed. Said another way, a surface 5148 of the housing 5110 and the side wall 5159 collectively define the boundary of a region, volume and/or space that is configured to minimize or attenuate noise and/or enhance the audible output of the speaker 5956, in a manner as described above. Moreover, the opening 5174 can function as a port to allow sound waves produced by a second side (e.g., a back side) of the speaker 5956 to exit the cavity 5158 of the housing 5170 to an area outside the housing 5170. As described above, the opening 5174 can be spaced a predetermined distance from the speaker 5956 to enhance the quality of the audible output produced by the speaker 5956.

Because the electronic circuit system 5900 includes the electronic components (e.g., a processor configured to produce an electronic signal, the speaker 5956 and the like) and defines the cavity 5158, the electronic components and the cavity 5158 can be complimentarily selected and/or configured to enhance the quality of the audible output produced by the speaker 5956. Similarly stated, this arrangement allows the sound performance of the electronic circuit system 5900 to be optimized substantially independent of the housing 5110 of the medicament delivery device 5900.

Although the acoustic enclosure is shown as being defined, in part, by a surface 5148 of the housing 5110 of the medicament delivery device 5000, in other embodiments, the housing 5170 of the electronic circuit system assembly 5900 can define a substantially enclosed cavity 5158 configured to function as an acoustic chamber. In some embodiments, for example, a housing 5170 can include a sidewall configured to be disposed against a portion of the medicament delivery device 5000 and define a boundary of an acoustic enclosure. In such embodiments, the side wall can be any suitable side wall for coupling the housing 5170 of the electronic circuit system assembly 5900 to the medicament delivery device 5000 and/or enhancing the audible output produced by the speaker 5956. For example, the side wall can be an elastic side wall. In other embodiments, the side wall can be a porous side wall.

Although the cavity 5158 of the housing 5170 of the electronic circuit system assembly 5900 is shown as being disposed adjacent the medicament delivery device 5000, in some embodiments, a portion of the medicament delivery device can be disposed within the cavity. For example, in some embodiments, the electronic circuit system assembly can be disposed about a portion of the medicament delivery device.

While various embodiments of the invention have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

For example, although the audio output device 4956 is shown and described as having front portion 4957 configured to produce a first set of sound waves and a back portion 4955 opposite the front portion configured to produce a second set of sound waves, in other embodiments, an audio device can have a first portion configured to produce a first set of sound waves and a second portion configured to produce a second set of sound waves wherein the first portion is not opposite the second portion. For example, in some embodiments, an audio output device can have a first surface configured to produce a first set of sound waves and a second surface adjacent and/or in contact with the first surface, the second surface configured to produce a second set of sound waves.

Although the electronic circuit system cavity 4153 is shown as defining a substantially rectangular acoustic enclosure, in some embodiments, a medicament delivery device can define an acoustic enclosure having any suitable shape. For example, in some embodiments, a medicament delivery device can define a substantially cylindrical acoustic enclosure.

The electronic circuit system cover 4170 is matingly coupled to the housing 4110 such that the electronic circuit system cover 4170 and the electronic circuit system cavity 4153 collectively define an acoustic enclosure within which the audible output device 4956 is disposed. Said another way, the electronic circuit system cover 4170 and the electronic circuit system cavity 4153 collectively form a region, volume and/or space that is configured to minimize or attenuate noise and/or enhance the audible output of the audible output device 4956. Moreover, the volume associated with the region defined by the electronic circuit system cover 4170 and the electronic circuit system cavity 4153 is larger than the volume of the audible output device 4956 and/or the electronic circuit system 4900 disposed within the region. In this manner, the acoustic enclosure defined by the electronic circuit system cover 4170 and the electronic circuit system cavity 4153 is configured to contain a volume of air behind the audible output device 4956.

Although the electronic circuit system cavity 4153 is shown as defining the acoustic enclosure, in other embodiments, a medicament delivery device can define an acoustic enclosure that is separate from a cavity within which a portion of the electronic circuit system is disposed. In some embodiments, for example a housing can define a first cavity within which a printed circuit board of an electronic circuit system is disposed and a second cavity distinct from the first cavity within which a portion of an audio output device is disposed. The first cavity can include, for example, potting material to enhance the reliability and/or performance of the printed circuit board. The second cavity can be devoid of internal structure and can function as an acoustic enclosure.

Although the electronic circuit system cavity 4153 is shown and described as being substantially devoid of structure, in other embodiments, an electronic circuit system cavity can include components therein to enhance the performance of the cavity as an acoustic enclosure. For example, in some embodiments, an electronic circuit system cavity can include a set of baffles. In this manner, the length through which sound waves produced by a back portion of an audio output device can be increased to a value greater than an overall length of the electronic circuit system cavity.

Although the electronic circuit system cavity 4153 is shown and described as having a single "port" (i.e., the battery isolation protrusion aperture 4121) disposed at the distal end thereof, in other embodiments, an electronic circuit system cavity 4153 can include a port disposed in any suitable location. For example, in some embodiments, an electronic circuit system cavity can include a port disposed at the proximal end thereof. Moreover, in some embodiments, an electronic circuit system cavity 4153 can include multiple openings at multiple different locations.

While the housing shown in the current embodiment is rigid, a portion of the housing can be made flexible such that the flexible portion of the housing operates as a passive counterpart to the active operation of the audible output device. In such embodiment, the flexible portion of the housing can dynamically adjust the acoustic enclosure size and/or shape to improve the sound pressure level produced by the audible output device. For example, in some embodiments, the sidewall of the housing that defines a portion of an acoustic enclosure can be a movable member such as, for example, a piston. In yet other embodiments, the sidewall can be a flexible member such as, for example, a diaphragm. The sidewall can be integrally formed with the housing or can be separately formed.

Although the battery assembly 4962 is shown and described as including two batteries stacked on top of one another, in other embodiments, a battery assembly can include two or more batteries that are not arranged in a stacked fashion. For example, in some embodiments, a battery assembly can include two or more batteries that are arranged end-to-end such that an edge of one battery is in contact with an edge of another battery. In other embodiments, a battery assembly can include two or more batteries that are spaced apart from each other. Similarly, although the battery clip 4910 is shown and described as having a single contact portion 4918 at the distal end thereof, in other embodiments (e.g., embodiments in which the battery assembly includes batteries in an unstacked relationship), a battery clip can include more than one contact portion.

Although the battery assembly 4962 is shown and described above as including three volt, "watch-style" batteries, in other embodiments, the electronic circuit system 4900 can be powered by any suitable power source. For example, in some embodiments, the battery assembly 4962 can include one or more rechargeable batteries. Such an arrangement is well-suited for multiple-use medicament delivery devices (e.g., chronic-care devices). In other embodiments, an electronic circuit system can be devoid of a battery assembly 4962. Said another way, in some embodiments, electrical power can be provided to an electronic circuit system by a source other than batteries (e.g., a solar power supply, a capacitance-based power supply, a bio-active power supply that produces electricity by breaking down organic materials, a small-scale mechanical generator, a small-scale fuel cell or the like).

Although the medicament delivery device 4000 is shown and described as being an actual medicament delivery device, in some embodiments, the housing 4110 and/or the electronic circuit system 4900 can be associated with a simulated medicament delivery device. Such simulated devices can be devoid of medicament and/or needles, and can be used, for example, to train users in the operation of a corresponding actual medicament delivery device.

Some embodiments include a processor and a related processor-readable medium having instructions or computer code thereon for performing various processor-implemented operations. Such processors can be implemented as hardware modules such as embedded microprocessors, microprocessors as part of a computer system, Application-Specific Integrated Circuits ("ASICs"), and Programmable Logic Devices ("PLDs"). Such processors can also be implemented as one or more software modules in programming languages as Java, C++, C, assembly, a hardware description language, or any other suitable programming language.

A processor according to some embodiments includes media and computer code (also can be referred to as code) specially designed and constructed for the specific purpose or purposes. Examples of processor-readable media include, but are not limited to: magnetic storage media such as hard disks, floppy disks, and magnetic tape; optical storage media such as Compact Disc/Digital Video Discs ("CD/DVDs"), Compact Disc-Read Only Memories ("CD-ROMs"), and holographic devices; magneto-optical storage media such as optical disks, and read-only memory ("ROM") and random-access memory ("RAM") devices. Examples of computer code include, but are not limited to, micro-code or micro-instructions, machine instructions, such as produced by a compiler, and files containing higher-level instructions that are executed by a computer using an interpreter. For example, an embodiment of the invention can be implemented using Java, C++, or other object-oriented programming language and development tools. Additional examples of computer code include, but are not limited to, control signals, encrypted code, and compressed code.

Although various embodiments have been described as having particular features and/or combinations of components, other embodiments are possible having a combination of any features and/or components from any of embodiments where appropriate. For example, although the medicament delivery device 4000 is shown and described as including an electronic circuit system cavity 4153 that can function as an acoustic enclosure and an electronic circuit system devoid of a signal amplifier, in other embodiments, a medicament delivery device can include an acoustic enclosure and an electronic circuit system having a signal amplifier. In such embodiments, for example, the electronic signal produced by a processor (which can have a power of less than 100 milliwatts) can be amplified to provide an input signal to a speaker having a power level of greater than the power level of the signal produced by the processor.

What is claimed is:

1. An apparatus, comprising:
a medicament delivery device including a housing, a medicament container, and a medicament delivery member, the medicament container disposed within the housing, at least a portion of the medicament delivery member disposed within the housing; and an electronic circuit system coupled to the housing, the electronic circuit system including an audible output device and a cover, a first portion of the audible output device configured to produce a first plurality of sound waves, a second portion of the audible output device configured to produce a second plurality of sound waves having a phase difference with the first plurality of sound waves, the housing and the cover collectively defining an acoustic enclosure, at least one of the housing or the cover defining a first opening, at least one of the housing or the cover defining a second opening, the audible output device configured to be disposed within the acoustic enclosure such that the first plurality of sound waves travels from the first portion of the audible output device to a region outside of the housing via the first opening and the second plurality of sound waves travels from the second portion of the audible output device to the region outside of the housing via the second opening, the second opening spaced apart from the first opening such that the phase difference between the first plurality of sound waves and the second plurality of sound waves is shifted when the first plurality of sound waves exits the first opening and the second plurality of sound waves exits the second opening.

2. The apparatus of claim 1, wherein the housing defines an internal space, the internal space of the housing including the medicament container and the portion of the medicament delivery member, the internal space of the housing being at least partially isolated from the acoustic enclosure.

3. The apparatus of claim 1, wherein:
the second opening is spaced apart from the first opening such that the first plurality of sound waves is substantially in phase with the second plurality of sound waves when the first plurality of sound waves exits the first opening and the second plurality of sound waves exits the second opening.

4. The apparatus of claim 1, wherein the acoustic enclosure defines at least one acoustic resonant frequency within the acoustic frequency range of the audible output device.

5. The apparatus of claim 1, wherein the audible output device is a speaker configured to output an audible output having a sound pressure level greater than about 61 decibels.

6. The apparatus of claim 1, wherein the audible output device is a speaker configured to output an audible output having a sound pressure level greater than about 61 decibels at a distance of about 6 inches from the speaker.

7. The apparatus of claim 1, wherein the audible output device is a speaker configured to output an audible output having a sound pressure level greater than about 61 decibels within a distance of about 20 feet from the speaker.

8. The apparatus of claim 1, wherein:
the electronic circuit system is configured to output to the audible output device an electronic signal having a power of less than 100 milliwatts; and
the audible output device is configured to output a recorded speech output in response to the electronic signal, the recorded speech output having a sound pressure level greater than about 61 decibels.

9. The apparatus of claim 1, wherein the audible output device is a speaker, the housing includes a spacer configured to be disposed adjacent the speaker such that a front portion of the speaker is in contact with a portion of the cover.

10. The apparatus of claim 1, wherein at least a portion of the housing that defines the acoustic enclosure includes a flexible wall.

11. An apparatus, comprising:
a medicament delivery device including a housing and a medicament container, the medicament container disposed within the housing; and
an electronic circuit system coupled to the housing, the electronic circuit system including a speaker and a cover, the speaker includes a front portion and a back portion, the front portion of the speaker configured to output a first audible output including a first plurality of sound waves, the back portion of the speaker configured to output a second audible output including a second plurality of sound waves, the cover defining a first exit path through which the first plurality of sound waves is configured to travel from the front portion of the speaker to a region outside of the housing, the housing defining at least a portion of a second exit path through which the second plurality of sound waves is configured to travel from the back portion of the speaker to the region outside of the housing, a length of the first exit path different from a length of the second exit path such that the first plurality of sound waves is substantially in phase with the second plurality of sound waves when the first plurality of sound waves exits the first exit path and the second plurality of sound waves exits the second exit path.

12. The apparatus of claim 11, wherein the length of the first exit path is less than the length of the second exit path.

13. The apparatus of claim 11, wherein:
the cover defines a first opening through which the first plurality of sound waves is configured to travel; and
the housing defines a second opening through which the second plurality of sound waves is configured to travel, the first opening spaced apart from the second opening by a distance of between about 2.5 inches and about 3 inches.

14. The apparatus of claim 13, wherein the second opening is configured to be selectively covered by a moveable member of the medicament delivery device.

15. The apparatus of claim 13, wherein the second opening is configured to be selectively covered by a moveable member of the medicament delivery device, the moveable member being at least one of a sleeve, a safety lock, or a needle guard.

16. The apparatus of claim 11, wherein the medicament delivery device includes a member movably coupled to the housing, the member configured to prevent the medicament delivery device from delivering a medicament when in a first position, a portion of the member disposed within the second exit path when in the first position.

17. The apparatus of claim 1, wherein the medicament container includes epinephrine.

18. An apparatus, comprising:
a medicament delivery device including a housing and a medicament container, the medicament container disposed within the housing; and
an electronic circuit system including a speaker and a cover, the speaker including a diaphragm, a front portion of the diaphragm configured to produce a first plurality of sound waves, a back portion of the diaphragm configured to produce a second plurality of sound waves,
the cover configured to be coupled to the housing such that the cover and the housing collectively define an acoustic enclosure, the cover defining a first opening, the housing defining a second opening in fluid communication with the acoustic enclosure, the speaker coupled to the cover such that the first plurality of sound waves exits the first opening and the second plurality of sound waves exits the second opening, the acoustic enclosure configured such that the first plurality of sound waves is substantially in phase with the second plurality of sound waves when the first plurality of sound waves exits the first opening and the second plurality of sound waves exits the second opening.

19. The apparatus of claim 18, wherein the medicament delivery device includes:

an actuator configured to be moved relative to the housing to initiate movement of the medicament container within the housing; and a movable member removably coupled to the housing, the movable member configured to limit movement of the actuator when coupled to the housing, a portion of the movable member configured to be disposed within the second opening when the movable member is coupled to the housing.

20. The apparatus of claim 18, wherein the electronic circuit system includes an audio processor configured to output an electronic signal associated with recorded speech to the speaker via an electronic path devoid of a signal amplifier.

21. The apparatus of claim 18, wherein the medicament container includes epinephrine.

22. The apparatus of claim 1, wherein:

the cover defines at least a portion of a first exit path within which the first plurality of sound waves travels from the first portion of the audible output device to a region outside of the housing;

the housing defines at least a portion of a second exit path within which the second plurality of sound waves travels from the second portion of the audible output device to the region outside of the housing, a length of the first exit path different from a length of the second exit path.

23. The apparatus of claim 11, wherein the cover and the housing collectively define an acoustic enclosure defining at least one acoustic resonant frequency within an acoustic frequency range of the audible output device.

24. The apparatus of claim 11, wherein the second exit path is substantially devoid of a structure.

25. The apparatus of claim 18, wherein:

the cover defines a first exit path within which the first plurality of sound waves travels, the first exit path including at least the first opening; and the housing defines a second exit path within which the second plurality of sound waves travels, the second exit path including a portion of the acoustic enclosure, a length of the first exit path different from a length of the second exit path.

* * * * *